(12) United States Patent
Yang et al.

(10) Patent No.: US 9,139,548 B2
(45) Date of Patent: Sep. 22, 2015

(54) POLYCYCLIC DERIVATIVES, PREPARATION PROCESS AND PHARMACEUTICAL USE THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Fanglong Yang, Shanghai (CN); Qing Dong, Shanghai (CN); Jihui Han, Shanghai (CN); Chunfei Wang, Shanghai (CN); Ling Zhang, Shanghai (CN); Yang Wang, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/371,123

(22) PCT Filed: Dec. 27, 2012

(86) PCT No.: PCT/CN2012/087606
§ 371 (c)(1),
(2) Date: Jul. 8, 2014

(87) PCT Pub. No.: WO2013/104257
PCT Pub. Date: Jul. 18, 2013

(65) Prior Publication Data
US 2015/0005282 A1 Jan. 1, 2015

(30) Foreign Application Priority Data

Jan. 12, 2012 (CN) .......................... 2012 1 0008286

(51) Int. Cl.
C07D 307/00 (2006.01)
A61K 31/34 (2006.01)
C07D 307/80 (2006.01)
C07D 405/12 (2006.01)
C07D 407/12 (2006.01)

(52) U.S. Cl.
CPC ............ C07D 307/80 (2013.01); C07D 405/12 (2013.01); C07D 407/12 (2013.01)

(58) Field of Classification Search
CPC ........................... C07D 307/78; C07D 307/80
USPC .......................................... 549/469; 514/469
See application file for complete search history.

(56) References Cited

U.S. PATENT DOCUMENTS

| | | | |
|---|---|---|---|
| 2006/0258722 | A1 | 11/2006 | Yasuma et al. |
| 2007/0244155 | A1 | 10/2007 | Sharma et al. |
| 2011/0275797 | A1 | 11/2011 | Yokotani et al. |
| 2011/0313003 | A1 | 12/2011 | Shi et al. |

FOREIGN PATENT DOCUMENTS

| | | |
|---|---|---|
| CN | 101616913 A | 12/2009 |
| CN | 102186825 A | 9/2011 |
| CN | 102307860 A | 1/2012 |
| WO | 2004106276 A1 | 12/2004 |
| WO | 2005019151 A1 | 3/2005 |
| WO | 2005051890 A1 | 6/2005 |
| WO | 2005087710 A1 | 9/2005 |
| WO | 2008001931 A2 | 1/2008 |
| WO | 2010143733 A1 | 12/2010 |
| WO | 2011097958 A1 | 8/2011 |

OTHER PUBLICATIONS

Negoro et al J. Med. Chem. 2012, 55, 3960-3974.*
Int'l Search Report issued Mar. 21, 2013 in Int'l Application No. PCT/CN2012/087606.

* cited by examiner

*Primary Examiner* — John Mabry
(74) *Attorney, Agent, or Firm* — Panitch Schwarze Belisario & Nadel LLP

(57) ABSTRACT

Disclosed in the present invention are polycyclic derivatives as represented by general formula (I), the preparation method thereof, pharmaceutical compositions containing the derivatives and uses thereof as therapeutic agents, especially the GPR40 agonist and in preparation of drugs for treating diseases such as diabetes and metabolic disorders, etc., wherein each substituent in the general formula (I) has the same definition as in the description.

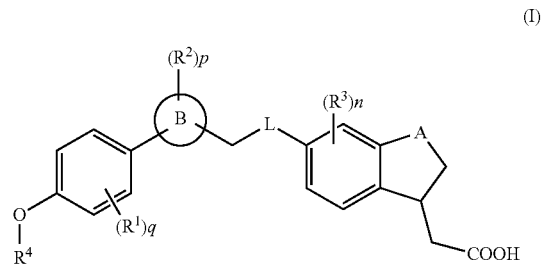

23 Claims, No Drawings

POLYCYCLIC DERIVATIVES, PREPARATION PROCESS AND PHARMACEUTICAL USE THEREOF

CROSS-REFERENCE TO RELATED APPLICATIONS

This application is a Section 371 of International Application No. PCT/CN2012/087606, filed on Dec. 27, 2012, which was published in the Chinese language on Jul. 18, 2013 under International Publication No. WO 2013/104257, and the disclosure of which is incorporated herein by reference.

FIELD OF THE INVENTION

This disclosure relates to novel polycyclic derivatives, preparation processes, pharmaceutical compositions containing the same, and their use as a therapeutic agent, particularly as a GPR40 agonist, and in the preparation of a medicament for the treatment of diabetes, metabolic syndrome, etc.

BACKGROUND OF THE INVENTION

Type II diabetes, also known as non-insulin-dependent diabetes mellitus or adult onset diabetes, is mainly where insulin secretion is too little in patients or the body cannot use insulin effectively (namely insulin resistance). Currently there are about 185 million diabetics around the world, in which type II diabetes accounts for about 90 to 95% of all diabetic patients, and it is growing at a rate of 6% per year. In 2010, the morbidity of type II diabetes has reached around 9.7% among Chinese adults over 20 years old.

Currently, therapies for type II diabetes include insulin secretagogues, such as sulphonylureas, which promote pancreatic 13 cells to produce more insulin; antidiabetic agents, such as metformin, which reduce the formation of glucose in the liver; activators of the peroxisome proliferator-activated receptor-γ (PPAR-γ), such as the thiazolidinediones, which improve insulin sensitivity and enhance the bioavailability of insulin; and α-glucosidase inhibitors, which interfere with glucose production in the gut. However, the current treatments of existing methods have certain deficiencies. For example, sulphonylureas and insulin injections can be associated with hypoglycemic episodes and weight gain. Furthermore, patients often lose response to sulphonylureas over time and produce tolerance. Metformin and α-glucosidase inhibitors often lead to gastrointestinal problems, and PPAR-γ agonists tend to cause weight gain and edema.

Research directed to several areas is ongoing in order to bring new, more effective antidiabetic drugs to the marketplace. For example, the present inventors are exploring ways to reduce excessive hepatic glucose production, enhance the transduction of the signal pathway of insulin-induced glucose uptake, improve glucose-stimulated insulin secretion (GSIS) in pancreatic β cells, and are studying obesity and fat metabolism, accumulation abnormalities, and the like.

Free fatty acids (FFA) play key roles in several aspects of metabolism. For example, they are the "priming," which enhances the response of insulin of the pancreatic β cells to glucose in the fasting state, and they are the starting point for lipogenesis. Initially, GPR40 was found in an orphan receptor form from the human genome. GPR40 is highly expressed in pancreatic β cells and insulin-secreting cell lines. GPR40, also known as fatty acid receptor 1 (FFAR1), is a member of the gene superfamily of G-protein coupled receptors ("GPCRs"). GPCRs are membrane proteins having seven transmembrane domains, and can respond to a variety of molecules, thereby activating intracellular signaling transduction pathways, and are critical for achieving a variety of physiological functions. GPR40 activation is linked to regulation of the $G_q$ family of intracellular signaling proteins and is accompanied with inducing the increase of calcium iron levels. GPR40 was the first fatty acid receptor to be identified on the cell surface, capable of binding the most common fatty acids in plasma such as palmitate, oleate, stearate, linoleate, and linolenate, etc. GPR40 could be considered as a 'nutrient sensing' receptor, playing several tissue-dependent roles, which may affect overall glucose utilization and/or fat metabolism. For example, long-chain FFAs amplify GSIS in pancreatic 13 cells through the activation of GPR40.

GPR40 regulators play an incretin effect to promote GSIS. Moreover, they can also be combined with various antidiabetic drugs. Based on the above, GPR40 agonists may be used for treating diabetes and associated conditions, particularly type II diabetes, obesity, glucose intolerance, insulin resistance, metabolic syndrome X, hyperlipidemia, hypercholesterolemia, atherosclerosis, neurodegenerative diseases (for example Alzheimer's disease), and other indications such as stroke. Taking GPR40 as a potential therapeutic target, a compound for finding and modifying GPR40 has a very important research value and application prospect.

Up to now, a series of GPR40 agonists has been disclosed by some patent applications, such as WO2005087710, WO2005051890, and WO2004106276 etc.

However, although a series of GPR40 agonists for the treatment of disorders such as diabetes and metabolic syndrome X, etc. were disclosed presently, there is still a need to develop new compounds with more effective activities. After continuous efforts, the present disclosure provides the compounds of fomula (I), and discovers that these compounds having such structures show better efficiency and function.

SUMMARY OF THE INVENTION

The present disclosure is directed to providing a compound of formula (I), or a tautomer, mesomer, racemate, enantiomer, diastereomer, or mixture thereof, or a pharmaceutically acceptable salt thereof, as well as metabolites, metabolic precursors or prodrugs thereof:

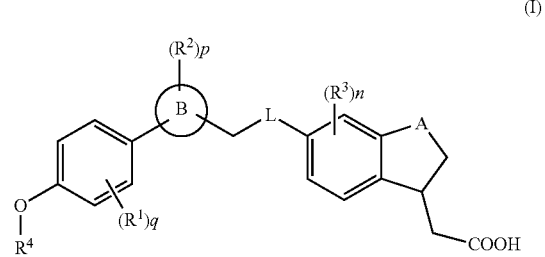

(I)

wherein:
A is selected from the group consisting of —O—, —CH$_2$— and —CH$_2$CH$_2$—;
L is selected from the group consisting of O— and —NH—;
ring B is selected from the group consisting of aryl and heteroaryl;
$R^1$, $R^2$ and $R^3$ are each independently selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR⁶R⁷, and —S(O)ₘR⁵, wherein the alkyl, alkoxy, cycloalkyl, heterocyclyl, aryl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR⁵, —OC(O)R⁵, —C(O)R⁵, —NHC(O)R⁵, —NR⁶R⁷, and —S(O)ₘR⁵;

R⁴ is selected from the group consisting of cycloalkyl, heterocyclyl, aryl, and heteroaryl, wherein the cycloalkyl, heterocyclyl, aryl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR⁵, —OC(O)R⁵, —C(O)R⁵, —NHC(O)R⁵, —NR⁶R⁷, and —S(O)ₘR⁵;

R⁵ is selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, cyano, alkoxy, cycloalkyl, heterocyclyl, aryl, heteroaryl, carboxyl, and alkoxycarbonyl;

R⁶ and R⁷ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, alkoxy, cycloalkyl, heterocyclyl, aryl, heteroaryl, carboxyl, and alkoxycarbonyl;

m is 0, 1, or 2;
n is 0, 1, 2, or 3;
p is 0, 1, 2, 3, or 4; and
q is 0, 1, 2, 3, or 4;
provided that: when p and n are 0, q is 2, R¹ is methyl, A is —O—, and R⁴ is heterocyclyl, the heterocyclyl does not contain an S atom.

In an embodiment of the invention, in the compound of formula (I) or a tautomer, mesomer, racemate, enantiomer, diastereomer, or mixture thereof, or a pharmaceutically acceptable salt thereof, ring B is aryl, preferably phenyl.

In another embodiment of the invention, the compound of formula (I) or a tautomer, mesomer, racemate, enantiomer, diastereomer, or mixture thereof, or a pharmaceutically acceptable salt thereof, is selected from a compound of formula (II) or a tautomer, racemate, enantiomer, diastereomer, or mixture thereof, or a pharmaceutically acceptable salt thereof:

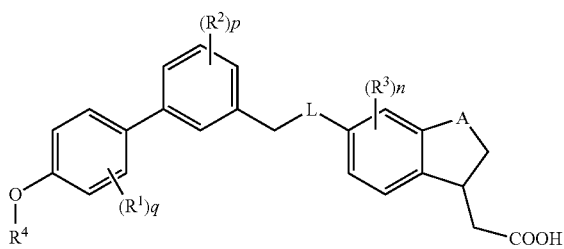

(II)

wherein A, L, R¹ to R⁴, n, p, and q are as defined in formula (I).

In another embodiment of the invention, in the compound of formula (I) or formula (II) or a tautomer, mesomer, racemate, enantiomer, diastereomer, or mixture thereof, or a pharmaceutically acceptable salt thereof, L is —O—.

In another embodiment of the invention, in the compound of formula (I) or formula (II) or a tautomer, mesomer, racemate, enantiomer, diastereomer, or mixture thereof, or a pharmaceutically acceptable salt thereof, R¹ is selected from the group consisting of alkyl, halogen, and hydroxyalkyl.

In another embodiment of the invention, in the compound of formula (I) or formula (II) or a tautomer, mesomer, racemate, enantiomer, diastereomer, or mixture thereof, or a pharmaceutically acceptable salt thereof, R² is selected from the group consisting of hydrogen, alkyl and halogen.

In another embodiment of the invention, in the compound of formula (I) or formula (II) or a tautomer, mesomer, racemate, enantiomer, diastereomer, or mixture thereof, or a pharmaceutically acceptable salt thereof, R³ is hydrogen.

In another embodiment of the invention, in the compound of formula (I) or formula (II) or a tautomer, mesomer, racemate, enantiomer, diastereomer, or mixture thereof, or a pharmaceutically acceptable salt thereof, R⁴ is selected from the group consisting of cycloalkyl, heterocyclyl, and heteroaryl, wherein the cycloalkyl, heterocyclyl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR⁵, —OC(O)R⁵, —C(O)R⁵, —NHC(O)R⁵, —NR⁶R⁷, and —S(O)ₘR⁵; and R⁵, R⁶, R⁷, and m are as defined in formula (I).

In another embodiment of the invention, in the compound of formula (I) or formula (II) or a tautomer, mesomer, racemate, enantiomer, diastereomer, or mixture thereof, and a pharmaceutically acceptable salt thereof, R⁴ is selected from the group consisting of the following cycloalkyl, heterocyclyl, and heteroaryl:

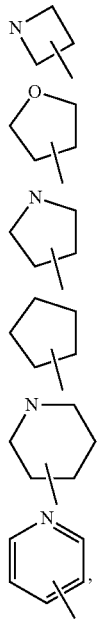

wherein the cycloalkyl, heterocyclyl, or heteroaryl is each optionally substituted with one or more groups selected from the group consisting of halogen, hydroxyl, alkyl, alkoxy, —C(O)OR⁵, —OC(O)R⁵, —C(O)R⁵, —NHC(O)R⁵, —NR⁶R⁷, and —S(O)ₘR⁵; and R⁵, R⁶, R⁷, and m are as defined in formula (I).

Furthermore, in another embodiment of the invention, the compound of formula (II) or a tautomer, mesomer, racemate, enantiomer, diastereomer, or mixture thereof, or a pharmaceutically acceptable salt thereof, is selected from a compound of formula (III) or a tautomer, mesomer, racemate, enantiomer, diastereomer, or mixture thereof, or a pharmaceutically acceptable salt thereof:

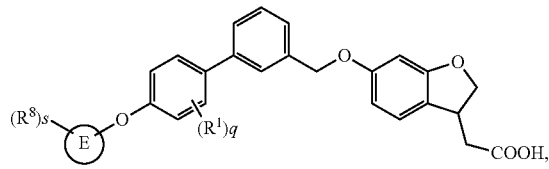

(III)

wherein:
ring E is selected from the group consisting of cycloalkyl, heterocyclyl, and heteroaryl;
$R^1$ is selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR$^6$R$^7$, and —S(O)$_m$R$^5$, wherein the alkyl, cycloalkyl, alkoxy, heterocyclyl, aryl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR$^5$, —OC(O) R$^5$, —C(O)R$^5$, —NHC(O)R$^5$, —NR$^6$R$^7$, and —S(O)$_m$ R$^5$;
$R^5$ is selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, cyano, alkoxy, cycloalkyl, heterocyclyl, aryl, heteroaryl, carboxyl, and alkoxycarbonyl;
$R^6$ and $R^7$ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, alkoxy, cycloalkyl, heterocyclyl, aryl, heteroaryl, carboxyl, and alkoxycarbonyl;
$R^8$ is selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR$^6$R$^7$, and —S(O)$_m$R$^5$;
m is 0, 1, or 2;
q is 0, 1, 2, 3, or 4; and
s is 0, 1, 2, or 3;
provided that: when q is 2, $R^1$ is methyl, and E is heterocyclyl, the heterocyclyl does not contain an S atom.

In another embodiment of the invention, in the compound of formula (III) or a tautomer, mesomer, racemate, enantiomer, diastereomer, or mixture thereof, or a pharmaceutically acceptable salt thereof, ring E is selected from the group consisting of the following cycloalkyl, heterocyclyl, and heteroaryl:

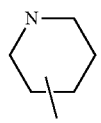

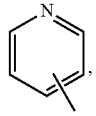

wherein the cycloalkyl, heterocyclyl, or heteroaryl is each optionally substituted with one or more groups selected from the group consisting of halogen, hydroxyl, alkyl, alkoxy, —C(O)OR$^5$, —OC(O)R$^5$, —C(O)R$^5$, —NHC(O)R$^5$, —NR$^6$R$^7$, and —S(O)$_m$R$^5$; and R$^5$, R$^6$, R$^7$, and m are as defined in formula (III).

Furthermore, in another embodiment of the invention, the compound of formula (III) or a tautomer, mesomer, racemate, enantiomer, diastereomer, or mixture thereof, or a pharmaceutically acceptable salt thereof, is selected from a compound of formula (IV) or a tautomer, mesomer, racemate, enantiomer, diastereomer, or mixture thereof, or a pharmaceutically acceptable salt thereof:

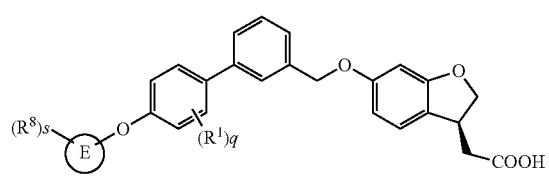

(IV)

wherein E, $R^1$, $R^8$, s, and q are as defined in formula (III).

The compound of formula (I) of the present disclosure preferably includes, but is not limited to:

| Example No. | Structure and name |
|---|---|
| 1 | 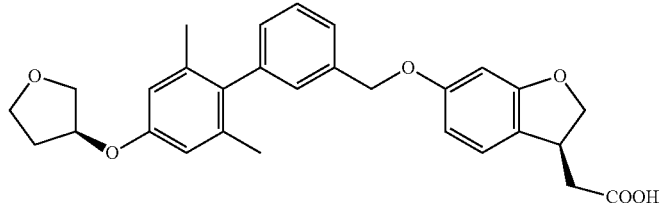 [SMILES: Cc1cc(O[C@H]2CCOC2)cc(C)c1-c1cccc(COc2ccc3c(c2)OC[C@H]3CC(=O)O)c1]<br>2-((S)-6-((2',6'-dimethyl-4'-(((S)-tetrahydrofuran-3-yl)oxy)biphenyl-3-yl)methoxy)-2,3-dihydrobenzofuran-3-yl)acetic acid |
| 2 | 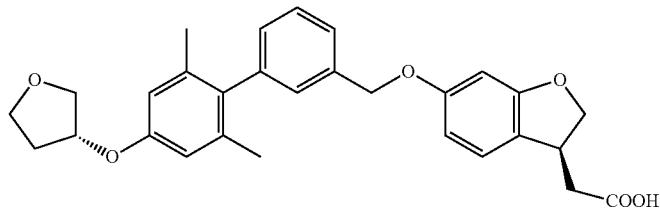 [SMILES: Cc1cc(O[C@@H]2CCOC2)cc(C)c1-c1cccc(COc2ccc3c(c2)OC[C@H]3CC(=O)O)c1]<br>2-((S)-6-((2',6'-dimethyl-4'-(((R)-tetrahydrofuran-3-yl)oxy)biphenyl-3-yl)methoxy)-2,3-dihydrobenzofuran-3-yl)acetic acid |
| 3 | 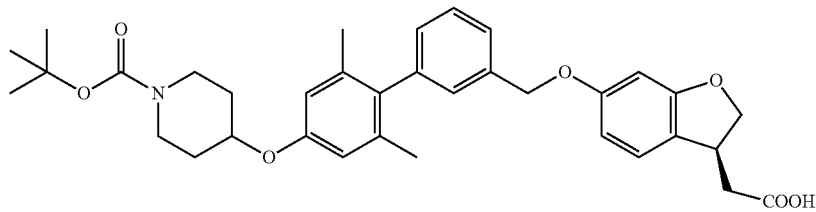 [SMILES: Cc1cc(OC2CCN(C(=O)OC(C)(C)C)CC2)cc(C)c1-c1cccc(COc2ccc3c(c2)OC[C@H]3CC(=O)O)c1]<br>(S)-2-(6-((4'-((1-(tert-butoxycarbonyl)piperidin-4-yl)oxy)-2',6'-dimethylbiphenyl-3-yl)methoxy)-2,3-dihydrobenzofuran-3-yl)acetic acid |
| 4 | 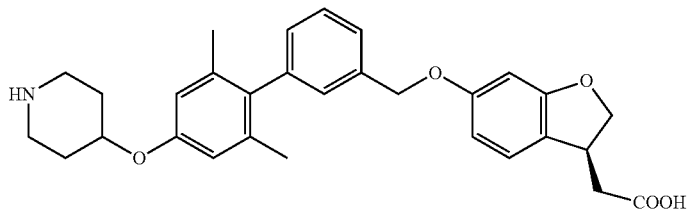 [SMILES: Cc1cc(OC2CCNCC2)cc(C)c1-c1cccc(COc2ccc3c(c2)OC[C@H]3CC(=O)O)c1]<br>(S)-2-(6-((2',6'-dimethyl-4'-(piperidin-4-yl)oxy)biphenyl-3-yl)methoxy)-2,3-dihydrobenzofuran-3-yl)acetic acid |
| 5 | 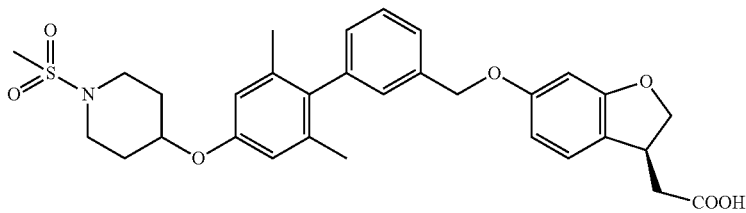 [SMILES: Cc1cc(OC2CCN(S(C)(=O)=O)CC2)cc(C)c1-c1cccc(COc2ccc3c(c2)OC[C@H]3CC(=O)O)c1]<br>(S)-2-(6-((2',6'-dimethyl-4'-((1-(methylsulfonyl)piperidin-4-yl)oxy)biphenyl-3-yl)methoxy)-2,3-dihydrobenzofuran-3-yl)acetic acid |

-continued

| Example No. | Structure and name |
|---|---|
| 6 | 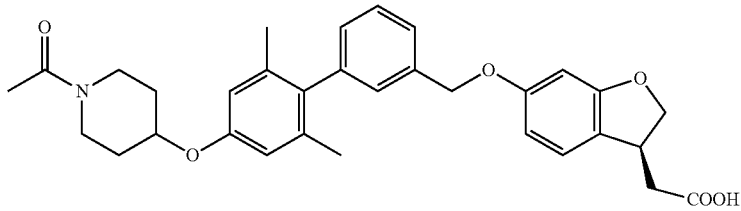 [SMILES: CC(=O)N1CCC(Oc2cc(C)c(-c3cccc(COc4ccc5c(c4)OC[C@H]5CC(=O)O)c3)c(C)c2)CC1]<br>(S)-2-(6-((4'-((1-acetylpiperidin-4-yl)oxy)-2',6'-dimethylbiphenyl-3-yl)methoxy)-2,3-dihydrobenzofuran-3-yl)acetic acid |
| 7 | 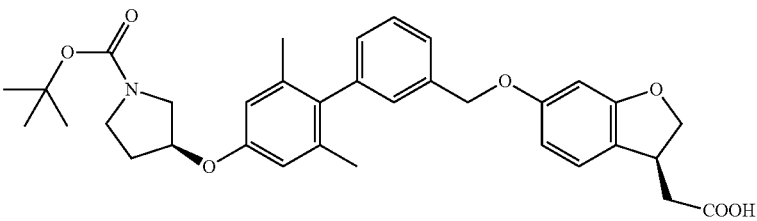 [SMILES: Cc1cc(O[C@H]2CCN(C(=O)OC(C)(C)C)C2)cc(C)c1-c1cccc(COc2ccc3c(c2)OC[C@H]3CC(=O)O)c1]<br>2-((S)-6-((4'-(((S)-1-(tert-butoxycarbonyl)pyrrolidin-3-yl)oxy)-2',6'-dimethylbiphenyl-3-yl)methoxy)-2,3-dihydrobenzofuran-3-yl)acetic acid |
| 8 | 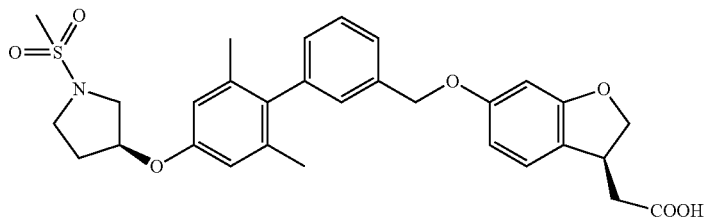 [SMILES: Cc1cc(O[C@H]2CCN(S(C)(=O)=O)C2)cc(C)c1-c1cccc(COc2ccc3c(c2)OC[C@H]3CC(=O)O)c1]<br>2-((S)-6-((2',6'-dimethyl-4'-(((S)-1-(methylsulfonyl)pyrrolidin-3-yl)oxy)biphenyl-3-yl)methoxy)-2,3-dihydrobenzofuran-3-yl)acetic acid |
| 9 | 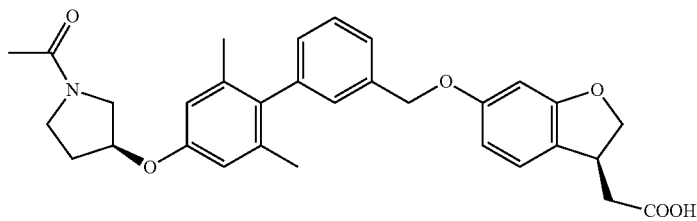 [SMILES: CC(=O)N1CC[C@H](Oc2cc(C)c(-c3cccc(COc4ccc5c(c4)OC[C@H]5CC(=O)O)c3)c(C)c2)C1]<br>2-((S)-6-((4'-(((S)-1-acetylpyrrolidin-3-yl)oxy)-2',6'-dimethylbiphenyl-3-yl)methoxy)-2,3-dihydrobenzofuran-3-yl)acetic acid |
| 10 | 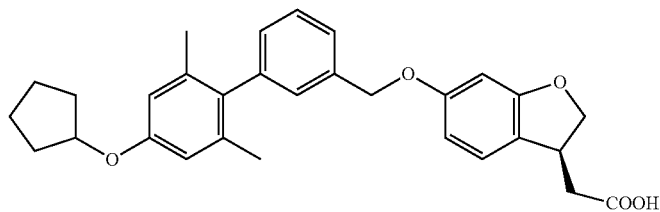 [SMILES: Cc1cc(OC2CCCC2)cc(C)c1-c1cccc(COc2ccc3c(c2)OC[C@H]3CC(=O)O)c1]<br>(S)-2-(6-((4'-(cyclopentyloxy)-2',6'-dimethylbiphenyl-3-yl)methoxy)-2,3-dihydrobenzofuran-3-yl)acetic acid |

| Example No. | Structure and name |
|---|---|
| 11 | 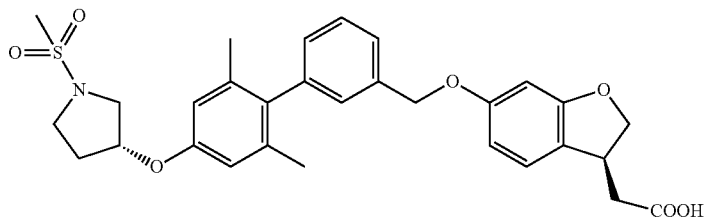 [SMILES: Cc1cc(O[C@@H]2CCN(S(C)(=O)=O)C2)cc(C)c1-c1cccc(COc2ccc3c(c2)OC[C@H]3CC(=O)O)c1]<br>2-((S)-6-((2',6'-dimethyl-4'-(((R)-1-(methylsulfonyl)pyrrolidin-3-yl)oxy)biphenyl-3-yl)methoxy)-2,3-dihydrobenzofuran-3-yl)acetic acid |
| 12 | 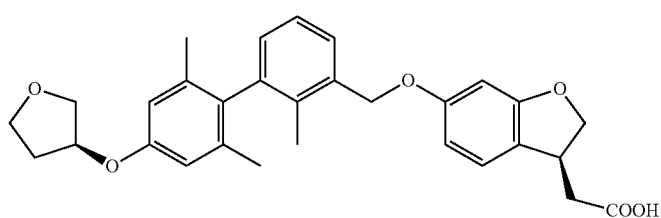 [SMILES: Cc1cc(O[C@H]2CCOC2)cc(C)c1-c1cccc(COc2ccc3c(c2)OC[C@H]3CC(=O)O)c1C]<br>2-((S)-6-((2,2',6'-trimethyl-4'-(((S)-tetrahydrofuran-3-yl)oxy)biphenyl-3-yl)methoxy)-2,3-dihydrobenzofuran-3-yl)acetic acid |
| 13 | 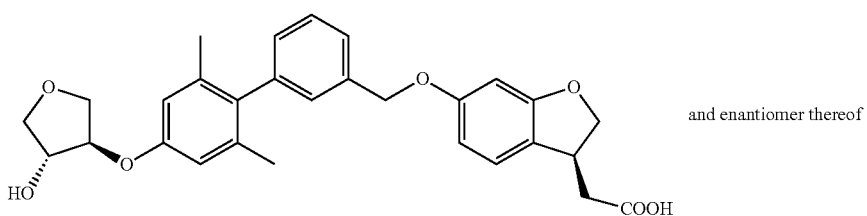 [SMILES: Cc1cc(O[C@@H]2COC[C@H]2O)cc(C)c1-c1cccc(COc2ccc3c(c2)OC[C@H]3CC(=O)O)c1] and enantiomer thereof<br>2-((S)-6-((4'-(((3R,4R)/(3S,4S)-4-hydroxytetrahydrofuran-3-yl)oxy)-2',6'-dimethylbiphenyl-3-yl)methoxy)-2,3-dihydrobenzofuran-3-yl)acetic acid |
| 14 | 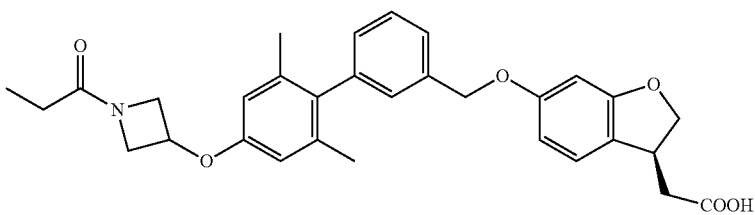 [SMILES: CCC(=O)N1CC(Oc2cc(C)c(-c3cccc(COc4ccc5c(c4)OC[C@H]5CC(=O)O)c3)c(C)c2)C1]<br>(S)-2-(6-((2',6'-dimethyl-4'-((1-propionylazetidin-3-yl)oxy)biphenyl-3-yl)methoxy)-2,3-dihydrobenzofuran-3-yl)acetic acid |
| 15 | 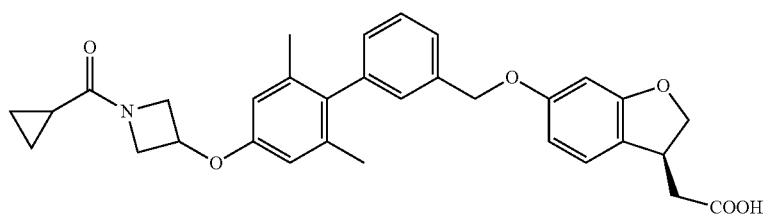 [SMILES: Cc1cc(OC2CN(C(=O)C3CC3)C2)cc(C)c1-c1cccc(COc2ccc3c(c2)OC[C@H]3CC(=O)O)c1]<br>(S)-2-(6-((4'-((1-(cyclopropanecarbonyl)azetidin-3-yl)oxy)-2',6'-dimethylbiphenyl-3-yl)methoxy)-2,3-dihydrobenzofuran-3-yl)acetic acid |

| Example No. | Structure and name |
|---|---|
| 16 | 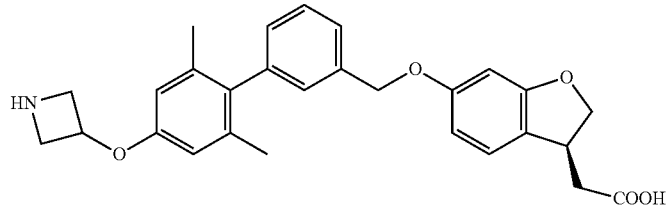 [SMILES: Cc1cc(OC2CNC2)cc(C)c1-c1cccc(COc2ccc3c(c2)OC[C@H]3CC(=O)O)c1]<br>(S)-2-(6-((4'-(azetidin-3-yloxy)-2',6'-dimethylbiphenyl-3-yl)methoxy)-2,3-dihydrobenzofuran-3-yl)acetic acid |
| 17 | 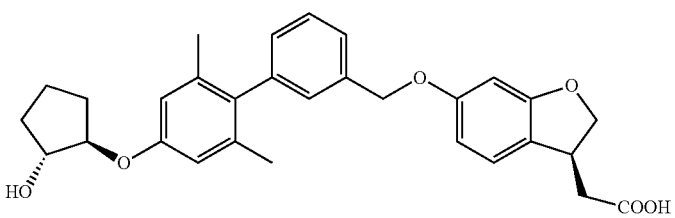 [SMILES: Cc1cc(O[C@@H]2CCC[C@H]2O)cc(C)c1-c1cccc(COc2ccc3c(c2)OC[C@H]3CC(=O)O)c1]<br>2-((S)-6-(((4'-((1R,2R)/(1S,2S)-2-hydroxycyclopentyl)oxy)-2',6'-dimethylbiphenyl-3-yl)methoxy)-2,3-dihydrobenzofuran-3-yl)acetic acid |
| 18 | 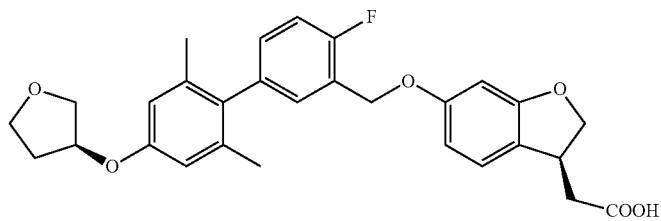 [SMILES: Cc1cc(O[C@H]2CCOC2)cc(C)c1-c1ccc(F)c(COc2ccc3c(c2)OC[C@H]3CC(=O)O)c1]<br>2-((S)-6-((4-fluoro-2',6'-dimethyl-4'-(((S)-tetrahydrofuran-3-yl)oxy)biphenyl-3-yl)methoxy)-2,3-dihydrobenzofuran-3-yl)acetic acid |
| 19 | 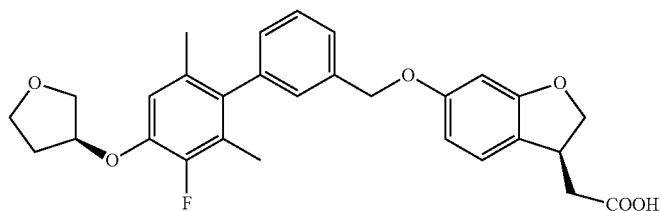 [SMILES: Cc1cc(O[C@H]2CCOC2)c(F)c(C)c1-c1cccc(COc2ccc3c(c2)OC[C@H]3CC(=O)O)c1]<br>2-((S)-6-((3'-fluoro-2',6'-dimethyl-4'-(((S)-tetrahydrofuran-3-yl)oxy)biphenyl-3-yl)methoxy)-2,3-dihydrobenzofuran-3-yl)acetic acid |
| 20 | 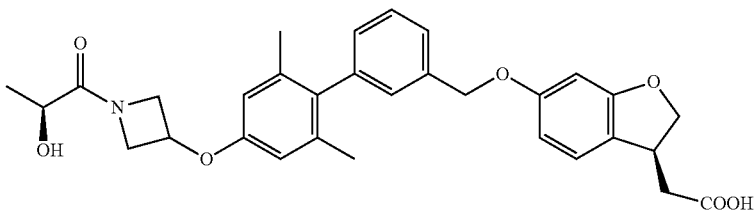 [SMILES: Cc1cc(OC2CN(C(=O)[C@H](C)O)C2)cc(C)c1-c1cccc(COc2ccc3c(c2)OC[C@H]3CC(=O)O)c1]<br>2-((S)-6-((4'-((1-((S)-2-hydroxypropanoyl)azetidin-3-yl)oxy)-2',6'-dimethylbiphenyl-3-yl)methoxy)-2,3-dihydrobenzofuran-3-yl)acetic acid |

| Example No. | Structure and name |
|---|---|
| 21 | 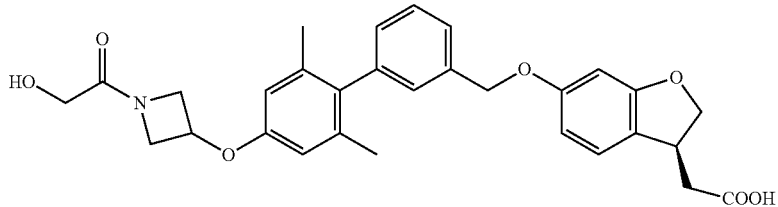 [SMILES: Cc1cc(OC2CN(C(=O)CO)C2)cc(C)c1-c1cccc(COc2ccc3c(c2)OC[C@H]3CC(=O)O)c1]<br>(S)-2-(6-((4'-((1-(2-hydroxyacetyl)azetidin-3-yl)oxy)-2',6'-dimethylbiphenyl-3-yl)methoxy)-2,3-dihydrobenzofuran-3-yl)acetic acid |
| 22 | 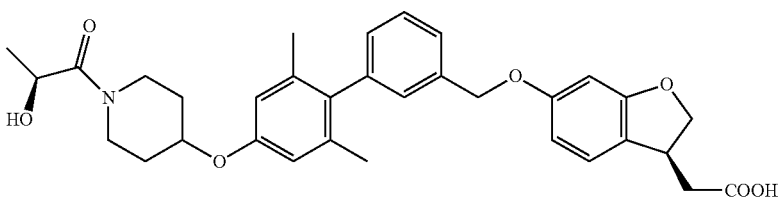 [SMILES: Cc1cc(OC2CCN(C(=O)[C@H](C)O)CC2)cc(C)c1-c1cccc(COc2ccc3c(c2)OC[C@H]3CC(=O)O)c1]<br>2-((S)-6-((4'-((1-((S)-2-hydroxypropanoyl)piperidin-4-yl)oxy)-2',6'-dimethylbiphenyl-3-yl)methoxy)-2,3-dihydrobenzofuran-3-yl)acetic acid |
| 23 | 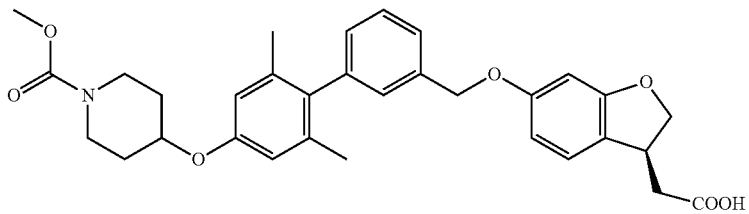 [SMILES: COC(=O)N1CCC(Oc2cc(C)c(-c3cccc(COc4ccc5c(c4)OC[C@H]5CC(=O)O)c3)c(C)c2)CC1]<br>(S)-2-(6-((4'-((1-(methoxycarbonyl)piperidin-4-yl)oxy)-2',6'-dimethylbiphenyl-3-yl)methoxy)-2,3-dihydrobenzofuran-3-yl)acetic acid |
| 24 | 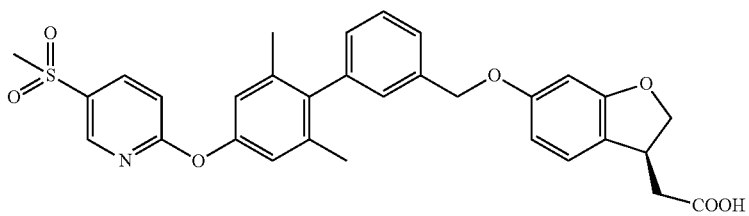 [SMILES: Cc1cc(Oc2ccc(S(C)(=O)=O)cn2)cc(C)c1-c1cccc(COc2ccc3c(c2)OC[C@H]3CC(=O)O)c1]<br>(S)-2-(6-((2',6'-dimethyl-4'-((5-(methylsulfonyl)pyridin-2-yl)oxy)biphenyl-3-yl)methoxy)-2,3-dihydrobenzofuran-3-yl)acetic acid |
| 25 | 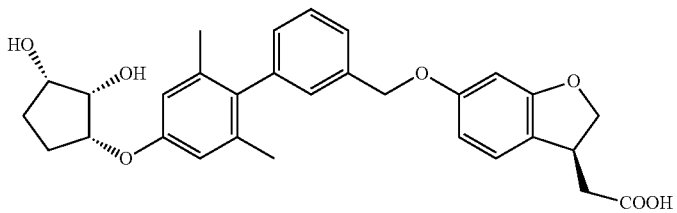 [SMILES: Cc1cc(O[C@@H]2CC[C@H](O)[C@@H]2O)cc(C)c1-c1cccc(COc2ccc3c(c2)OC[C@H]3CC(=O)O)c1]<br>2-((S)-6-((4'-(((1R,2S,3S)-2,3-dihydroxycyclopentyl)oxy)-2',6'-dimethylbiphenyl-3-yl)methoxy)-2,3-dihydrobenzofuran-3-yl)acetic acid |

| Example No. | Structure and name |
|---|---|
| 26 | 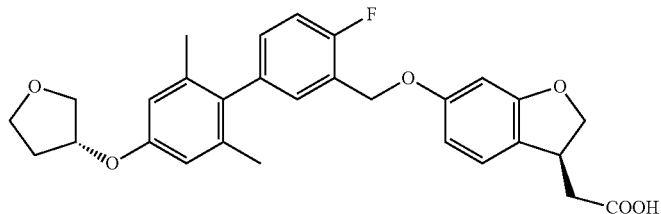 [SMILES: Cc1cc(O[C@@H]2CCOC2)cc(C)c1-c1ccc(F)c(COc2ccc3c(c2)OC[C@H]3CC(=O)O)c1]
2-((S)-6-((4-fluoro-2',6'-dimethyl-4'-(((R)-tetrahydrofuran-3-yl)oxy) biphenyl-3-yl)methoxy)-2,3-dihydrobenzofuran-3-yl)acetic acid |
| 27 | 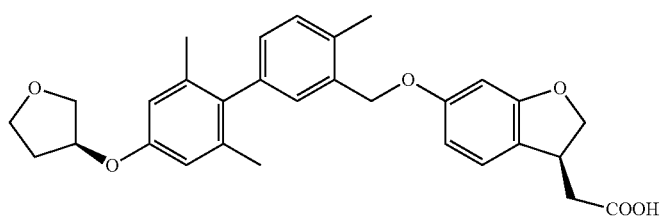 [SMILES: Cc1ccc(-c2c(C)cc(O[C@H]3CCOC3)cc2C)cc1COc1ccc2c(c1)OC[C@H]2CC(=O)O]
2-((S)-6-((2',4,6'-trimethyl-4'-(((S)-tetrahydrofuran-3-yl)oxy)biphenyl-3-yl)methoxy)-2,3-dihydrobenzofuran-3-yl)acetic acid |
| 28 | 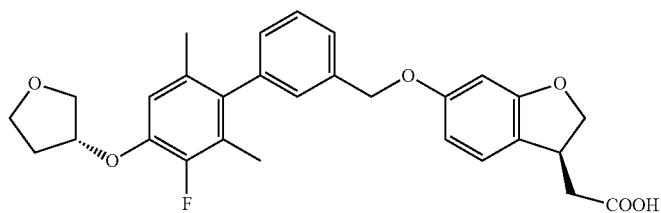 [SMILES: Cc1cc(O[C@@H]2CCOC2)c(F)c(C)c1-c1cccc(COc2ccc3c(c2)OC[C@H]3CC(=O)O)c1]
2-((S)-6-((3'-fluoro-2',6'-dimethyl-4'-(((R)-tetrahydrofuran-3-yl)oxy) biphenyl-3-yl)methoxy)-2,3-dihydrobenzofuran-3-yl)acetic acid |
| 29 | 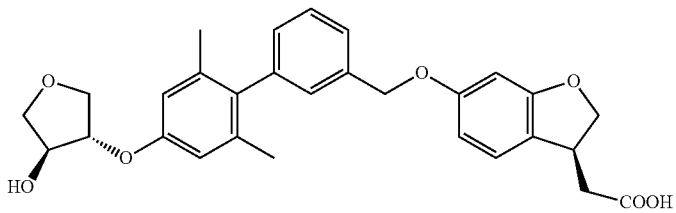 [SMILES: Cc1cc(O[C@H]2COC[C@@H]2O)cc(C)c1-c1cccc(COc2ccc3c(c2)OC[C@H]3CC(=O)O)c1]
2-((S)-6-((4'-(((3S,4S)-4-hydroxytetrahydrofuran-3-yl)oxy)-2',6'-dimethylbiphenyl-3-yl)methoxy)-2,3-dihydrobenzofuran-3-yl)acetic acid |
| 30 | 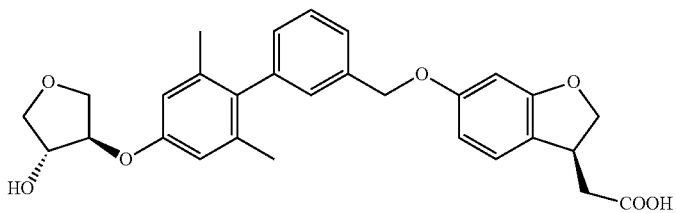 [SMILES: Cc1cc(O[C@@H]2COC[C@H]2O)cc(C)c1-c1cccc(COc2ccc3c(c2)OC[C@H]3CC(=O)O)c1]
2-((S)-6-((4'-(((3R,4R)-4-hydroxytetrahydrofuran-3-yl)oxy)-2',6'-dimethylbiphenyl-3-yl)methoxy)-2,3-dihydrobenzofuran-3-yl)acetic acid |

| Example No. | Structure and name |
|---|---|
| 31 | 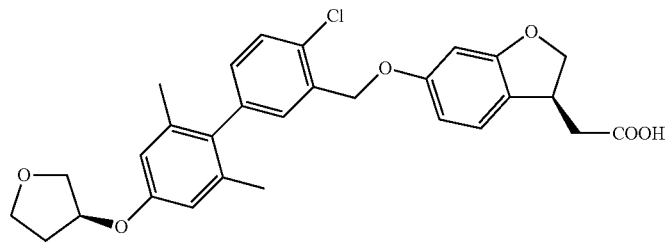 [SMILES: Cc1cc(O[C@H]2CCOC2)cc(C)c1-c1ccc(Cl)c(COc2ccc3c(c2)OC[C@H]3CC(=O)O)c1]<br>2-((S)-6-((4-chloro-2',6'-dimethyl-4'-(((S)-tetrahydrofuran-3-yl)oxy)biphenyl-3-yl)methoxy)-2,3-dihydrobenzofuran-3-yl)acetic acid |
| 32 | 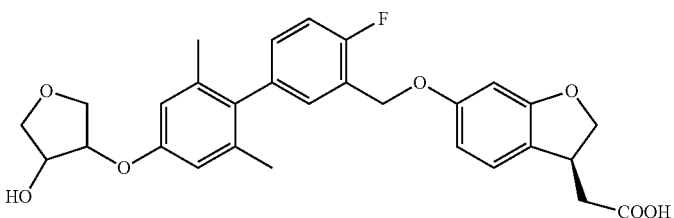 [SMILES: Cc1cc(OC2COCC2O)cc(C)c1-c1ccc(F)c(COc2ccc3c(c2)OC[C@H]3CC(=O)O)c1]<br>2-((3S)-6-((4-fluoro-4'-((4-hydroxytetrahydrofuran-3-yl)oxy)-2',6'-dimethylbiphenyl-3-yl)methoxy)-2,3-dihydrobenzofuran-3-yl)acetic acid |
| 33 | 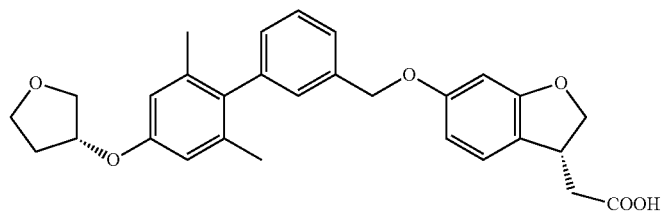 [SMILES: Cc1cc(O[C@@H]2CCOC2)cc(C)c1-c1cccc(COc2ccc3c(c2)OC[C@@H]3CC(=O)O)c1]<br>2-((R)-6-((2',6'-dimethyl-4'-(((R)-tetrahydrofuran-3-yl)oxy)biphenyl-3-yl)methoxy)-2,3-dihydrobenzofuran-3-yl)acetic acid |
| 34 | 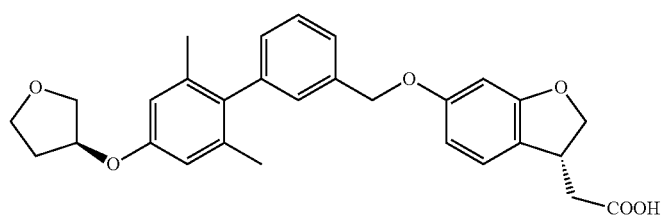 [SMILES: Cc1cc(O[C@H]2CCOC2)cc(C)c1-c1cccc(COc2ccc3c(c2)OC[C@@H]3CC(=O)O)c1]<br>2-((R)-6-((2',6'-dimethyl-4'-(((S)-tetrahydrofuran-3-yl)oxy)biphenyl-3-yl)methoxy)-2,3-dihydrobenzofuran-3-yl)acetic acid |
| 35 | 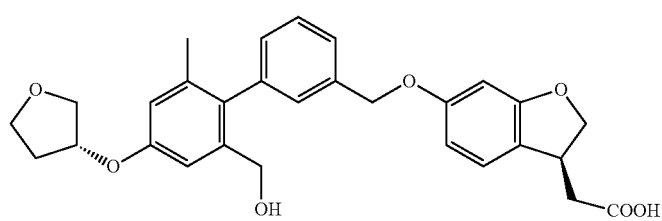 [SMILES: Cc1cc(O[C@@H]2CCOC2)cc(CO)c1-c1cccc(COc2ccc3c(c2)OC[C@H]3CC(=O)O)c1]<br>2-((S)-6-((2'-(hydroxymethyl)-6'-methyl-4'-(((R)-tetrahydrofuran-3-yl)oxy)biphenyl-3-yl)methoxy)-2,3-dihydrobenzofuran-3-yl)acetic acid |

| Example No. | Structure and name |
|---|---|
| 36 | 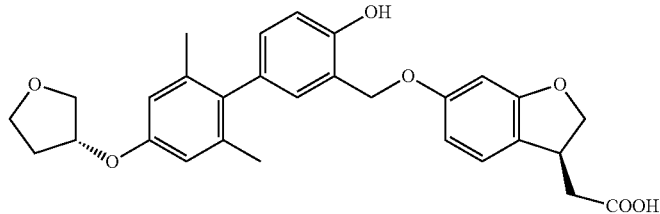 [SMILES: Cc1cc(O[C@@H]2CCOC2)cc(C)c1-c1ccc(O)c(COc2ccc3c(c2)OC[C@H]3CC(=O)O)c1]

2-((S)-6-((4-hydroxy-2',6'-dimethyl-4'-(((R)-tetrahydrofuran-3-yl)oxy)biphenyl-3-yl)methoxy)-2,3-dihydrobenzofuran-3-yl)acetic acid | or a tautomer, mesomer, racemate, enantiomer, diastereoisomer, or mixture thereof, or a pharmaceutically acceptable salt thereof.

The present disclosure relates to a compound of formula (IA) as intermediates in the synthesis of the compound of formula (I) or a tautomer, mesomer, racemate, enantiomer, diastereoisomer, or mixture thereof, or a pharmaceutically acceptable salt thereof:

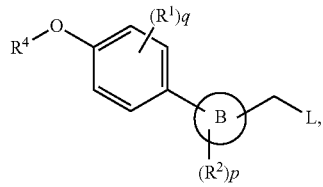

(IA)

wherein ring B, L, $R^1$, $R^2$, $R^4$, p, and q are as defined in formula (I).

The present disclosure relates to a preparation process of the compound of formula (I), or a tautomer, mesomer, racemate, enantiomer, diastereoisomer, or mixture thereof, or a pharmaceutically acceptable salt thereof, comprising the steps of:

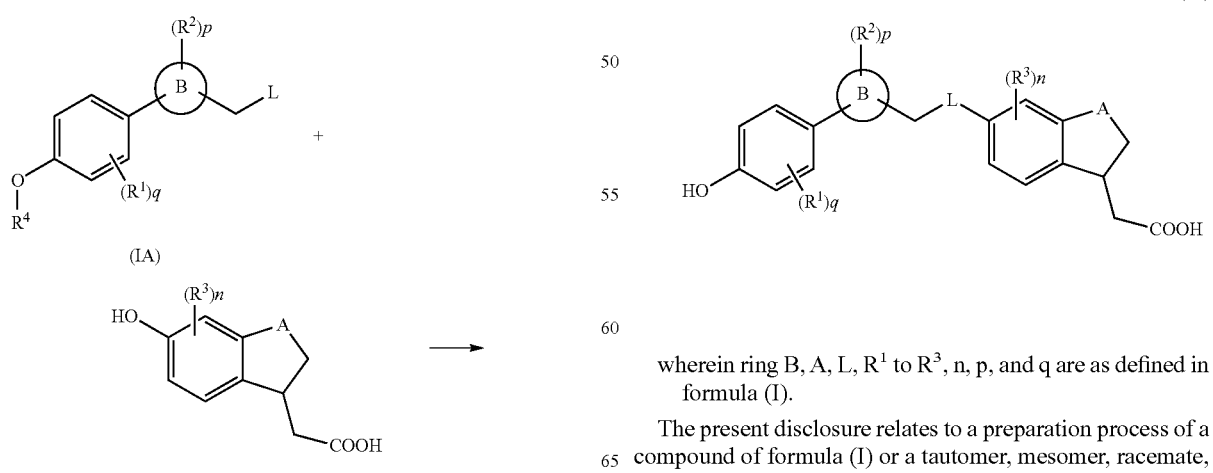

condensing a compound of formula (IA) with a hydroxyl-substituted benzocyclic compound in a solvent; optionally further carrying out ester hydrolysis under basic conditions to obtain the compound of formula (I), wherein the alkaline condition is provided by an alkali metal hydroxide, preferably sodium hydroxide or potassium hydroxide;

wherein ring B, A, L, $R^1$ to $R^4$, n, p, and q are as defined in formula (I).

The present disclosure relates to a compound of formula (IB):

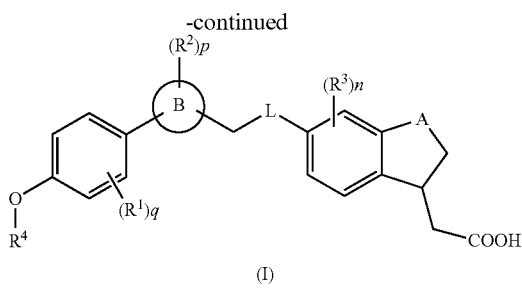

(IB)

wherein ring B, A, L, $R^1$ to $R^3$, n, p, and q are as defined in formula (I).

The present disclosure relates to a preparation process of a compound of formula (I) or a tautomer, mesomer, racemate, enantiomer, diastereoisomer, or mixture thereof, or a pharmaceutically acceptable salt thereof, comprising the steps of:

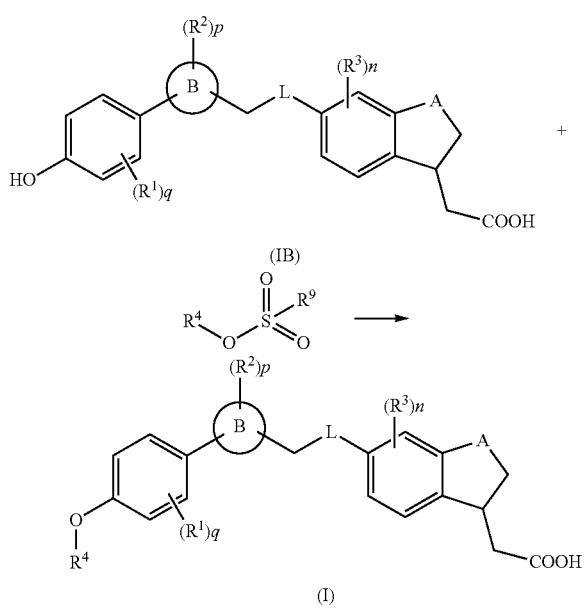

reacting a compound of formula (IB) and an $R^4$-substituted alkyl sulfonate in a solvent, optionally further carrying out ester hydrolysis under basic conditions to obtain the compound of formula (I), wherein the alkaline condition is provided by an alkali metal hydroxide, preferably sodium hydroxide or potassium hydroxide;

wherein ring B, A, L, $R^1$ to $R^4$, n, p, and q are as defined in formula (I), and $R^9$ is alkyl, preferably methyl.

Furthermore, in another aspect, the present disclosure relates to a pharmaceutical composition comprising a therapeutically effective amount of a compound of formula (I), or a tautomer, mesomer, racemate, enantiomer, diastereomer, or mixture thereof, or a pharmaceutically acceptable salt thereof or prodrug thereof, and a pharmaceutically acceptable carrier or excipient.

In still another aspect, the present disclosure also relates to a use of the compound of formula (I) or a tautomer, mesomer, racemate, enantiomer, diastereoisomer, or mixture thereof, or a pharmaceutically acceptable salt thereof, or the pharmaceutical composition comprising the same, in the preparation of a medicament as a GPR40 receptor regulator.

In still another aspect, the present disclosure relates to the compound of formula (I) or a tautomer, mesomer, racemate, enantiomer, diastereomer, or mixture thereof, or a pharmaceutically acceptable salt thereof, or the pharmaceutical composition comprising the same, for use as a GPR40 receptor regulator.

In still another aspect, the present disclosure relates to a method of regulating GPR40 receptor, comprising a step of administering to a subject in need thereof a therapeutically effective amount of a compound of formula (I), or a tautomer, mesomer, racemate, enantiomer, diastereomer, or mixture thereof, or a pharmaceutically acceptable salt thereof, or a pharmaceutical composition comprising the same.

The present diclosure relates to a use of the compound of formula (I), or a tautomer, mesomer, racemate, enantiomer, diastereoisomer, or mixture thereof, or a pharmaceutically acceptable salt thereof, or a pharmaceutical composition comprising the same, in the preparation of a medicament as a GPR40 agonist.

In another aspect, the present diclosure relates to a compound of formula (I) or a tautomer, mesomer, racemate, enantiomer, diastereomer, or mixture thereof, or a pharmaceutically acceptable salt thereof, or a pharmaceutical composition comprising the same, for use as a GPR40 agonist.

In still another aspect, the present diclosure relates to a method of activating GPR40 receptor, comprising a step of administering to a subject in need thereof a therapeutically effective amount of a compound of formula (I), or a tautomer, mesomer, racemate, enantiomer, diastereomer, or mixture thereof, or a pharmaceutically acceptable salt thereof, or a pharmaceutical composition comprising the same.

The present diclosure also relates to a use of a compound of formula (I), or a tautomer, mesomer, racemate, enantiomer, diastereomer, or mixture thereof, or a pharmaceutically acceptable salt thereof, or a pharmaceutical composition comprising the same in the preparation of a medicament for the treatment of the disorders of diabetes and metabolic syndromes, preferably the diabetes is type II diabetes.

In still another aspect, the present diclosure relates to a method of preventing and treating the disorders of diabetes and metabolic syndromes, comprising a step of administering to a subject in need thereof a therapeutically effective amount of a compound of formula (I), or a tautomer, mesomer, racemate, enantiomer, diastereomer, or mixture thereof, or a pharmaceutically acceptable salt thereof, or a pharmaceutical composition comprising the same, preferably the diabetes is type II diabetes.

In still another aspect, the present diclosure relates to a compound of formula (I), or a tautomer, mesomer, racemate, enantiomer, diastereomer, or mixture thereof, or a pharmaceutically acceptable salt thereof, or a pharmaceutical composition containing the same, for use as a medicament for the prevention and treatment of the disorders of diabetes and metabolic syndromes, preferably the diabetes is type II diabetes.

In still another aspect, the present diclosure relates to a method of regulating insulin, comprising a step of administering to a subject in need thereof a therapeutically effective amount of a compound of formula (I), or tautomer, mesomer, racemate, enantiomer, diastereomer, or mixture thereof, or a pharmaceutically acceptable salt thereof, or a pharmaceutical composition comprising the same.

In still another aspect, the present diclosure relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for regulating insulin.

The present diclosure relates to a use of a compound of formula (I), or a tautomer, mesomer, racemate, enantiomer, diastereoisomer, or mixture thereof, or a pharmaceutically acceptable salt thereof, or a pharmaceutical composition comprising the same, in the preparation of a medicament for regulating insulin.

DETAILED DESCRIPTION OF THE INVENTION

Unless otherwise stated, the following terms used in the specification and claims have the meanings discussed below.

"Alkyl" refers to a saturated aliphatic hydrocarbon group including $C_1$-$C_{20}$ straight chain and branched chain groups. Preferably an alkyl group is an alkyl having 1 to 10 carbon atoms, more preferably having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chains thereof. More preferably an alkyl group is a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, preferably the substituent group(s) is one or more groups independently selected from the group consisting of alkyl, alkenyl, alkynyl, alkoxy, alkylsulfo, alkylamino, halogen, thiol, hydroxyl, nitro, cyano, cycloalkyl, heterocycloalkyl, aryl, heteroaryl, cycloalkoxy, heterocylic alkoxy, cycloalkylthio, heterocylic alkylthio, carbonyl, —C(O)OR$^5$, —OC(O)R$^5$, —C(O)R$^5$, —NHC(O)R$^5$, —NR$^6$R$^7$, and —S(O)$_m$R$^5$.

"Cycloalkyl" refers to saturated or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Representative examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes a cycloalkyl having a spiroling, fused ring, and bridged ring.

"Spiro Cycloalkyl" refers to a 5 to 20 membered polycyclic hydrocarbon group with rings connected through one common carbon atoms (called a spiro atom), wherein one or more rings can contain one or more double bonds, but none of the rings has a completely conjugated pi-electron system. Preferably a spiro cycloalkyl is 6 to 14 membered, more preferably 7 to 10 membered. According to the number of common spiro atoms, spiro cycloalkyl is divided into mono-spiro cycloalkyl, di-spiro cycloalkyl, or poly-spiro cycloalkyl, preferably refers to mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Representative examples of spiro cycloalkyl include, but are not limited to the following groups:

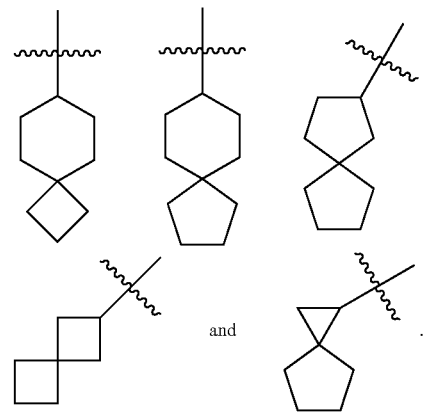

"Fused Cycloalkyl" refers to a 5 to 20 membered polycyclic hydrocarbon group, wherein each ring in the system shares an adjacent pair of carbon atoms with another ring, wherein one or more rings may contain one or more double bonds, but none of the rings has a completely conjugated pi-electron system. Preferably a fused cycloalkyl group is 6 to 14 membered, more preferably 7 to 10 membered. According to the number of membered rings, fused cycloalkyl is divided into bicyclic, tricyclic, tetracyclic, or polycyclic fused cycloalkyl, preferably refers to bicyclic or tricyclic fused cycloalkyl, more preferably 5-membered/5-membered, or 5-membered/6-membered bicyclic fused cycloalkyl. Representative examples of fused cycloalkyl include, but are not limited to the following groups:

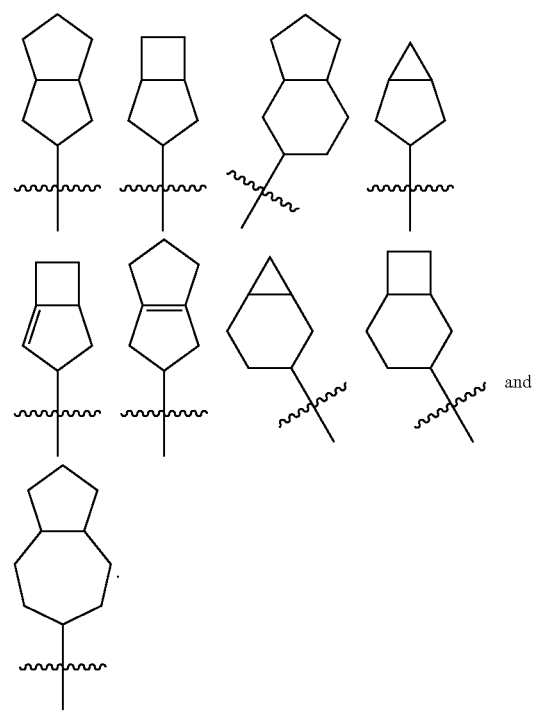

"Bridged Cycloalkyl" refers to a 5 to 20 membered polycyclic hydrocarbon group, wherein every two rings in the system share two disconnected carbon atoms. The rings can have one or more double bonds, but have no completely conjugated pi-electron system. Preferably a bridged cycloalkyl is 6 to 14 membered, more preferably 7 to 10 membered. According to the number of membered rings, bridged cycloalkyl is divided into bicyclic, tricyclic, tetracyclic, or polycyclic bridged cycloalkyl, preferably refers to bicyclic, tricyclic, or tetracyclic bridged cycloalkyl, more preferably bicyclic or tricyclic bridged cycloalkyl. Representative examples of bridged cycloalkyl include, but are not limited to the following groups:

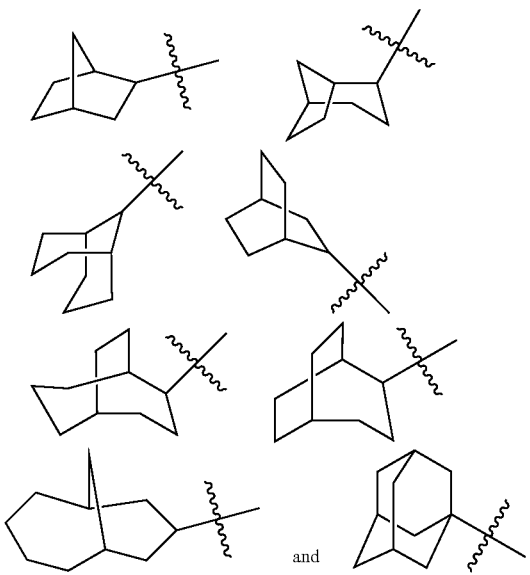

The cycloalkyl can be fused to aryl, heteroaryl, or the ring of a heterocycloalkyl, wherein the ring bound to the parent structure is cycloalkyl.

Representative examples include, but are not limited to indanylacetic, tetrahydronaphthalene, benzocycloheptyl and so on. Said cycloalkyl can be optionally substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxyl, nitro, cyano, cycloalkyl, heterocycloalkyl, aryl, heteroaryl, cycloalkoxy, heterocylic alkoxy, cycloalkylthio, heterocylic alkylthio, carbonyl, —C(O)OR$^5$, —OC(O)R$^5$, —C(O)R$^5$, —NHC(O)R$^5$, —NR$^6$R$^7$, and —S(O)$_m$R$^5$.

"Heterocyclyl" refers to a 3 to 20 membered saturated or partially unsaturated monocyclic or polycyclic hydrocarbon group having one or more heteroatoms selected from the group consisting of N, O, and S(O)$_m$ (wherein m is an integer from 0 to 2) as ring atoms, but excluding —O—O—, —O—S— or —S—S— in the ring, the remaining ring atoms being C. Preferably, heterocyclyl is 3 to 12 membered having 1 to 4 heteroatoms; more preferably 3 to 10 membered; and most preferably 4 to 6 membered. Representative examples of monocyclic heterocyclyl include, but are not limited to, pyrrolidyl, piperidyl, piperazinyl, morpholinyl, sulfo-morpholinyl, homopiperazinyl, furyl, azetidinyl, and so on. Polycyclic heterocyclyl includes the heterocyclyl having spiroling, fused ring, and bridged ring.

"Spiro Heterocyclyl" refers to a 5 to 20 membered polycyclic heterocyclyl group with rings connected through one common carbon atom (called a spiro atom), wherein said rings have one or more heteroatoms selected from the group consisting of N, O, and S(O)$_m$ (wherein m is an integer from 0 to 2) as ring atoms, the remaining ring atoms being C, wherein one or more rings can contain one or more double bonds, but none of the rings has a completely conjugated pi-electron system. Preferably a spiro heterocyclyl is 6 to 14 membered, more preferably 7 to 10 membered. According to the number of common spiro atoms, spiro heterocyclyl is divided into mono-spiro heterocyclyl, di-spiro heterocyclyl, or poly-spiro heterocyclyl, preferably refers to mono-spiro heterocyclyl or di-spiro heterocyclyl, more preferably 4-membered/4-membered, 4-membered/5-membered, 4-membered/6-membered, 5-membered/5-membered, or 5-membered/6-membered mono-spiro heterocycloalkyl. Representative examples of spiro heterocyclyl include, but are not limited to the following groups:

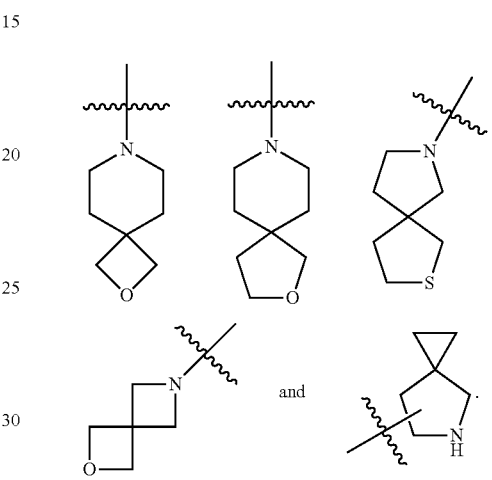

"Fused Heterocyclyl" refers to a 5 to 20 membered polycyclic heterocyclyl group, wherein each ring in the system shares an adjacent pair of carbon atoms with another ring, wherein one or more rings can contain one or more double bonds, but none of the rings has a completely conjugated pi-electron system, and wherein said rings have one or more heteroatoms selected from the group consisting of N, O, and S(O)$_m$, (wherein m is an integer from 0 to 2) as ring atoms, the remaining ring atoms being C. Preferably a fused heterocyclyl is 6 to 14 membered, more preferably 7 to 10 membered. According to the number of membered rings, fused heterocyclyl is divided into bicyclic, tricyclic, tetracyclic, or polycyclic fused heterocyclyl, preferably refers to bicyclic or tricyclic fused heterocyclyl, more preferably 5-membered/5-membered, or 5-membered/6-membered bicyclic fused heterocyclyl. Representative examples of fused heterocyclyl include, but are not limited to the following groups:

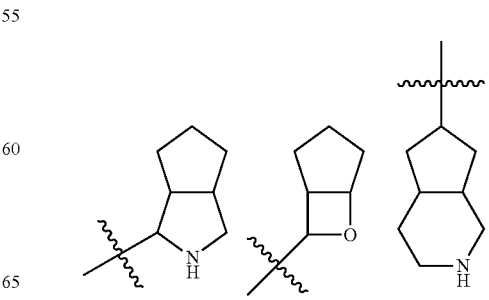

-continued

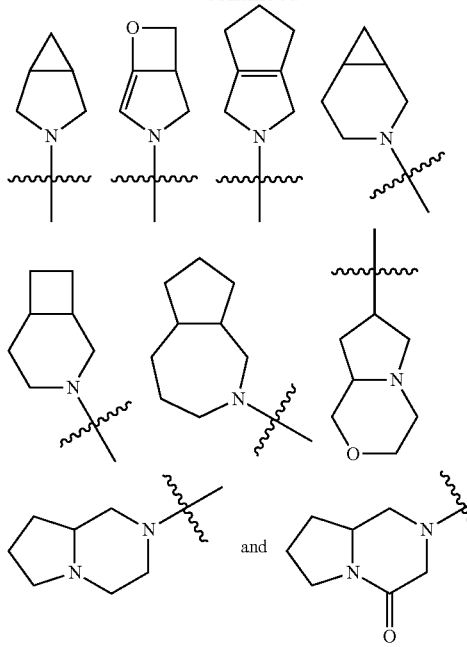

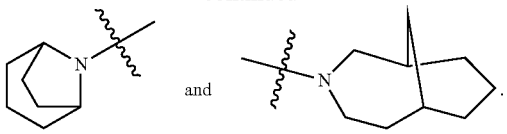

The ring of the heterocyclyl can be fused to an aryl, heteroaryl, or cycloalkyl, wherein the ring bound to the parent structure is heterocyclyl. Representative examples include, but are not limited to the following groups:

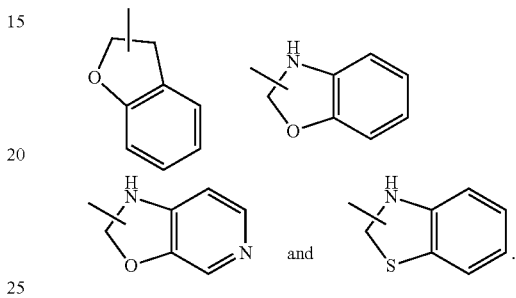

The heterocyclyl may be optionally substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxyl, nitro, cyano, cycloalkyl, heterocycloalkyl, aryl, heteroaryl, cycloalkoxy, heterocylic alkoxy, cycloalkylthio, heterocylic alkylthio, carbonyl, —C(O)OR$^5$, —OC(O)R$^5$, —C(O)R$^5$, —NHC(O)R$^5$, —NR$^6$R$^7$, and —S(O)$_m$R$^5$.

"Cycloalkylidene" refers to a saturated or partially unsaturated monocyclic or polycyclic hydrocarbon from which two hydrogen are formally eliminated, having 3 to 20 carbon atoms, preferably 3 to 12 carbon atoms, more preferably a monocyclic cycloalkylidene having 3 to 10 carbon atoms, most preferably 3 to 6 carbon atoms. Representative examples of monocyclic cycloalkylidene include, but not limited to, cyclopropylidene, cyclobutylidene, cyclopentylidene, cyclohexylidene, cycloheptylidene, cyclooctylidene, 1,2-cyclopropylidene, 1,3-cyclobutylidene, 1,4-cyclohexylidene, etc. Polycyclic cycloalkylidene includes spiro, fused and bridged cycloalkylidene.

"Aryl" refers to a 6 to 14 membered all-carbon monocyclic ring or a polycyclic fused ring (a "fused" ring system means that each ring in the system shares an adjacent pair of carbon atoms with other ring in the system) group, and has a completely conjugated pi-electron system. Preferably aryl is 6 to 10 membered, such as phenyl and naphthyl, most preferably, phenyl. The aryl can be fused to a heteroaryl, heterocyclyl or cycloalkyl, wherein the ring bound to the parent structure is aryl. Representative examples include, but are not limited to the following groups:

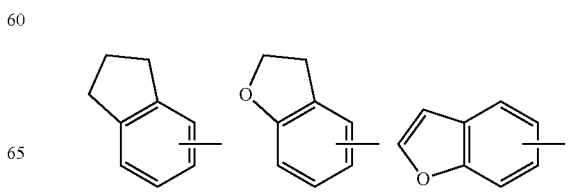

"Bridged Heterocyclyl" refers to a 5 to 14 membered polycyclic heterocyclyl group, wherein every two rings in the system share two disconnected carbon atoms, said rings could have one or more double bonds, but have no completely conjugated pi-electron system, and said rings have one or more heteroatoms selected from the group consisting of N, O, and S(O)$_m$ (wherein m is an integer from 0 to 2) as ring atoms, the remaining ring atoms being C. Preferably a bridged heterocyclyl is 6 to 14 membered, more preferably 7 to 10 membered. According to the number of membered rings, bridged heterocyclyl is divided into bicyclic, tricyclic, tetracyclic or polycyclic bridged heterocyclyl, preferably refers to bicyclic, tricyclic or tetracyclic bridged heterocyclyl, more preferably bicyclic or tricyclic bridged heterocyclyl. Representative examples of bridged heterocyclyl include, but are not limited to the following groups:

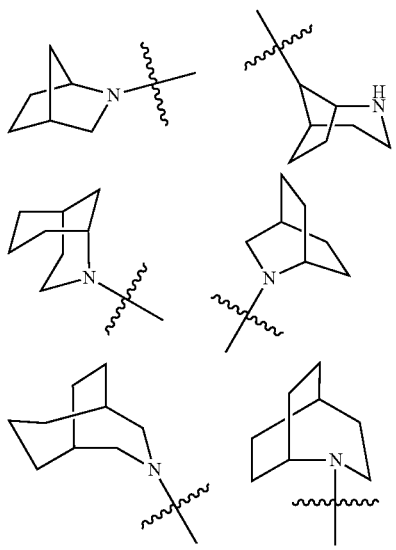

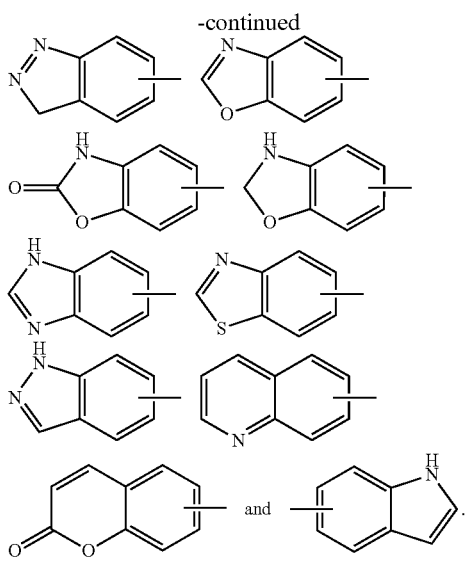

The aryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxyl, nitro, cyano, cycloalkyl, hetero cycloalkyl, aryl, heteroaryl, cycloalkoxy, heterocylic alkoxy, cycloalkylthio, heterocylic alkylthio, —C(O)OR$^5$, —OC(O)R$^5$, —C(O)R$^5$, —NHC(O)R$^5$, —NR$^6$R$^7$, and —S(O)$_m$R$^5$.

"Heteroaryl" refers to a heteroaryl having 1 to 4 heteroatoms selected from the group consisting of N, O, and S as ring atoms, and having 5 to 14 annular atoms, preferably 5- to 10-membered ring, and more preferably 5- or 6-membered ring. Examples include furyl, thienyl, pyridyl, pyrrolyl, N-alkyl pyrrolyl, pyrimidinyl, pyrazinyl, imidazolyl, tetrazolyl, and the like. The heteroaryl can be fused with the ring of an aryl, heterocyclyl, or cycloalkyl, wherein the ring bound to the parent structure is a heteroaryl ring. Representative examples include, but are not limited to the following groups,

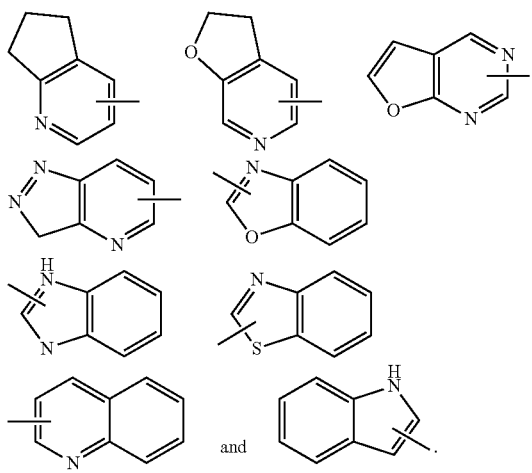

The heteroaryl group can be optionally substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxyl, nitro, cyano, cycloalkyl, heterocycloalkyl, aryl, heteroaryl, cycloalkoxy, heterocylic alkoxy, cycloalkylthio, heterocylic alkylthio, —C(O)OR$^5$, —OC(O)R$^5$, —C(O)R$^5$, —NHC(O)R$^5$, —NR$^6$R$^7$, and —S(O)$_m$R$^5$.

"Alkoxy" refers to both an —O-(alkyl) and an —O-(unsubstituted cycloalkyl) group, wherein the alkyl is as defined above. Representative examples include, but are not limited to, methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylsulfo, alkylamino, halogen, thiol, hydroxyl, nitro, cyano, cycloalkyl, heterocloalkyl, aryl, heteroaryl, cycloalkoxy, heterocylic alkoxy, cycloalkylthio, heterocylic alkylthio, —C(O)OR$^5$, —OC(O)R$^5$, —C(O)R$^5$, —NHC(O)R$^5$, —NR$^6$R$^7$, and —S(O)$_m$R$^5$.

"Haloalkyl" refers to an alkyl substituted with one or more halogen, wherein the alkyl is as defined above.

"Hydroxy" refers to an —OH group.

"Hydroxyalkyl" refers to an alkyl group substituted with a hydroxyl group, wherein the alkyl is as defined above.

"Halogen" refers to fluoro, chloro, bromo or iodo.

"Amino" refers to a —NH$_2$ group.

"Cyano" refers to a —CN group.

"Nitro" refers to a —NO$_2$ group.

"Benzyl" refers to a —CH$_2$— (phenyl) group.

"Carbonyl" refers to =O.

"Carboxyl" refers to a —C(O)OH group.

"Alkoxycarbonyl" refers to a —C(O)O(alkyl) or (cycloalkyl) group, wherein the alkyl and cycloalkyl are as defined above.

"Optional" and "optionally" mean that the event or circumstance described subsequently can, but need not occur, and the description includes instances in which the event or circumstance may or may not occur. For example, "the heterocyclic group optionally substituted by an alkyl" means that an alkyl group can be, but need not be present, and the description includes the case of the heterocyclic group being substituted with an alkyl and the heterocyclic group not being substituted with an alkyl.

"Substituted" refers to one or more hydrogen atoms in the group, preferably up to 5, more preferably 1 to 3 hydrogen atoms independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxyl group having free hydrogen and carbon atoms having unsaturated bonds (such as olefinic) may be unstable.

A "pharmaceutical composition" refers to a mixture of one or more of the compounds described herein or physiologically/pharmaceutically acceptable salts or prodrugs thereof, and other chemical components such as physiologically/pharmaceutically acceptable carriers and excipients. The purpose of a pharmaceutical composition is to facilitate administration of a compound to an organism, which is conducive to the absorption of the active ingredient and thus displaying biologically activity.

m and R$^5$~R$^7$ are as defined in formula (I).

Synthesis Method of the Compound of the Present Invention

In order to complete the purpose of the invention, the invention applies the following technical solution:

A preparation process of the compounds of formula (I), or tautomers, racemates, enantiomers, diastereomers, or mixtures thereof, or pharmaceutically acceptable salts thereof of the invention, comprising the following schemes:

The solvent includes, but is not limited to, acetic acid, methanol, ethanol, acetonitrile, tetrahydrofuran, dichloromethane, dimethyl sulfoxide, 1,4-dioxane, water, and N,N-dimethylformamide.

Scheme 1:

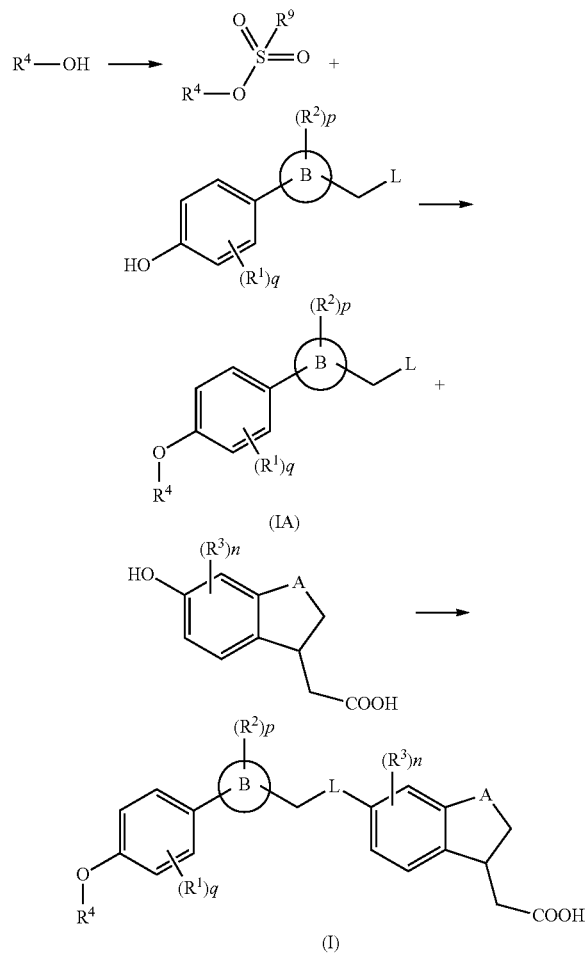

Scheme 2:

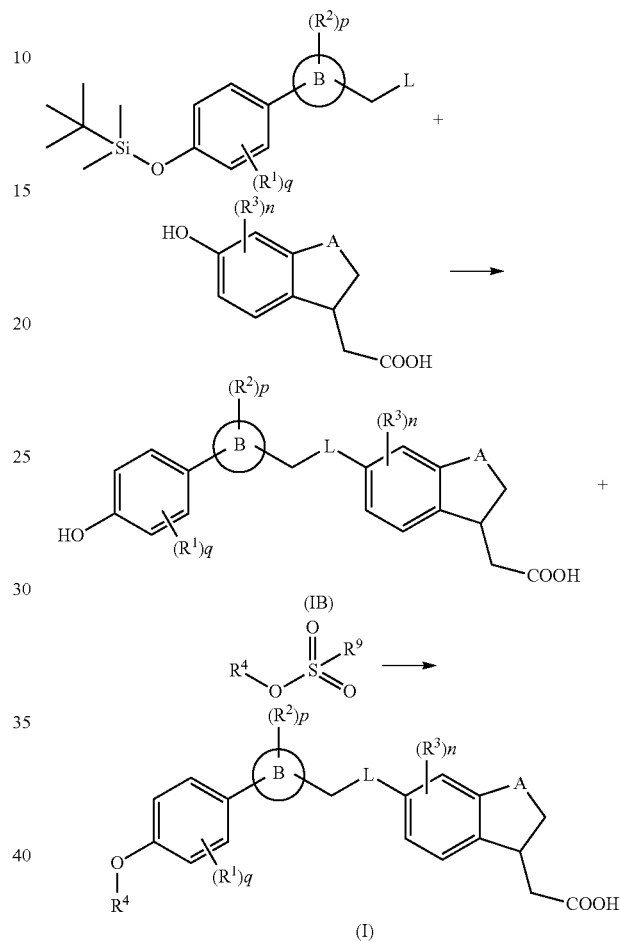

Reacting $R^4$-substituted hydroxyl compound with alkyl sulfonyl halide (preferably methanesulfonyl chloride) under alkaline conditions to obtain an $R^4$-substituted alkyl sulfonate; heating the $R^4$-substituted alkyl sulfonate with a hydroxyl-substituted phenyl compound in a solvent in the presence of cesium carbonate to obtain a compound of formula (IA); condensing the compound of formula (IA) with a hydroxyl-substituted benzocyclic compound in a solvent in the presence of triphenylphosphine and diisopropyl azodicarboxylate to obtain a compound of formula (I);

wherein ring B, L, A, $R^1$ to $R^4$, n, p, and q are as defined in formula (I), and $R^9$ is alkyl, preferably methyl.

The alkaline conditions include organic alkali and inorganic alkali, wherein the organic alkali includes, but is not limited to, triethylamine, N,N-diisopropylethylamine, N,N-dimethylformamide, n-butyllithium, potassium tert-butoxide, tetrabutyl ammonium bromide, preferably triethylamine; wherein the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, sodium hydroxide, or potassium hydroxide.

Condensing an alkylsiloxy-substituted phenyl compound with a hydroxyl-substituted benzocyclic compound in a solvent in the presence of triphenylphosphine and diisopropyl azodicarboxylate followed by deprotection to obtain a compound of formula (IB); heating the compound of formula (IB) with an $R^4$-substituted alkyl sulfonate (preferably $R^4$-substituted methanesulfonate) in a solvent in the presence of cesium carbonate to obtain a compound of formula (I);

wherein ring B, L, A, $R^1$ to $R^4$, n, p, and q are as defined above, and $R^9$ is alkyl, preferably methyl.

The alkaline conditions include organic alkali and inorganic alkali, wherein the organic alkali includes, but is not limited to, triethylamine, N,N-diisopropylethylamine, N,N-dimethylformamide, n-butyllithium, potassium tert-butoxide, tetrabutyl ammonium bromide, preferably triethylamine, wherein the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, sodium hydroxide, or potassium hydroxide.

The solvent includes, but is not limited to, acetic acid, methanol, ethanol, acetonitrile, tetrahydrofuran, dichloromethane, dimethyl sulfoxide, 1,4-dioxane, water, and N,N-dimethylformamide.

Scheme 3:

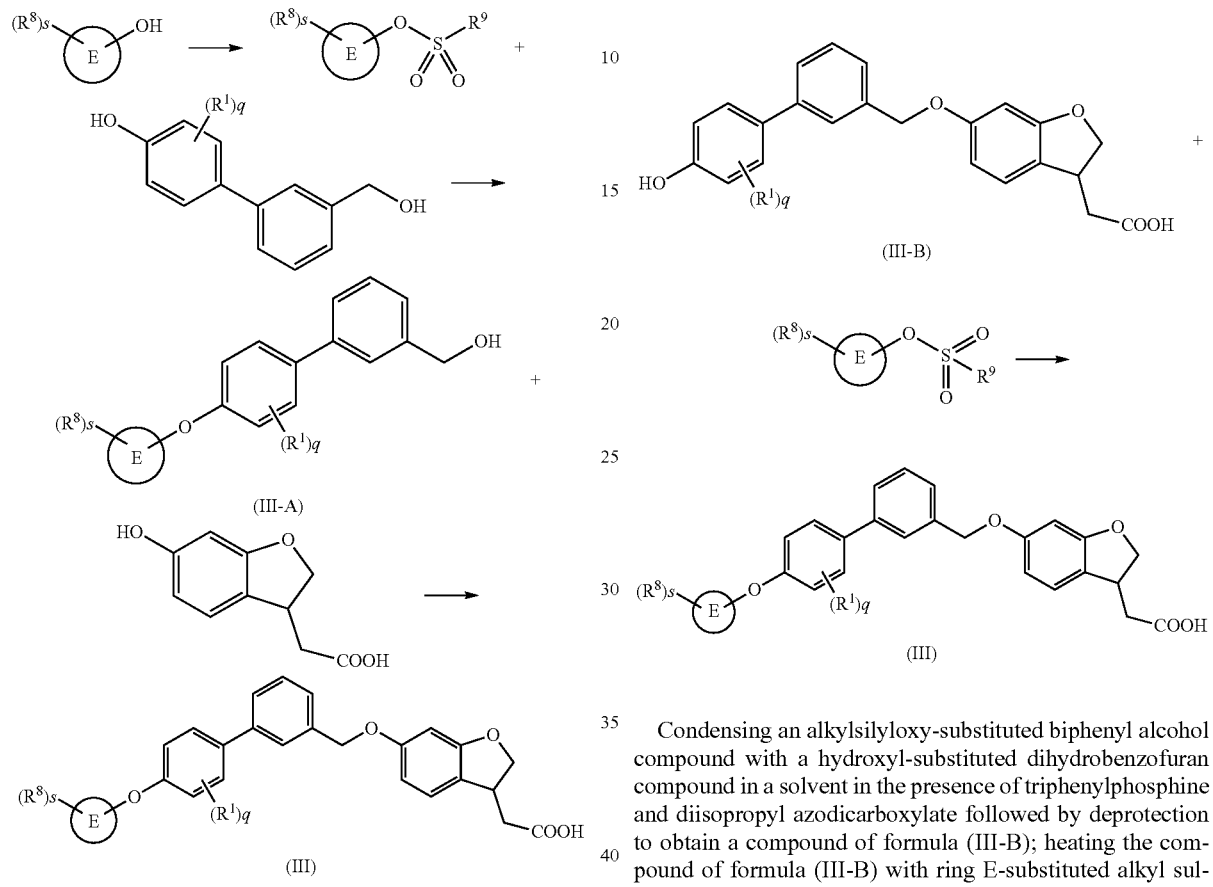

Reacting a ring E hydroxyl-substituted compound with an alkyl sulfonyl halide (preferably methanesulfonyl chloride) under alkaline conditions in a solvent to obtain an alkyl sulfonate substituted ring E; heating the alkyl sulfonte substituted ring E in a solvent with a hydroxyl-substituted biphenyl alcohol compound in the presence of cesium carbonate to obtain a compound of formula (III-A); condensing the compound of formula (III-A) with a hydroxyl-substituted dihydrobenzofuran compound in a solvent in the presence of triphenylphosphine and diisopropyl azodicarboxylate to obtain a compound of formula (III);

wherein ring E, $R^1$, $R^8$, s, and q are as defined in formula (III), and $R^9$ is alkyl, preferably methyl.

Scheme 4:

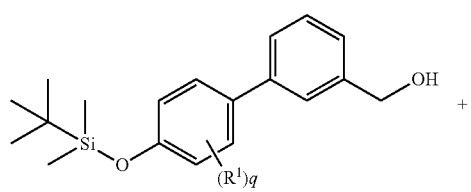

Condensing an alkylsilyloxy-substituted biphenyl alcohol compound with a hydroxyl-substituted dihydrobenzofuran compound in a solvent in the presence of triphenylphosphine and diisopropyl azodicarboxylate followed by deprotection to obtain a compound of formula (III-B); heating the compound of formula (III-B) with ring E-substituted alkyl sulfonate (preferably ring E-substituted methanesulfonate) in a solvent in the presence of cesium carbonate to obtain a compound of formula (III);

when $R^8$ is hydroxyl, the hydroxyl is optionally further protected by a protecting group, and then the protecting group is deprotected to obtain a compound of formula (III);

wherein ring E, $R^1$, $R^8$, s, and q are as defined in formula (III), and $R^9$ is alkyl, preferably methyl.

The alkaline conditions include organic alkali and inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide, preferably triethylamine, wherein the inorganic alkali includes, but is not limited to, sodium hydride, sodium hydroxide, potassium hydroxide, sodium carbonate, sodium bicarbonate, potassium carbonate, potassium bicarbonate and cesium carbonate, preferably sodium carbonate, potassium carbonate, sodium hydroxide, or potassium hydroxide.

The solvent includes, but is not limited to, acetic acid, methanol, ethanol, acetonitrile, tetrahydrofuran, dichloromethane, dimethyl sulfoxide, 1,4-dioxane, water and N,N-dimethylformamide.

Scheme 5:

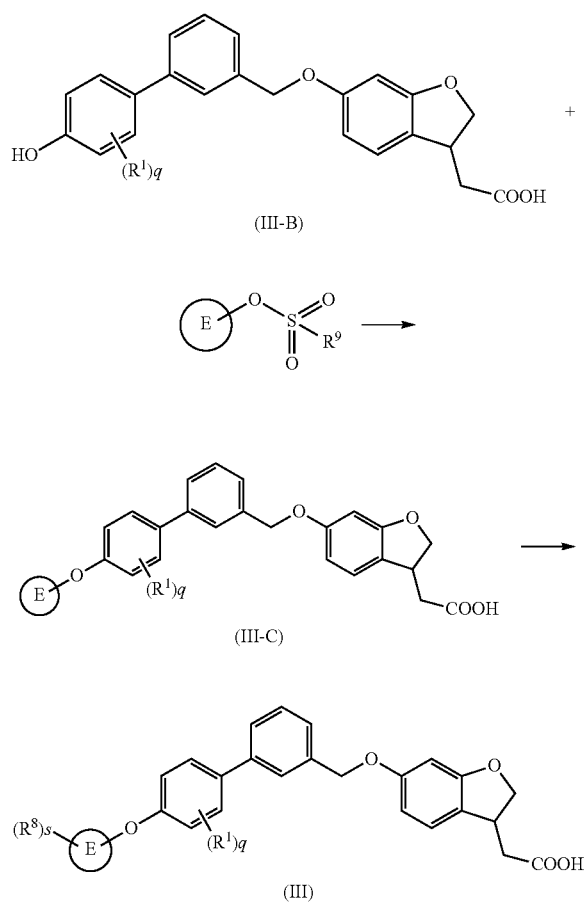

Heating a compound of formula (III-B) and ring E-substituted alkyl sulfonate (preferably ring E-substituted methanesulfonate) in a solvent in the presence of cesium carbonate to obtain a compound of formula (III-C); reacting the compound of formula (III-C) with substituted $R^8$ (preferably sulfonyl chloride or anhydride) to obtain a compound of formula (III);

wherein ring E, $R^1$, $R^8$, s, and q are as defined in formula (III).

The alkaline condition includes organic alkali and inorganic alkali, wherein the organic alkali includes, but is not limited to, triethylamine, N,N-diisopropylethylamine, N,N-dimethylformamide, n-butyllithium, potassium tert-butoxide, tetrabutyl ammonium bromide, preferably triethylamine, wherein the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, sodium hydroxide, or potassium hydroxide.

The solvent includes, but is not limited to, acetic acid, methanol, ethanol, acetonitrile, tetrahydrofuran, dichloromethane, dimethyl sulfoxide, 1,4-dioxane, water, and N,N-dimethylfomamide.

Preferred Embodiments

The following examples serve to illustrate the invention, but the examples should not be considered as limiting the scope of the invention.

EXAMPLES

Compound structures were identified by NMR or MS. NMR was determined by a Bruker AVANCE-400 machine. The solvents were deuterated-dimethyl sulfoxide (DMSO-$d_6$), deuterated-chloroform (CDCl$_3$) and deuterated-methanol (CD$_3$OD) with tetramethylsilane (TMS) as an internal standard. NMR chemical shifts (δ) were given in $10^{-6}$ (ppm).

MS was determined by a FINNIGAN LCQAd (ESI) mass spectrometer (manufacturer: Thermo, type: Finnigan LCQ advantage MAX). HPLC was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4 6 mm chromatographic column)

The average inhibition rate of kinase and IC$_{50}$ were determined by a NovoStar ELISA (BMG Co., Germany).

For thin-layer silica gel chromatography (TLC) Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as carrier. The known starting material of the invention can be prepared by conventional synthesis methods in the prior art, or can be purchased from ABCR GmbH & Co. KG, Acros Organics, Aldrich Chemical Company, Accela ChemBio Inc., or Dari chemical Company, etc.

Unless otherwise stated, the following reactions were placed under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressured hydrogenation reactions were performed with a Parr 3916EKX hydrogenation spectrometer and a QL-500 hydrogen generator.

In hydrogenation reactions, the reaction system was generally vacuumed and filled with hydrogen, with the above operation repeated three times.

Microwave reactions were performed with a CEM Discover-S 908860 microwave reactor.

Unless otherwise stated, the solution used in the following reactions refers to an aqueous solution.

Unless otherwise stated, the reaction temperature in the following reactions was room temperature, and the range of the temperature was 20° C.-30° C.

The reaction process was monitored by thin layer chromatography (TLC), the system of developing solvent included: A: dichloromethane and methanol, B: n-hexane and ethyl acetate, C: petroleum ether and ethyl acetate, D: acetone. The ratio of the volume of the solvent was adjusted according to the polarity of the compounds.

The elution system for purification of the compounds by column chromatography and thin layer chromatography included: A: dichloromethane and methanol system, B: n-hexane and ethyl acetate system, C: n-hexane and acetone, D: n-hexane, E: ethyl acetate. The volume of the solvent was adjusted according to the polarity of the compounds, and sometimes a little alkaline reagent such as triethylamine or acidic reagent was also added.

Example 1

2-((S)-6-((2',6'-Dimethyl-4'-(((S)-tetrahydrofuran-3-yl)oxy)biphenyl-3-yl)methoxy)-2,3-dihydrobenzofuran-3-yl)acetic acid

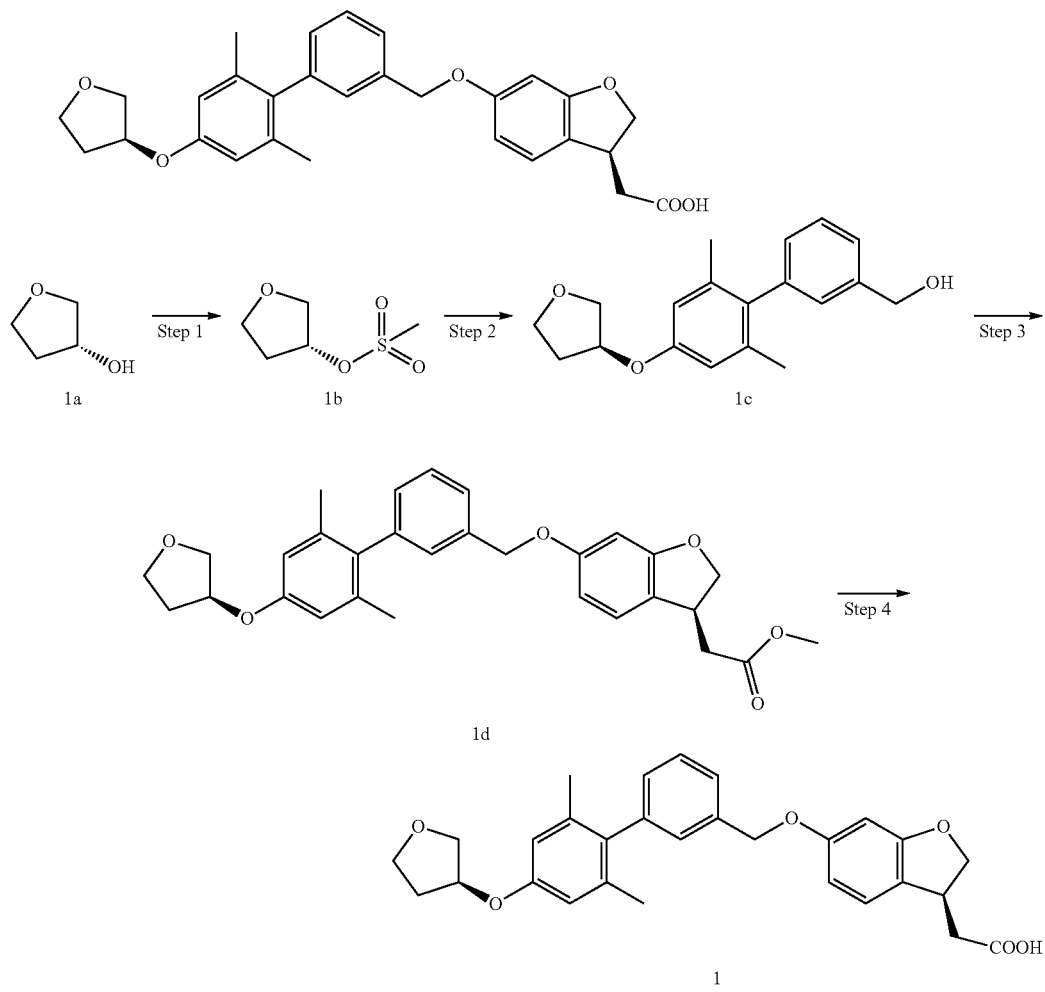

Step 1

(R)-Tetrahydrofuran-3-yl methanesulfonate

(R)-Tetrahydrofuran-3-ol 1a (300 mg, 3.40 mmol) and triethylamine (687 mg, 6.80 mmol) were dissolved in 20 mL of dichloromethane in an ice bath, followed by addition of methanesulfonyl chloride (468 mg, 4.10 mmol). The reaction solution was warmed up to room temperature and stirred for 2 hours. The reaction solution was mixed with 10 mL of dichloromethane, washed with water (30 mL×3), dried with anhydrous magnesium sulphate, and filtered. The filtrate was concentrated under reduced pressure to obtain the title compound (R)-tetrahydrofuran-3-yl methanesulfonate 1b (520 mg) as a yellow oil, which was directly used in the next step without further purification.

Step 2

(S)-(2',6'-Dimethyl-4'-((tetrahydrofuran-3-yl)oxy)biphenyl-3-yl)methanol

The crude (R)-tetrahydrofuran-3-yl methanesulfonate 1b (520 mg, 3.13 mmol), 3'-(hydroxymethyl)-2,6-dimethylbiphenyl-4-ol (714 mg, 3.13 mmol, prepared by a method disclosed in Chinese patent application CN101616913) and cesium carbonate (3.10 g, 9.39 mmol) were dissolved in 30 mL of N,N-dimethylformamide. The reaction mixture was heated to 80° C. and stirred for 7 hours. The resulting solution was concentrated under reduced pressure. The residue was purified by silica gel column chromatography with elution system B to obtain the title compound (S)-(2',6'-dimethyl-4'-((tetrahydrofuran-3-yl)oxy)biphenyl-3-yl)methanol 1c (500 mg, yield 54.0%) as a colorless oil.

MS m/z (ESI): 299.3 [M+1]

Step 3

Methyl 2-((S)-6-((2',6'-dimethyl-4'-(((S)-tetrahydrofuran-3-yl)oxy)biphenyl-3-yl)methoxy)-2,3-dihydrobenzofuran-3-yl)acetate (S)-(2',6'-Dimethyl-4'-((tetrahydrofuran-3-yl)oxy)biphenyl-3-yl)methanol1c (143 mg, 0.48 mmol), methyl (S)-2-(6-hydroxyl-2,3-dihydrobenzofuran-3-yl)acetate (100 mg, 0.48 mmol, prepared by a method disclosed in Chinese patent application CN101616913, the racemate was resolved by chiral HPLC using HPLC method with separation condition: chiral column Chiralpak IA, mobile phase: n-hexane:tetrahydrofuran=80:20, flow rate: 1.0 mL/minute, and the corresponding component was collected and rotary evaporated to remove the solvent), and triphenylphosphine (189 mg, 0.72 mmol) were dissolved in 20 mL of dichloromethane. The reaction solution was cooled down to 0° C., followed by addition of diisopropyl azodicarboxylate (146 mg, 0.72 mmol), then warmed up to room temperature and stirred for 2 hours. The resulting solution was concentrated under reduced pressure. The residue was purified by silica gel column chromatography with elution system B to obtain the title compound methyl 2-((S)-6-((2',6'-dimethyl-4'-(((S)-tetrahydrofuran-3-yl)oxy)biphenyl-3-yl)methoxy)-2,3-dihydrobenzofuran-3-yl)acetate 1d (220 mg, yield 94.0%) as a white solid.

MS m/z (ESI): 489.4 [M+1]

Step 4

2-((S)-6-((2',6'-Dimethyl-4'-(((S)-tetrahydrofuran-3-yl)oxy)biphenyl-3-yl)methoxy)-2,3-dihydrobenzofuran-3-yl)acetic acid Methyl 2-((S)-6-((2',6'-Dimethyl-4'-(((S)-tetrahydrofuran-3-yl)oxy)biphenyl-3-yl)methoxy)-2,3-dihydrobenzofuran-3-yl)acetate 1d (220 mg, 0.45 mmol) was dissolved in 15 mL of methanol, followed by addition of 3 M aqueous sodium hydroxide solution (1.5 mL, 4.50 mmol). The reaction mixture was reacted for 3 hours. The mixture was concentrated under reduced pressure, mixed with 10 mL of water, and 1M hydrochloric acid was added dropwise to adjust the pH to 2. The resulting solution was extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound 2-((S)-6-((2',6'-dimethyl-4'-(((S)-tetrahydrofuran-3-yl)oxy)biphenyl-3-yl)methoxy)-2,3-dihydrobenzofuran-3-yl)acetic acid 1 (210 mg, yield 100%) as a white solid.

MS m/z (ESI): 473.2 [M−1]

$^1$H NMR (400 MHz, CDCl$_3$) δ 7.45 (dt, 2H), 7.21 (s, 1H), 7.11 (dd, 2H), 6.66 (s, 2H), 6.58-6.46 (m, 2H), 5.10 (s, 2H), 5.04-4.94 (m, 1H), 4.80 (t, 1H), 4.33 (dd, 1H), 4.11-4.01 (m, 3H), 4.01-3.92 (m, 1H), 3.85 (ddd, 1H), 2.85 (dd, 1H), 2.66 (dd, 1H), 2.30-2.19 (m, 2H), 2.03 (s, 6H).

Example 2

2-((S)-6-((2',6'-Dimethyl-4'-(((R)-tetrahydrofuran-3-yl)oxy)biphenyl-3-yl)methoxy)-2,3-dihydrobenzofuran-3-yl)acetic acid

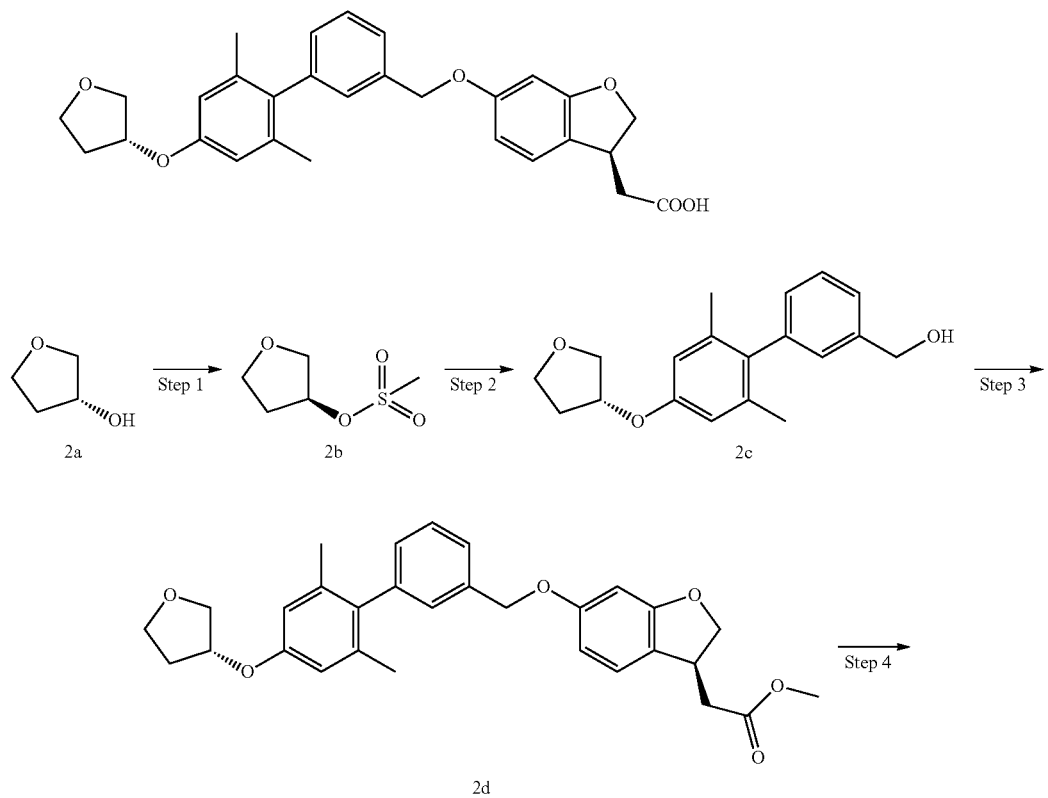

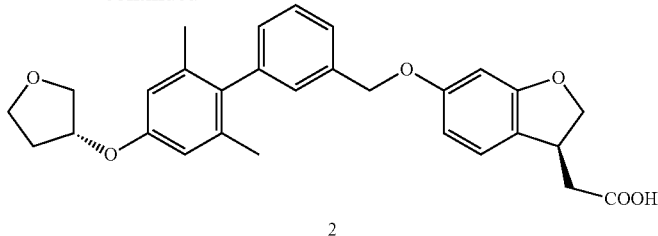

2

Step 1

(S)-Tetrahydrofuran-3-yl methanesulfonate (S)-Tetrahydrofuran-3-ol 2a (300 mg, 3.40 mmol) and triethylamine (687 mg, 6.80 mmol) were dissolved in 20 mL of dichloromethane in an ice bath, followed by addition of methanesulfonyl chloride (908 mg, 7.93 mmol). The reaction solution was warmed up to room temperature and stirred for 2 hours. The resulting solution was mixed with 10 mL of dichloromethane, washed with water (30 mL×2), dried with anhydrous magnesium sulphate, and filtered. The filtrate was concentrated under reduced pressure to obtain the crude title compound (S)-tetrahydrofuran-3-yl methanesulfonate 2b as a yellow oil (522 mg, yield 92.5%).

Step 2

(R)-(2',6'-Dimethyl-4'-((tetrahydrofuran-3-yl)oxy)biphenyl-3-yl)methanol

The crude (S)-tetrahydrofuran-3-yl methanesulfonate 2b (522 mg, 3.14 mmol), 3'-(hydroxymethyl)-2,6-dimethylbiphenyl-4-ol (714 mg, 3.13 mmol, prepared by a method disclosed in Chinese patent application CN101616913) and cesium carbonate (3.10 g, 9.39 mmol) were dissolved in 30 mL of N,N-dimethylformamide. The reaction mixture was heated to 80° C. and stirred for 12 hours. The resulting solution was concentrated under reduced pressure and the residue was purified by silica gel column chromatography with elution system B to obtain the title compound (R)-(2', 6'-dimethyl-4'-((tetrahydrofuran-3-yl)oxy)biphenyl-3-yl)methanol 2c (540 mg, yield 58.0%) as a colorless oil.

MS m/z (ESI): 299.2 [M+1]

Step 3

Methyl 2-((S)-6-((2',6'-dimethyl-4'-(((R)-tetrahydrofuran-3-yl)oxy)biphenyl-3-yl)methoxy)-2,3-dihydrobenzofuran-3-yl)acetate (R)-(2',6'-Dimethyl-4'-((tetrahydrofuran-3-yl)oxy)biphenyl-3-yl)methanol 2c (143 mg, 0.48 mmol), methyl (S)-2-(6-hydroxyl-2,3-dihydrobenzofuran-3-yl)acetate (100 mg, 0.48 mmol) and triphenylphosphine (189 mg, 0.72 mmol) were dissolved in 20 mL of dichloromethane. The reaction solution was cooled down to 0° C., followed by addition of diisopropyl azodicarboxylate (146 mg, 0.72 mmol). The reaction solution was warmed up to room temperature and stirred for 12 hours. The resulting solution was concentrated under reduced pressure and the residue was purified by silica gel column chromatography with elution system B to obtain the title compound methyl 2-((S)-6-((2',6'-dimethyl-4'-(((R)-tetrahydrofuran-3-yl)oxy)biphenyl-3-yl)methoxy)-2,3-dihydrobenzofuran-3-yl)acetate 2d (201 mg, yield 85.9%) as a colorless oil.

MS m/z (ESI): 489.4 [M+1]

Step 4

2-((S)-6-((2',6'-Dimethyl-4'(((R)-tetrahydrofuran-3-yl)oxy)biphenyl-3-yl)methoxy)-2,3-dihydrobenzofuran-3-yl)acetic acid Methyl 2-((S)-6-((2',6'-dimethyl-4'-(((R)-tetrahydrofuran-3-yl)oxy)biphenyl-3-yl)methoxy)-2,3-dihydrobenzofuran-3-yl)acetate 2d (201 mg, 0.41 mmol) was dissolved in 15 mL of methanol. The reaction solution was added with 2M aqueous sodium hydroxide solution (2 mL, 4.10 mmol) and stirred for 3 hours. The resulting solution was concentrated under reduced pressure, mixed with 10 mL of water, and 1M hydrochloric acid was added dropwise to adjust the pH to 2-3. The solution was extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound 2-((S)-6-((2',6'-dimethyl-4'-(((R)-tetrahydrofuran-3-yl)oxy)biphenyl-3-yl)methoxy)-2,3-dihydrobenzofuran-3-yl)acetic acid 2 (150 mg, yield 77.1%) as a white solid.

MS m/z (ESI): 473.4 [M-1]

$^1$H NMR (400 MHz, CDCl$_3$) δ 7.45 (dt, 2H), 7.21 (s, 1H), 7.11 (dd, 2H), 6.66 (s, 2H), 6.58-6.48 (m, 2H), 5.10 (s, 2H), 5.04-4.94 (m, 1H), 4.80 (t, 1H), 4.33 (dd, 1H), 4.11-4.01 (m, 3H), 4.00-3.91 (m, 1H), 3.86 (dd, 1H), 2.85 (dd, 1H), 2.66 (dd, 1H), 2.33-2.16 (m, 2H), 2.03 (s, 6H).

Example 3
(S)-2-(6-((4'-((1-(tert-Butoxycarbonyl)piperidin-4-yl)oxy)-2',6'-dimethylbiphenyl-3-yl)methoxy)-2,3-dihydrobenzofuran-3-yl)acetic acid
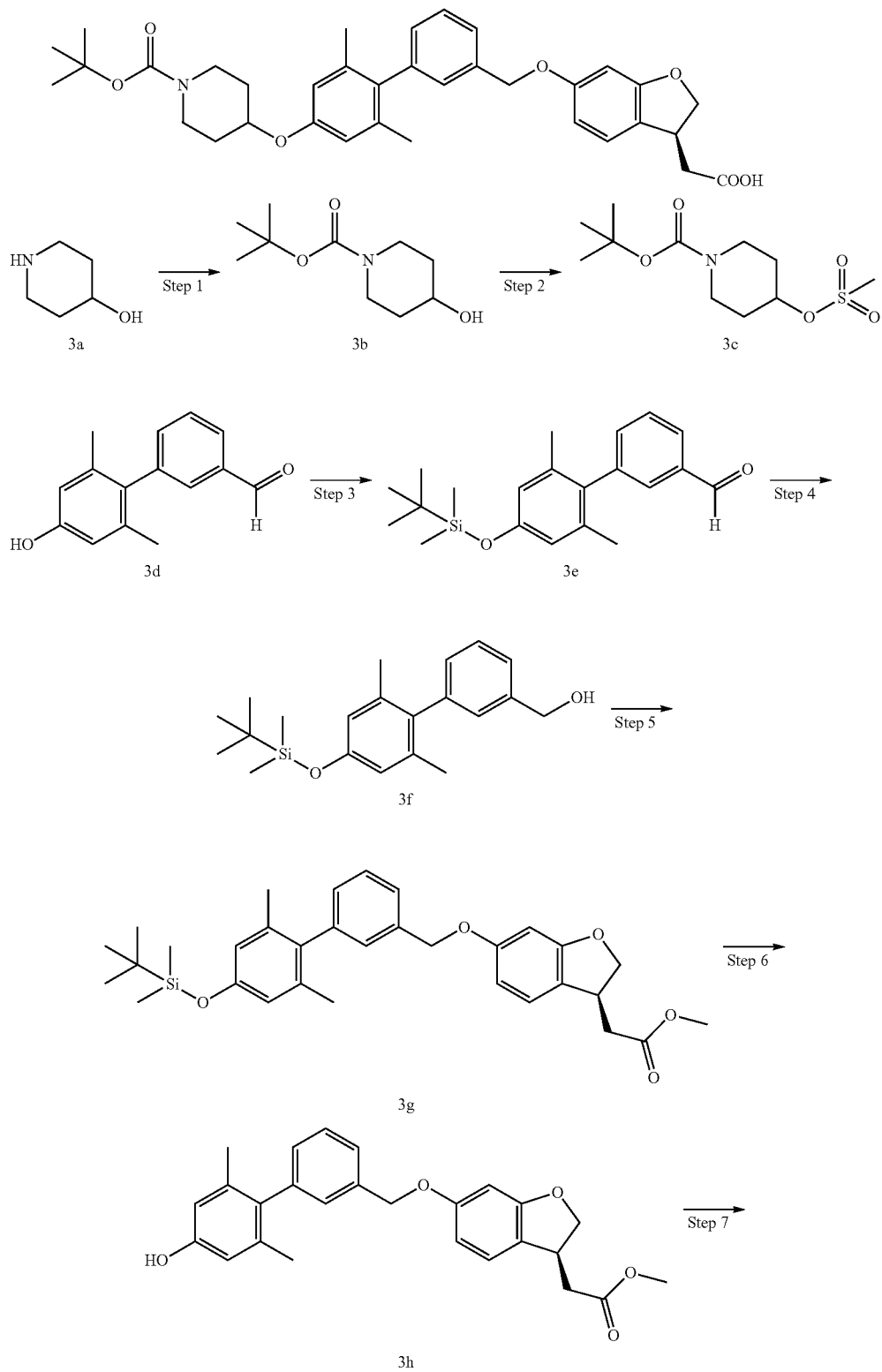

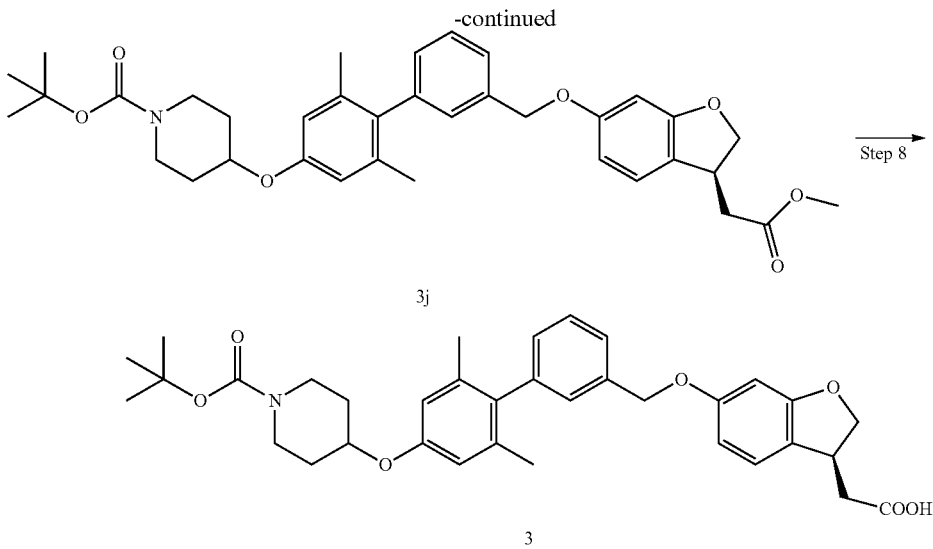

Step 1 tert-Butyl 4-hydroxypiperidine-1-carboxylate

4-Hydroxyl-piperidine 3a (1.01 g, 10 mmol) and triethylamine (2.02 g, 20 mmol) were dissolved in 20 mL of dichloromethane in an ice bath, followed by addition of di-tert-butyl dicarbonate (2.18 g, 10 mmol). The reaction mixture was warmed up to room temperature and stirred for 3 hours. The solution was washed with water (20 mL×2), dried with anhydrous sodium sulfate, and filtered. The filtrate was concentrated under reduced pressure to obtain the crude title compound tert-butyl 4-hydroxypiperidin-1-carboxylate 3b (2 g) as a colorless oil, which was directly used in the next step without further purification.

Step 2 tert-Butyl 4-((methylsulfonyl)oxy)piperidine-1-carboxylate

The crude tert-butyl 4-hydroxypiperidine-1-carboxylate 3b (2.01 g, 10 mmol) was dissolved in 30 mL of dichloromethane in an ice bath, followed by addition of triethylamine (2.02 g, 20 mmol) and methanesulfonyl chloride (1.26 g, 11 mmol). The reaction solution was warmed up to room temperature and stirred for 3 hours. The resulting solution was washed with water (20 mL×2), dried with anhydrous sodium sulfate, and filtered. The filtrate was concentrated under reduced pressure to obtain the crude title compound tert-butyl 4-((methylsulfonyl)oxy)piperidin-1-carboxylate 3c (2.20 g) as a light yellow solid, which was directly used in the next step without further purification.

Step 3

4'-((tert-Butyldimethylsilyl)oxy)-2',6'-dimethylbiphenyl-3-carbaldehyde

4'-Hydroxy-2',6'-dimethylbiphenyl-3-carbaldehyde 3d (7.20 g, 31.80 mmol, prepared by a method disclosed in Chinese patent application CN101616913), tert-butyldimethylsilyl chloride (5.27 g, 34.90 mmol), and imidazole (2.60 g, 38.10 mmol) were dissolved in 60 mL of N,N-dimethylformamide. The reaction solution was heated to 60° C. and stirred for 12 hours. The resulting solution was concentrated under reduced pressure, and the residue was purified by silica gel column chromatography with elution system B to obtain the title compound 4'-((tert-butyldimethylsilyl)oxy)-2',6'-dimethylbiphenyl-3-carbaldehyde 3e (10 g, yield 92.0%) as a brown oil.

MS m/z (ESI): 341.2 [M+1]

Step 4

(4'-((tert-Butyldimethylsilyl)oxy)-2',6'-dimethylbiphenyl-3-yl)methanol

4'-((tert-Butyldimethylsilyl)oxy)-2',6'-dimethylbiphenyl-3-carbaldehyde 3e (2.60 g, 38.10 mmol) was dissolved in 80 mL of methanol, followed by addition of sodium borohydride (1.66 g, 43.95 mmol). The reaction mixture was stirred for 3 hours. The resulting mixture was mixed with 50 mL of acetone and concentrated under reduced pressure. The residue was mixed with 200 mL of ethyl acetate, washed with water (60 mL×2), dried with anhydrous sodium sulfate, and filtered. The filtrate was concentrated under reduced pressure to obtain the crude title compound (4'-((tert-butyldimethylsilyl)oxy)-2',6'-dimethylbiphenyl-3-yl)methanol 3f (9.80 g, yield 98.0%) as a colorless oil.

MS m/z (ESI): 343.2 [M+1]

Step 5

(S)-Methyl 2-(6-((4'-((tert-butyldimethylsilyl)oxy)-2',6'-dimethylbiphenyl-3-yl)methoxy)-2,3-dihydrobenzofuran-3-yl)acetate (4'-((tert-Butyldimethylsilyl)oxy)-2',6'-dimethylbiphenyl-3-yl)methanol 3f (1.19 g, 3.48 mmol), methyl (S)-2-(6-hydroxyl-2,3-dihydrobenzofuran-3-yl)acetate (660 mg, 3.17 mmol) and triphenylphosphine (1.34 g, 4.75 mmol) were dissolved in 10 mL of dichloromethane. The reaction solution was cooled down to 0° C., followed by addition of diisopropyl azodicarboxylate (960 mg, 4.75 mmol), then warmed up to room temperature and stirred for 4 hours. The resulting solution was concentrated under reduced pressure, and the residue was purified by silica gel column chromatography with elution system B to obtain the title compound (S)-methyl 2-(6-((4'-((tert-butyldimethylsilyl)oxy)-2',6'-dimethylbiphenyl-3-yl)methoxy)-2,3-dihydrobenzofuran-3-yl)acetate 3 g (1.28 g, yield 76.0%) as a white solid.

MS m/z (ESI): 533.3 [M+1]

Step 6

(S)-methyl 2-(6-((4'-Hydroxy-2',6'-dimethylbiphenyl-3-yl)methoxy)-2,3-dihydrobenzofuran-3-yl)acetate (S)-Methyl 2-(6-((4'-((tert-butyldimethylsilyl)oxy)-2',6'-dimethylbiphenyl-3-yl)methoxy)-2,3-dihydrobenzofuran-3-yl)acetate 3 g (1.28 g, 2.40 mmol) was dissolved in 50 mL of tetrahydrofuran, followed by addition of 10 mL of 6 M hydrochloric acid. The reaction solution was stirred at room temperature for 12 hours. The resulting solution was concentrated under reduced pressure and the residue was mixed with 100 mL of ethyl acetate. The organic phase was washed with water (20 mL×2) and saturated sodium chloride solution (20 mL) successively, dried with anhydrous sodium sulfate, and filtered. The filtrate was concentrated under reduced pressure. The residue was mixed with 60 mL of methanol and 1 mL of concentrated sulfuric acid. The resulting solution was heated to 70° C. and stirred for 1.5 hours. The solution was concentrated under reduced pressure, mixed with 100 mL of ethyl acetate, washed with water (20 mL×2), dried with anhydrous sodium sulfate, and filtered. The filtrate was concentrated under reduced pressure, and the residue was purified by elution system B to obtain the title compound (S)-methyl 2-(6-((4'-hydroxy-2',6'-dimethylbiphenyl-3-yl)methoxy)-2,3-dihydrobenzofuran-3-yl)acetate 3 h (670 mg, yield 67.0%) as a colorless oil.

MS m/z (ESI): 419.2 [M+1]

Step 7

Methyl (S)-2-(6-((4'-((1-(tert-butoxycarbonyl)piperidin-4-yl)oxy)-2',6'-dimethylbiphenyl-3-yl)methoxy)-2,3-dihydrobenzofuran-3-yl)acetate 4-[(Methylsulfonyl)oxy]piperidine-1-carboxylic acid tert-butyl ester (134 mg, 0.48 mmol), (S)-methyl 2-(6-((4'-hydroxy-2',6'-dimethylbiphenyl-3-yl)methoxy)-2,3-dihydrobenzofuran-3-yl)acetate 3 h (200 mg, 0.48 mmol) and cesium carbonate (470 mg, 1.43 mmol) were dissolved in 10 mL of N,N-dimethylformamide. The reaction mixture was heated to 80° C. and stirred for 12 hours. The resulting solution was mixed with 30 mL of ethyl acetate. The organic phase was washed with water (20 mL×2) and saturated sodium chloride solution (20 mL) successively, dried with anhydrous sodium sulfate and filtered. The filtrate was concentrated under reduced pressure and the residue was purified by elution system B to obtain the title compound methyl (S)-2-(6-((4'-((1-(tert-butoxycarbonyl)piperidin-4-yl)oxy)-2',6'-dimethylbiphenyl-3-yl)methoxy)-2,3-dihydrobenzofuran-3-yl)acetate 3j (101 mg, yield 35.0%) as a colorless slime.

MS m/z (ESI): 502.3 [M−99]

Step 8

(S)-2-(6-((4'-((1-(tert-Butoxycarbonyl)piperidin-4-yl)oxy)-2',6'-dimethylbiphenyl-3-yl)methoxy)-2,3-dihydrobenzofuran-3-yl)acetic acid Methyl (S)-2-(6-((4'-((1-(tert-butoxycarbonyl)piperidin-4-yl)oxy)-2',6'-dimethylbiphenyl-3-yl)methoxy)-2,3-dihydrobenzofuran-3-yl)acetate 3j (26 mg, 0.04 mmol) was dissolved in 5 mL of methanol, followed by addition of 1M aqueous sodium hydroxide solution (0.5 mL, 0.43 mmol). The reaction solution was reacted for 1.5 hours. The solution was concentrated under reduced pressure, mixed with 3 mL of water, 1M citric acid was added dropwise to adjust the pH to 4-5, and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((4'-((1-(tert-butoxycarbonyl)piperidin-4-yl)oxy)-2',6'-dimethylbiphenyl-3-yl)methoxy)-2,3-dihydrobenzofuran-3-yl)acetic acid 3 (12 mg, yield 47.4%) as a white solid.

MS m/z (ESI): 586.3 [M−1]

$^1$H NMR (400 MHz, CDCl$_3$) δ 7.51-7.38 (m, 2H), 7.21 (s, 1H), 7.11 (dd, 2H), 6.70 (s, 2H), 6.51-6.54 (m, 2H), 5.10 (s, 2H), 4.80 (t, 1H), 4.52 (s, 1H), 4.33 (t, 1H), 3.76-3.85 (m, 3H), 3.41 (s, 2H), 2.85 (d, 1H), 2.66 (dd, 1H), 2.03 (s, 6H), 1.90 (d, 4H), 1.52 (s, 9H).

Example 4

(S)-2-(6-((2',6'-Dimethyl-4'-(piperidin-4-yloxy)biphenyl-3-yl)methoxy)-2,3-dihydrobenzofuran-3-yl)acetic acid

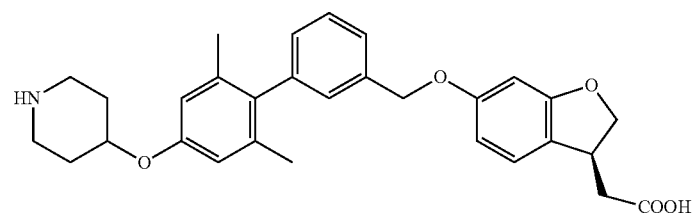

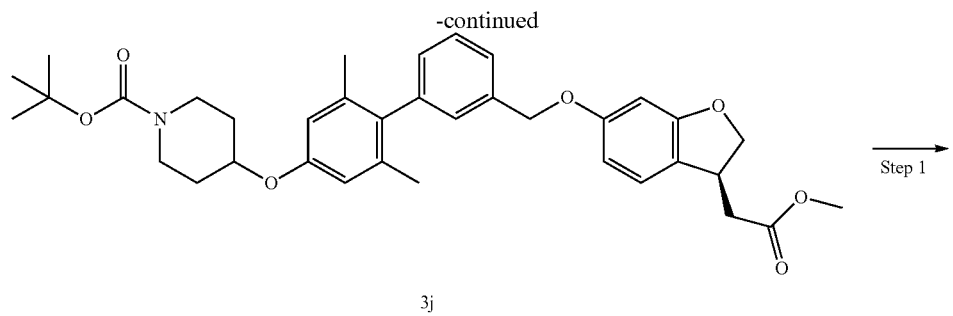

3j

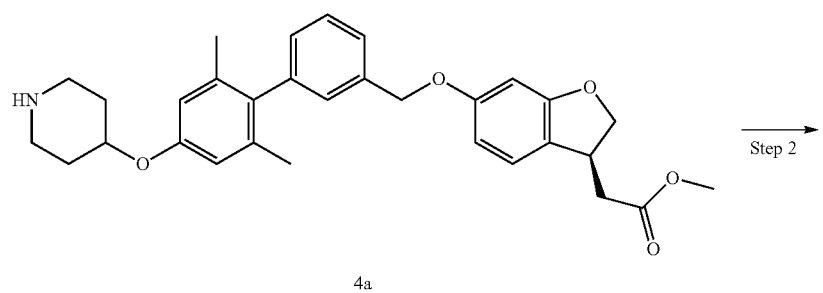

4a

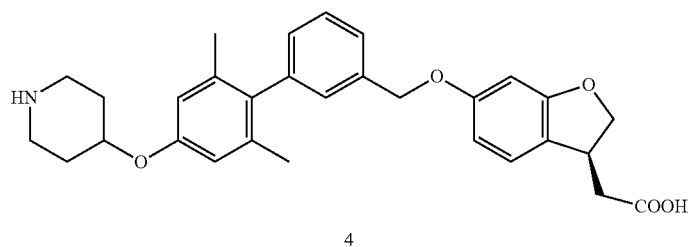

4

Step 1

(S)-Methyl 2-(6-((2',6'-dimethyl-4'-(piperidin-4-yloxy)biphenyl-3-yl)methoxy)-2,3-dihydrobenzofuran-3-yl)acetate Methyl (S)-2-(6-((4'-((1-(tert-butoxycarbonyl)piperidin-4-yl)oxy)-2',6'-dimethyl-biphenyl-3-yl)methoxy)-2,3-dihydrobenzofuran-3-yl)acetate 3j (75 mg, 0.13 mmol) was dissolved in 15 mL hydrochloric acid in dioxane. The reaction solution was reacted for 1 hour. The resulting solution was concentrated under reduced pressure to obtain the crude title compound (S)-methyl 2-(6-((2',6'-dimethyl-4'-(piperidin-4-yloxy)biphenyl-3-yl)methoxy)-2,3-dihydrobenzofuran-3-yl)acetate 4a (75 mg), as a white solid which was directly used in the next step without further purification.

Step 2

(S)-2-(6-((2',6'-Dimethyl-4'-(piperidin-4-yloxy)biphenyl-3-yl)methoxy)-2,3-dihydrobenzofuran-3-yl)acetic acid The crude (S)-methyl 2-(6-((2',6'-dimethyl-4'-(piperidin-4-yloxy)biphenyl-3-yl)methoxy)-2,3-dihydrobenzofuran-3-yl)acetate 4a (31 mg, 0.06 mmol) was dissolved in 5 mL of methanol, followed by addition of 1M aqueous sodium hydroxide solution (0.6 mL, 0.62 mmol). The reaction solution was reacted for 2 hours. The resulting solution was concentrated under reduced pressure, mixed with 3 mL of water, 1M citric acid was added dropwise to adjust the pH to 5, and the solution was extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((2',6'-dimethyl-4'-(piperidin-4-yloxy)biphenyl-3-yl)methoxy)-2,3-dihydrobenzofuran-3-yl)acetic acid 4 (31 mg, yield 100%) as a white solid.

MS m/z (ESI): 486.3 [M−1]

$^1$H NMR (400 MHz, DMSO-$d_6$) δ 7.51-7.38 (m, 2H), 7.21 (s, 1H), 7.11 (dd, 2H), 6.70 (s, 2H), 6.51-6.54 (m, 2H), 5.10 (s, 2H), 4.80 (t, 1H), 4.52 (s, 1H), 4.33 (t, 1H), 3.81-3.86 (m, 1H), 3.15 (s, 2H), 2.81 (s, 2H), 2.85 (d, 1H), 2.66 (dd, 1H), 2.03 (s, 6H), 1.90 (d, 4H).

Example 5

(S)-2-(6-((2',6'-Dimethyl-4'-((1-(methylsulfonyl)piperidin-4-yl)oxy)biphenyl-3-yl)methoxy)-2,3-dihydrobenzofuran-3-yl)acetic acid

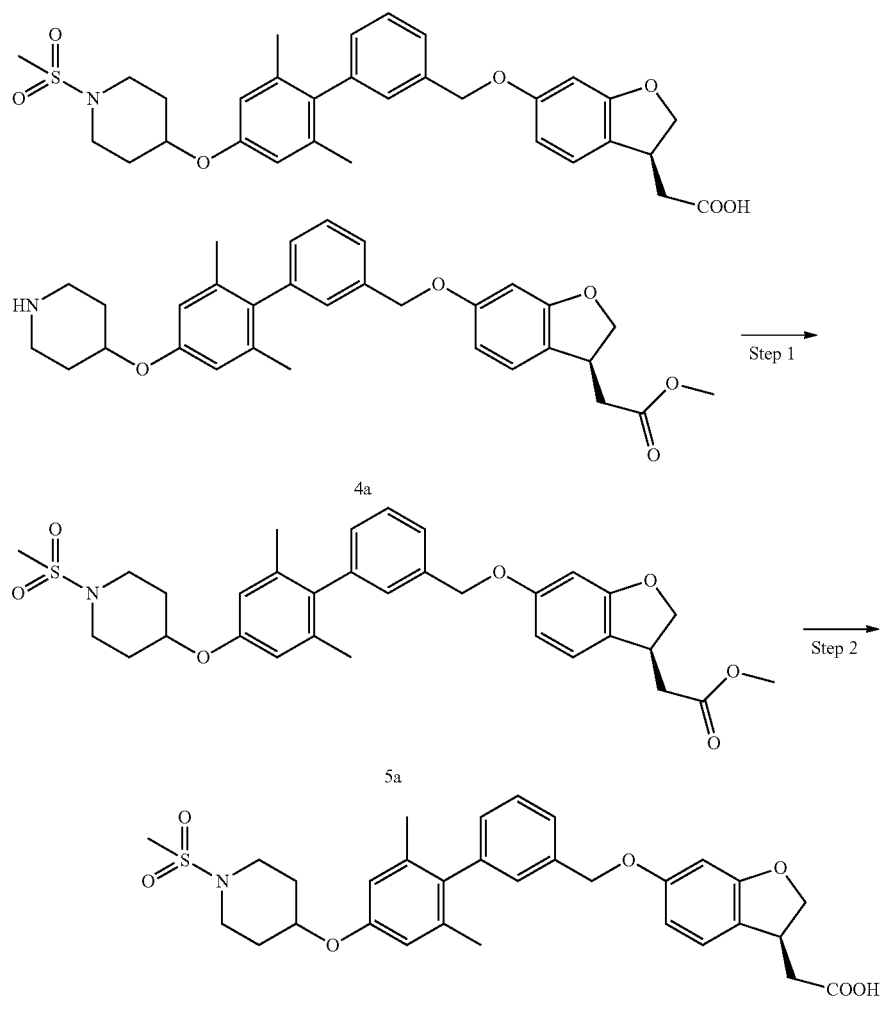

Step 1

(S)-Methyl 2-(6-((2',6'-dimethyl-4'-((1-(methylsulfonyl)piperidin-4-yl)oxy)biphenyl-3-yl)methoxy)-2,3-dihydrobenzofuran-3-yl)acetate (S)-Methyl 2-(6-((2',6'-dimethyl-4'-(piperidin-4-yloxy)biphenyl-3-yl)methoxy)-2,3-dihydrobenzofuran-3-yl)acetate 4a (26 mg, 0.05 mmol) was dissolved in 5 mL of dichloromethane, followed by addition of methanesulfonyl chloride (6 mg, 0.05 mmol) and triethylamine (15 mg, 0.15 mmol). The reaction solution was reacted for 1 hour. The resulting solution was mixed with 10 mL of water, and concentrated under reduced pressure to obtain the crude title compound (S)-methyl 2-(6-((2',6'-dimethyl-4'-((1-(methylsulfonyl)piperidin-4-yl)oxy)biphenyl-3-yl)methoxy)-2,3-dihydrobenzofuran-3-yl)acetate 5a (40 mg) as a white solid, which was directly used in the next step without further purification.

MS m/z (ESI): 578.3 [M−1]

Step 2

(S)-2-(6-((2',6'-Dimethyl-4'-((1-(methylsulfonyl)piperidin-4-yl)oxy)biphenyl-3-yl)methoxy)-2,3-dihydrobenzofuran-3-yl)acetic acid The crude (S)-methyl 2-(6-((2',6'-dimethyl-4'-((1-(methylsulfonyl)piperidin-4-yl)oxy)biphenyl-3-yl)methoxy)-2,3-dihydrobenzofuran-3-yl)acetate 5a (28 mg, 0.05 mmol) was dissolved in 5 mL of ethanol, followed by addition of 1M aqueous sodium hydroxide solution (0.5 mL, 0.50 mmol). The reaction solution was reacted for 1 hour. 1M hydrochloric acid was added dropwise to the resulting solution to adjust the pH to 5, followed by extraction with ethyl acetate (20 mL×2). The combined organic extracts were washed with saturated sodium chloride solution (30 mL), dried with anhydrous magnesium sulphate, and filtered. The filtrate was concentrated under reduced pressure and the residue was purified using a method of preparative separation to obtain the title compound (S)-2-(6-((2',6'-dimethyl-4'-((1-(methylsulfonyl)piperidin-4-yl)oxy)biphenyl-3-yl)methoxy)-2,3-dihydrobenzofuran-3-yl)acetic acid 5 (12 mg, yield 44.0%) as a white solid.

MS m/z (ESI): 564.3 [M−1]

$^1$H NMR (400 MHz, CDCl$_3$) δ 7.38-7.45 (m, 2H), 7.18 (s, 1H), 7.05-7.10 (m, 2H), 6.67 (s, 2H), 6.47-6.51 (m, 2H), 5.07 (s, 2H), 4.77 (t, 1H), 4.57 (s, 1H), 4.30 (t, 1H), 3.82 (t, 1H), 3.36-3.41 (m, 4H), 2.79-2.84 (m, 4H), 2.59-2.66 (m, 1H), 2.00-2.04 (m, 10H).

Example 6

(S)-2-(6-((4'-((1-Acetylpiperidin-4-yl)oxy)-2',6'-dimethylbiphenyl-3-yl)methoxy)-2,3-dihydrobenzofuran-3-yl)acetic acid

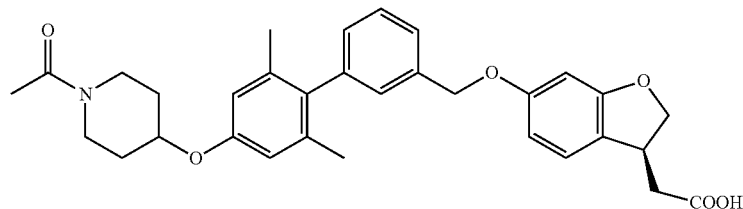

Step 1

(S)-methyl 2-(6-((4'-((1-Acetylpiperidin-4-yl)oxy)-2',6'-dimethylbiphenyl-3-yl)methoxy)-2,3-dihydrobenzofuran-3-yl)acetate (S)-Methyl 2-(6-((2',6'-dimethyl-4'-(piperidin-4-yloxy)biphenyl-3-yl)methoxy)-2,3-dihydrobenzofuran-3-yl)acetate 4a (20 mg, 0.04 mmol) was dissolved in 2 mL of dichloromethane, followed by addition of acetic anhydride (5 mg, 0.05 mmol) and triethylamine (12 mg, 0.12 mmol). The reaction solution was stirred for 2 hours. The resulting solution was concentrated under reduced pressure and the residue was purified by TLC with elution system A to obtain the title compound (S)-methyl 2-(6-((4'-((1-acetylpiperidin-4-yl)

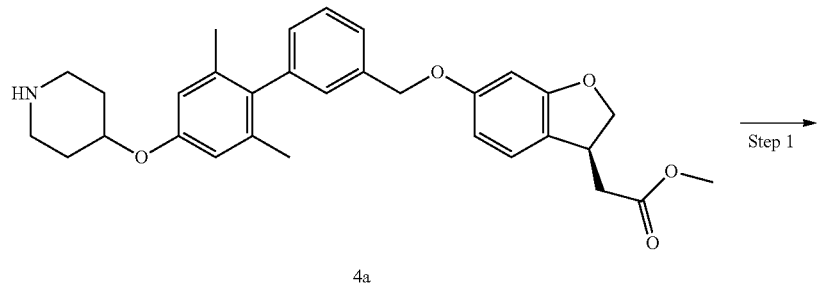

4a

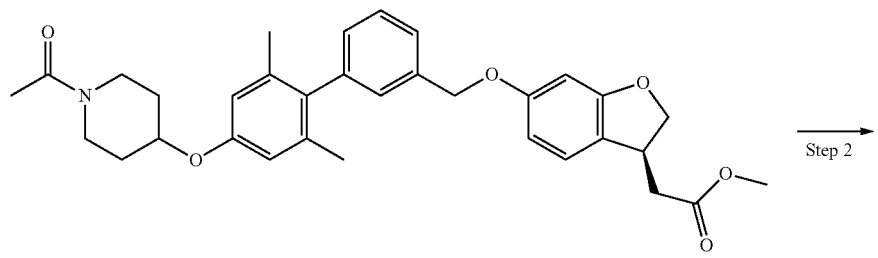

6a

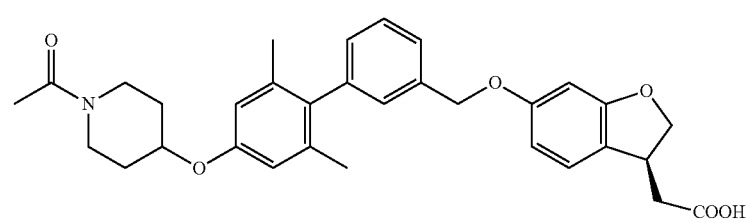

6 oxy)-2',6'-dimethylbiphenyl-3-yl)methoxy)-2,3-dihydrobenzofuran-3-yl)acetate 6a (10 mg, yield 47.0%) as a colorless oil.

MS m/z (ESI): 544.3 [M+1]

Step 2

(S)-2-(6-((4'-((1-Acetylpiperidin-4-yl)oxy)-2',6'-dimethylbiphenyl-3-yl)methoxy)-2,3-dihydrobenzofuran-3-yl)acetic acid (S)-Methyl 2-(6-((4'-((1-acetylpiperidin-4-yl)oxy)-2',6'-dimethylbiphenyl-3-yl)methoxy)-2,3-dihydrobenzofuran-3-yl)acetate 6a (10 mg, 0.02 mmol) was dissolved in 2 mL of a mixture of the solvents tetrahydrofuran and methanol (V/V=1:1), followed by addition of 1M aqueous lithium hydroxide solution (0.2 mL, 0.20 mmol). The reaction solution was stirred for 2 hours. The resulting solution was concentrated under reduced pressure, 1M hydrochloric acid was added dropwise to adjust the pH to 5, and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((4'-((1-acetylpiperidin-4-yl)oxy)-2',6'-dimethylbiphenyl-3-yl)methoxy)-2,3-dihydrobenzofuran-3-yl)acetic acid 6 (8 mg, yield 84.2%) as a white solid.

MS m/z (ESI): 530.4 [M+1]

$^1$H NMR (400 MHz, CDCl$_3$) δ 7.37-7.45 (m, 2H), 7.18 (s, 1H), 7.05-7.10 (m, 2H), 6.67 (s, 2H), 6.47-6.51 (m, 2H), 5.07 (s, 2H), 4.75-4.79 (m, 1H), 4.57 (s, 1H), 4.28-4.31 (m, 1H), 3.73-3.83 (m, 4H), 2.78-2.83 (m, 1H), 2.58-2.64 (m, 1H), 2.22-2.26 (m, 1H), 2.15 (m, 3H), 1.94-2.06 (m, 10H).

Example 7

2-((S)-6-((4'-(((S)-1-(tert-Butoxycarbonyl)pyrrolidin-3-yl)oxy)-2',6'-dimethylbiphenyl-3-yl)methoxy)-2,3-dihydrobenzofuran-3-yl)acetic acid

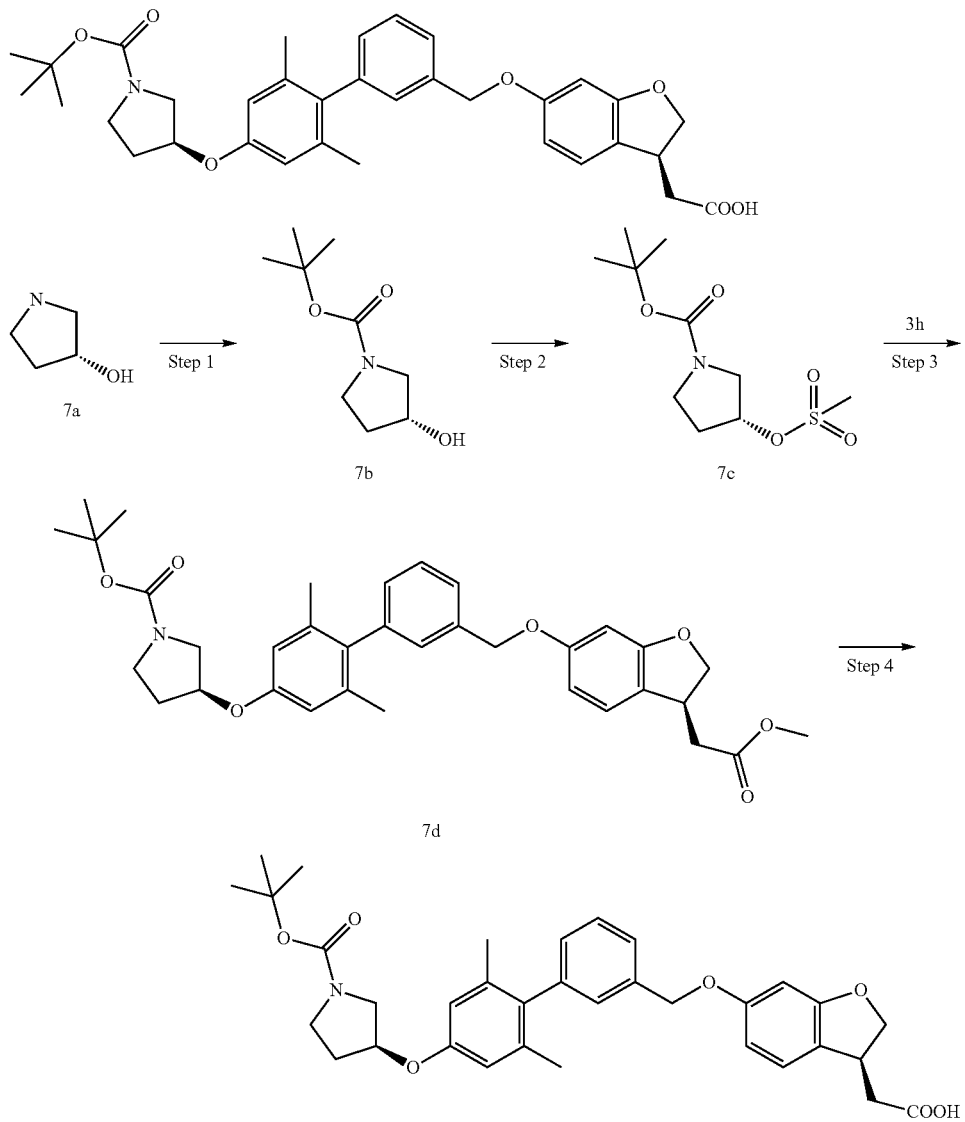

Step 1

(R)-tert-Butyl 3-hydroxypyrrolidine-1-carboxylate (R)-Pyrrolidin-3-ol 7a (348 mg, 4 mmol) and triethylamine (808 mg, 8 mmol) were dissolved in 20 mL of dichloromethane, followed by addition of di-tert-butyl dicarbonate (959 mg, 4.40 mmol) in an ice bath. The reaction solution was warmed up to room temperature and stirred for 3 hours. The resulting solution was mixed with 50 mL of dichloromethane, washed with saturated sodium chloride solution (5 mL×3), dried with anhydrous magnesium sulphate, and filtered. The filtrate was concentrated under reduced pressure. The residue was purified by silica gel column chromatography with elution system B to obtain the title compound (R)-tert-butyl 3-hydroxypyrrolidine-1-carboxylate 7b (400 mg, yield 53.4%) as a colorless oil.

Step 2

(R)-tert-Butyl 3-((methylsulfonyl)oxy)pyrrolidine-1-carboxylate (R)-tert-Butyl 3-hydroxypyrrolidine-1-carboxylate 7b (375 mg, 2 mmol) was dissolved in 10 mL of dichloromethane in an ice bath, followed by addition of triethylamine (404 mg, 4 mmol) and methanesulfonyl chloride (274 mg, 2.40 mmol).

The reaction solution was warmed up to room temperature and stirred for 3 hours. The resulting solution was mixed with 5 mL of water and extracted with dichloromethane (20 mL×3). The combined organic extracts were washed with saturated sodium chloride solution (30 mL), dried with anhydrous magnesium sulphate, and filtered. The filtrate was concentrated under reduced pressure to obtain the crude title compound (R)-tert-butyl 3-((methylsulfonyl)oxy)pyrrolidine-1-carboxylate 7c (530 mg) as a yellow oil, which was directly used in the next step without further purification.

Step 3

Methyl 2-(((S)-6-((4'-((S)-1-(tert-butoxycarbonyl)pyrrolidin-3-yl)oxy)-2',6'-dimethylbiphenyl-3-yl)methoxy)-2,3-dihydrobenzofuran-3-yl)acetate (R)-tert-Butyl 3-((methylsulfonyl)oxy)pyrrolidine-1-carboxylate 7c (190 mg, 0.72 mmol), methyl (S)-2-(6-((4'-hydroxyl-2',6'-dimethylbiphenyl-3-yl)methoxy)-2,3-dihydrobenzofuran-3-yl)acetate 3 h (200 mg, 0.48 mmol) and cesium carbonate (310 mg, 0.96 mmol) were dissolved in 10 mL of N,N-dimethylformamide. The reaction solution was heated to 80° C. and stirred for 12 hours. The resulting solution was mixed with 5 mL of water and 50 mL of ethyl acetate. The organic phase was washed with saturated sodium chloride solution (20 mL), dried with anhydrous sodium sulfate, and filtered. The filtrate was concentrated under reduced pressure and the residue was purified by elution system B to obtain the title compound methyl 2-(((S)-6-((4'-((S)-1-(tert-butoxycarbonyl)pyrrolidin-3-yl)oxy)-2',6'-dimethylbiphenyl-3-yl)methoxy)-2,3-dihydrobenzofuran-3-yl)acetate 7d (130 mg, yield 46.4%) as a colorless oil.

MS m/z (ESI): 488.2 [M−99]

Step 4

2-((S)-6-((4'-(((S)-1-(tert-Butoxycarbonyl)pyrrolidin-3-yl)oxy)-2',6'-dimethylbiphenyl-3-yl)methoxy)-2,3-dihydrobenzofuran-3-yl)acetic acid Methyl 2-(((S)-6-((4'-((S)-1-(tert-butoxycarbonyl)pyrrolidin-3-yl)oxy)-2',6'-dimethylbiphenyl-3-yl)methoxy)-2,3-dihydrobenzofuran-3-yl)acetate 7d (30 mg, 0.05 mmol) was dissolved in 4 mL of the mixture solvent of tetrahydrofuran and methanol (V/V=1:1), followed by addition of 1M aqueous lithium hydroxide solution (0.1 mL, 0.10 mmol). The reaction solution was stirred for 2 hours. The resulting solution was concentrated under reduced pressure, 1M hydrochloric acid was added dropwise to adjust the pH to 5, and extracted with ethyl acetate (20 mL×2). The combined organic extracts were washed with saturated sodium chloride solution (30 mL), dried with anhydrous magnesium sulphate, and filtered. The filtrate was concentrated under reduced pressure and the residue was purified by TLC with elution system A to obtain the title compound 2-((S)-6-((4'-(((S)-1-(tert-butoxycarbonyl)pyrrolidin-3-yl)oxy)-2',6'-dimethylbiphenyl-3-yl)methoxy)-2,3-dihydrobenzofuran-3-yl)acetic acid 7 (10 mg, yield 34.4%) as a white solid.

MS m/z (ESI): 572.3 [M−1]

$^1$H NMR (400 MHz, CDCl$_3$) δ 7.37-7.45 (m, 2H), 7.18 (s, 1H), 7.05-7.10 (m, 2H), 6.63 (s, 2H), 6.47-6.51 (m, 2H), 5.07 (s, 2H), 4.91 (s, 1H), 4.75-4.79 (m, 1H), 4.28-4.32 (m, 1H), 3.80-3.86 (m, 1H), 3.52-3.67 (m, 3H), 2.78-2.84 (m, 1H), 2.59-2.65 (m, 1H), 2.59-2.66 (m, 1H), 2.22-2.24 (m, 1H), 2.00-2.03 (m, 7H), 1.49 (s, 9H).

Example 8

2-((S)-6-((2',6'-Dimethyl-4'-(((S)-1-(methylsulfonyl)pyrrolidin-3-yl)oxy)biphenyl-3-yl)methoxy)-2,3-dihydrobenzofuran-3-yl)acetic acid

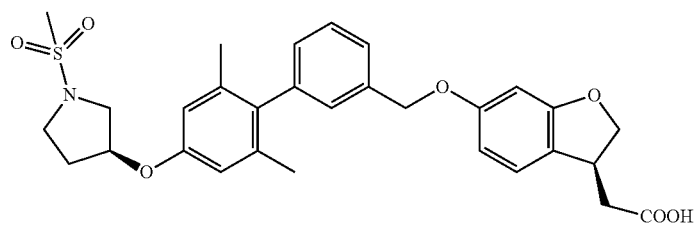

-continued

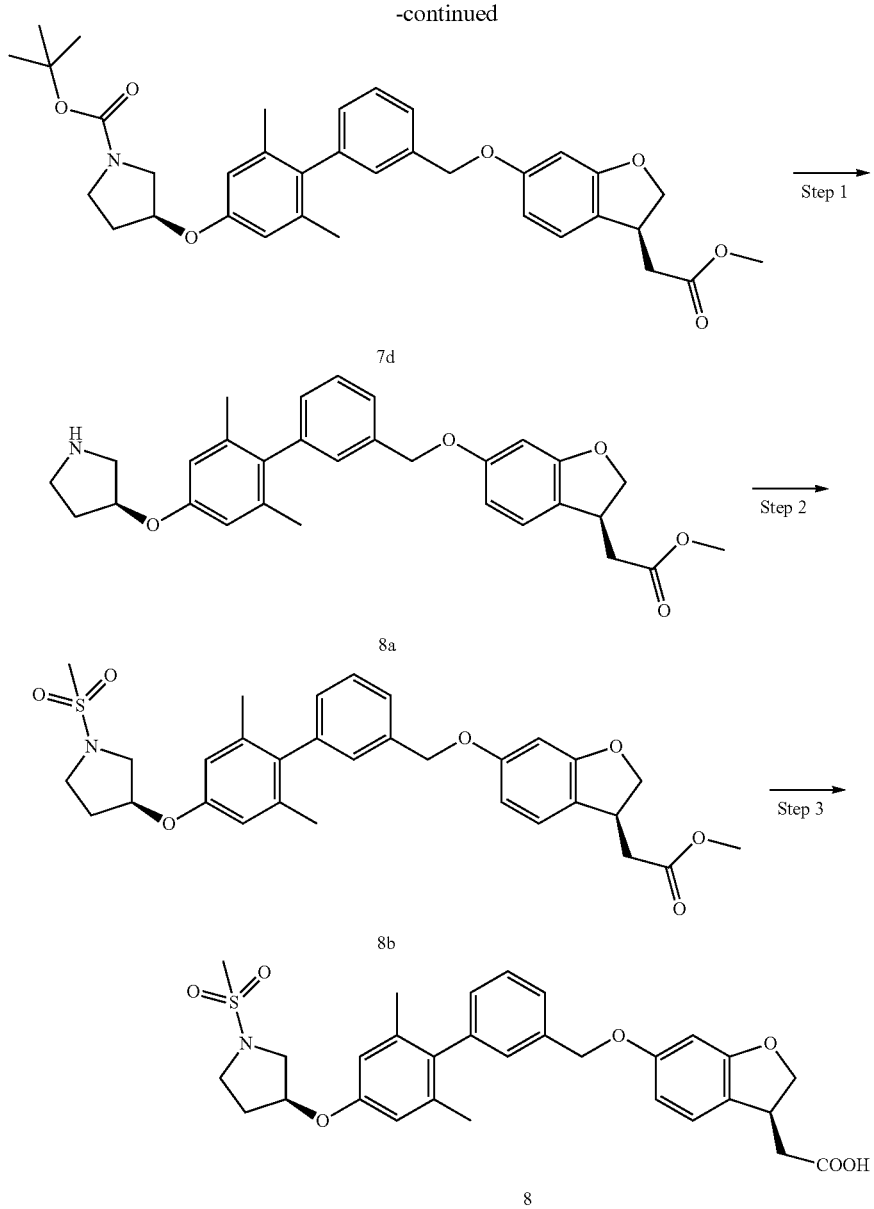

Step 1

Methyl 2-((S)-6-((2',6'-dimethyl-4'-((S)-pyrrolidin-3-yloxy)biphenyl-3-yl)methoxy)-2,3-dihydrobenzofuran-3-yl)acetate Methyl 2-(((S)-6-((4'-((S)-1-(tert-butoxycarbonyl)pyrrolidin-3-yl)oxy)-2',6'-dimethylbiphenyl-3-yl)methoxy)-2,3-dihydrobenzofuran-3-yl)acetate 7d (100 mg, 0.17 mmol) was dissolved in 3 mL of dichloromethane, followed by addition of 2 mL of trifluoroacetic acid in an ice bath. The reaction solution was stirred for 1 hour. The resulting solution was concentrated under reduced pressure to obtain the crude title compound methyl 2-((S)-6-((2',6'-dimethyl-4'-((S)-pyrrolidin-3-yloxy)biphenyl-3-yl)methoxy)-2,3-dihydrobenzofuran-3-yl)acetate 8a (90 mg) as a colorless oil, which was directly used in the next step without further purification.

Step 2

Methyl 2-((S)-6-((2',6'-dimethyl-4'-(((S)-1-(methylsulfonyl)pyrrolidin-3-yl)oxy)biphenyl-3-yl)methoxy)-2,3-dihydrobenzofuran-3-yl)acetate The crude methyl 2-((S)-6-((2',6'-dimethyl-4'-((S)-pyrrolidin-3-yloxy)biphenyl-3-yl)methoxy)-2,3-dihydrobenzofuran-3-yl)acetate 8a (45 mg, 0.09 mmol) was dissolved in 3 mL of dichloromethane, followed by addition of methanesulfonyl chloride (13 mg, 0.11 mmol) and triethylamine (18 mg, 0.18 mmol). The reaction solution was stirred for 2 hours. The resulting solution was added with 30 mL of ethyl acetate. The organic phase was washed with saturated sodium chloride solution (30 mL), dried with anhydrous magnesium sulphate, and filtered. The filtrate was concentrated under reduced pressure and the residue was purified by TLC with elution system A to obtain the title compound methyl 2-((S)-

6-((2',6'-dimethyl-4'-(((S)-1-(methylsulfonyl)pyrrolidin-3-yl)oxy)biphenyl-3-yl)methoxy)-2,3-dihydrobenzofuran-3-yl)acetate 8b (40 mg, yield 77.0%) as a colorless oil.

MS m/z (ESI): 583.4 [M+18]

Step 3

2-((S)-6-((2',6'-Dimethyl-4'-(((S)-1-(methylsulfonyl)pyrrolidin-3-yl)oxy)biphenyl-3-yl)methoxy)-2,3-dihydrobenzofuran-3-yl)acetic acid Methyl 2-((S)-6-((2',6'-dimethyl-4'-(((S)-1-(methylsulfonyl)pyrrolidin-3-yl)oxy)biphenyl-3-yl)methoxy)-2,3-dihydrobenzofuran-3-yl)acetate 8b (30 mg, 0.05 mmol) was dissolved in 2 mL of a mixture of the solvents tetrahydrofuran and methanol (V/V=1:1), followed by addition of 1M aqueous lithium hydroxide solution (0.1 mL, 0.10 mmol). The reaction solution was stirred for 2 hours. The resulting solution was concentrated under reduced pressure, 1M hydrochloric acid was added dropwise to adjust the pH to 5 and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound 2-((S)-6-((2',6'-dimethyl-4'-(((S)-1-(methylsulfonyl)pyrrolidin-3-yl)oxy)biphenyl-3-yl)methoxy)-2,3-dihydrobenzofuran-3-yl)acetic acid 8 (28 mg, yield 94.2%) as a white solid.

MS m/z (ESI): 550.2 [M−1]

$^1$H NMR (400 MHz, CDCl$_3$) δ 7.38-7.46 (m, 2H), 7.17 (s, 1H), 7.05-7.09 (m, 2H), 6.59 (s, 2H), 6.47-6.52 (m, 2H), 5.07 (s, 2H), 4.96 (s, 1H), 4.75-4.79 (m, 1H), 4.28-4.32 (m, 1H), 3.80-3.86 (m, 1H), 3.61-3.67 (m, 3H), 3.45-3.52 (m, 1H), 2.88 (s, 3H), 2.79-2.84 (m, 1H), 2.59-2.66 (m, 1H), 2.33-2.38 (m, 1H), 2.17-2.25 (m, 1H), 1.99 (s, 6H).

Example 9

2-((S)-6-((4'-(((S)-1-Acetylpyrrolidin-3-yl)oxy)-2',6'-dimethylbiphenyl-3-yl)methoxy)-2,3-dihydrobenzofuran-3-yl)acetic acid

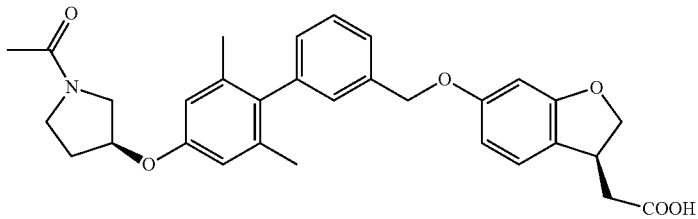

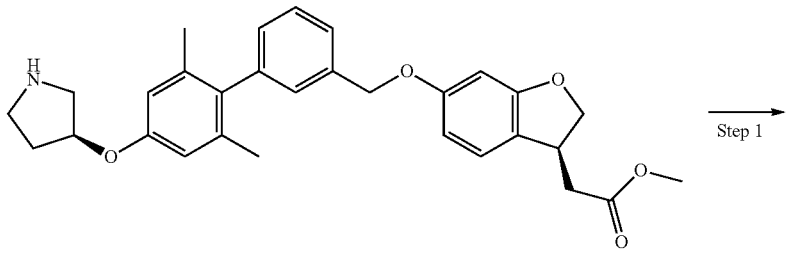

8a

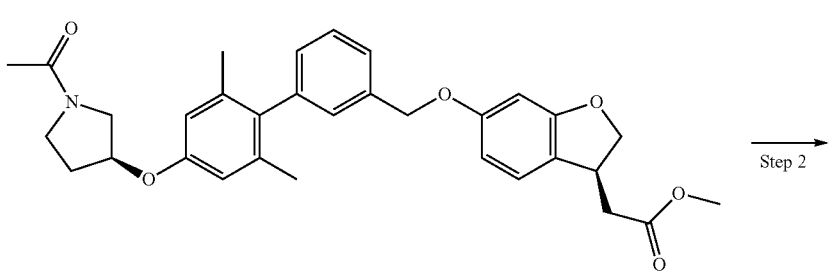

9a

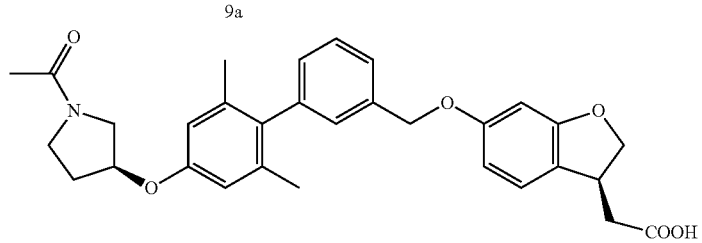

9

Step 1

Methyl 2-((S)-6-((4'-(((S)-1-acetylpyrrolidin-3-yl)oxy)-2',6'-dimethylbiphenyl-3-yl)methoxy)-2,3-dihydrobenzofuran-3-yl)acetate The crude methyl 2-((S)-6-((2',6'-dimethyl-4'-((S)-pyrrolidin-3-yloxy)biphenyl-3-yl)methoxy)-2,3-dihydrobenzofuran-3-yl)acetate 8a (45 mg, 0.09 mmol) were dissolved in 3 mL of dichloromethane, followed by addition of acetic anhydride (13 mg, 0.11 mmol) and triethylamine (18 mg, 0.18 mmol). The reaction solution was stirred for 2 hours. The resulting solution was mixed with 20 mL of dichloromethane. The organic phase was washed with saturated sodium chloride solution (30 mL), dried with anhydrous magnesium sulphate, and filtered. The filtrate was concentrated under reduced pressure to obtain the crude title compound methyl 2-((S)-6-((4'-(((S)-1-acetylpyrrolidin-3-yl)oxy)-2',6'-dimethylbiphenyl-3-yl)methoxy)-2,3-dihydrobenzofuran-3-yl)acetate 9a (45 mg, yield 92.5%) as a colorless oil.

MS m/z (ESI): 530.4 [M+1]

Step 2

2-((S)-6-((4'-(((S)-1-Acetylpyrrolidin-3-yl)oxy)-2',6'-dimethylbiphenyl-3-yl)methoxy)-2,3-dihydrobenzofuran-3-yl)acetic acid The crude methyl 2-((S)-6-((4'-(((S)-1-acetylpyrrolidin-3-yl)oxy)-2',6'-dimethylbiphenyl-3-yl)methoxy)-2,3-dihydrobenzofuran-3-yl)acetate 9a (40 mg, 0.08 mmol) was dissolved in 2 mL of a mixture of the solvents tetrahydrofuran and methanol (V/V=1:1), followed by addition of 1M aqueous lithium hydroxide solution (0.4 mL, 0.40 mmol). The reaction solution was stirred for 3 hours. The resulting solution was concentrated under reduced pressure. The residue was mixed with 10 mL of water, 1M hydrochloric acid was added dropwise to adjust the pH to 3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure and the residue was purified by TLC with elution system A to obtain the title compound 2-((S)-6-((4'-(((S)-1-acetylpyrrolidin-3-yl)oxy)-2',6'-dimethylbiphenyl-3-yl)methoxy)-2,3-dihydrobenzofuran-3-yl)acetic acid 9 (20 mg, yield 51.3%) as a white solid.

MS m/z (ESI): 514.3 [M−1]

$^1$H NMR (400 MHz, CDCl$_3$) δ 7.41 (dd, 2H), 7.15 (d, 1H), 7.05 (d, 2H), 6.61 (d, 2H), 6.52-6.42 (m, 2H), 5.06 (s, 2H), 4.97 (d, 1H), 4.76 (dd, 1H), 4.28 (dd, 1H), 3.93-3.56 (m, 5H), 2.79 (dd, 1H), 2.60 (dd, 1H), 2.40-2.17 (m, 2H), 2.16-2.07 (m, 3H), 2.02-1.92 (m, 6H).

Example 10

(S)-2-(6-((4'-(Cyclopentyloxy)-2',6'-dimethylbiphenyl-3-yl)methoxy)-2,3-dihydrobenzofuran-3-yl)acetic acid

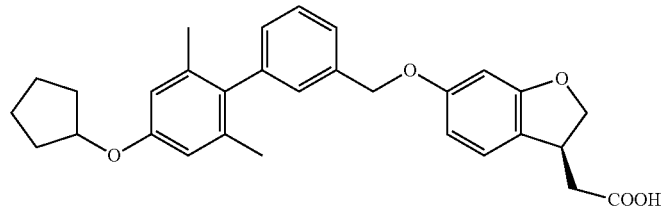

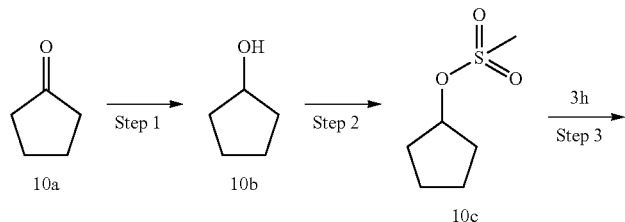

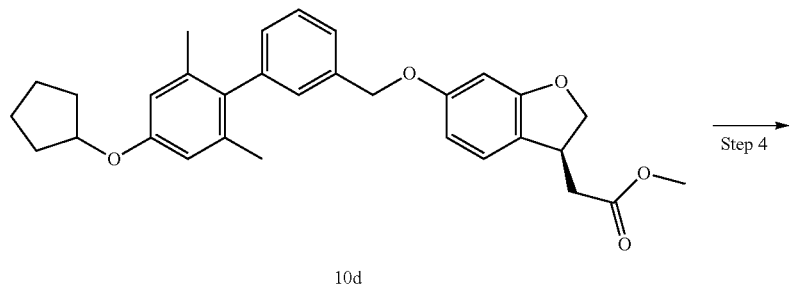

-continued

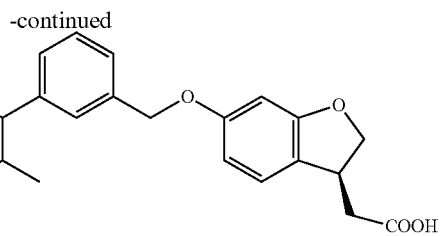

10

Step 1

Cyclopentanol

Cyclopentanone 10a (1 g, 0.01 mol) was dissolved in 10 mL of methanol, followed by addition of sodium borohydride (542 mg, 0.01 mmol) in an ice bath. The reaction solution was warmed up to room temperature and stirred for 2 hours. The resulting solution was mixed with 10 mL of water and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the crude title compound cyclopentanol 10b (1 g) as a colorless oil, which was directly used in the next step without further purification.

Step 2

Cyclopentyl Methanesulfonate

The crude cyclopentanol 10b (50 mg, 0.58 mmol), methanesulfonyl chloride (80 mg, 0.70 mmol), and triethylamine (117 mg, 1.16 mmol) were dissolved in 10 mL of dichloromethane. The reaction solution was stirred for 2 hours. The resulting solution was added with 10 mL of water and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the crude title compound cyclopentyl methanesulfonate 10c (90 mg) as a yellow oil, which was directly used in the next step without further purification.

Step 3

(S)-Methyl 2-(6-((4'-(cyclopentyloxy)-2',6'-dimethylbiphenyl-3-yl)methoxy)-2,3-dihydrobenzofuran-3-yl)acetate Cyclopentyl methanesulfonate 10c (50 mg, 0.28 mmol), (S)-methyl 2-(6-((4'-hydroxy-2',6'-dimethylbiphenyl-3-yl)methoxy)-2,3-dihydrobenzofuran-3-yl)acetate 3 h (60 mg, 0.14 mmol), and cesium carbonate (100 mg, 0.30 mmol) were dissolved in 10 mL of N,N-dimethylformamide. The reaction mixture was heated to 80° C. and stirred for 12 hours. The resulting mixture was mixed with 10 mL of water and extracted with ethyl acetate (20 mL×2). The organic phase was washed with water (20 mL×2) and saturated sodium chloride solution (20 mL) successively, dried with anhydrous sodium sulfate, and filtered. The filtrate was concentrated under the reduced pressure and the residue was purified by elution system B to obtain the title compound (S)-methyl 2-(6-((4'-(cyclopentyloxy)-2',6'-dimethylbiphenyl-3-yl) methoxy)-2,3-dihydrobenzofuran-3-yl)acetate 10d (40 mg, yield 30.0%) as a colorless slime.

MS m/z (ESI): 487.3 [M+1]

Step 4

(S)-2-(6-((4'-(Cyclopentyloxy)-2',6'-dimethylbiphenyl-3-yl)methoxy)-2,3-dihydrobenzofuran-3-yl)acetic acid (S)-Methyl 2-(6-((4'-(cyclopentyloxy)-2',6'-dimethylbiphenyl-3-yl)methoxy)-2,3-dihydrobenzofuran-3-yl)acetate 10d (40 mg, 0.08 mmol) was dissolved in 7 mL of a mixture of the solvents tetrahydrofuran and methanol (V/V=2:5), followed by addition of 1M aqueous lithium hydroxide solution (0.8 mL, 0.80 mmol). The reaction solution was stirred for 2 hours. The resulting solution was concentrated under reduced pressure. The residue was mixed with 10 mL of water, 1M hydrochloric acid was added dropwise to adjust the pH to 4~5, and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((4'-(cyclopentyloxy)-2',6'-dimethylbiphenyl-3-yl)methoxy)-2,3-dihydrobenzofuran-3-yl)acetic acid 10 (30 mg, yield 80.0%) as a white solid.

MS m/z (ESI): 471.2 [M-1]

$^1$H NMR (400 MHz, CDCl$_3$) δ 7.38-7.42 (m, 2H), 7.18 (s, 1H), 7.05-7.11 (m, 2H), 6.63 (s, 2H), 6.47-6.51 (m, 2H), 5.07 (s, 2H), 4.74-4.79 (m, 2H), 4.27-4.31 (m, 1H), 3.75-4.90 (m, 1H), 2.79-2.81 (m, 1H), 2.63-2.66 (m, 2H), 1.99 (s, 6H), 1.89-1.92 (m, 6H), 1.62-1.82 (m, 2H).

Example 11

2-((S)-6-((2',6'-Dimethyl-4'-(((R)-1-(methylsulfonyl)pyrrolidin-3-yl)oxy)biphenyl-3-yl)methoxy)-2,3-dihydrobenzofuran-3-yl)acetic acid

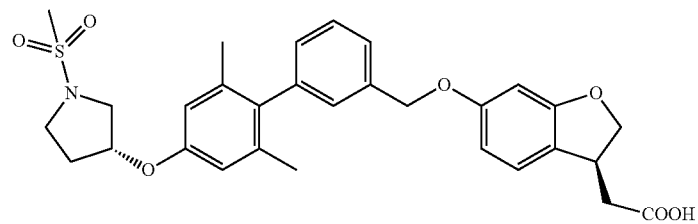

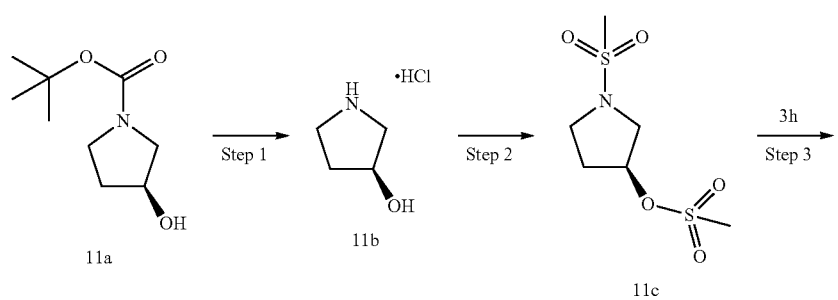

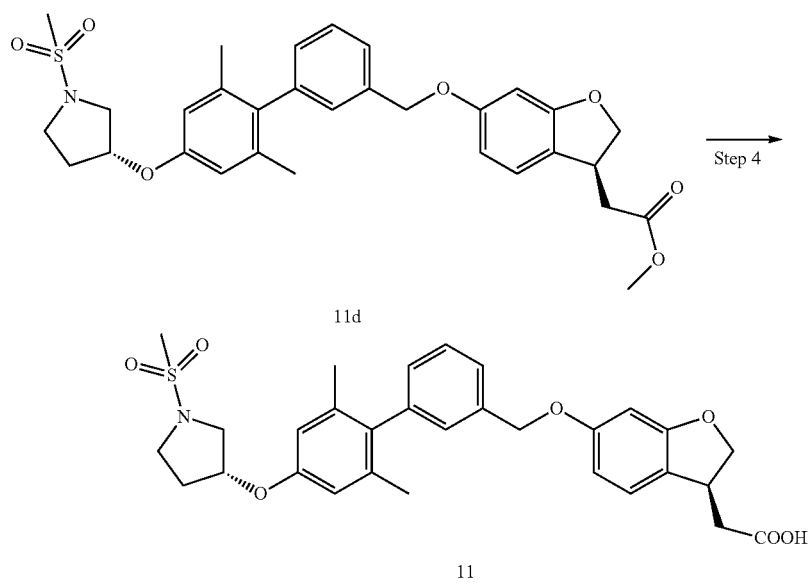

Step 1

(S)-3-hydroxyl-pyrrolidine hydrochloride (S)-tert-Butyl 3-hydroxypyrrolidine-1-carboxylate 11a (1.87 g, 10 mmol) was dissolved in 20 mL of hydrochloric acid in dioxane. The reaction solution was stirred for 0.5 hours. The resulting solution was concentrated under reduced pressure to obtain the crude title compound (S)-3-hydroxyl-pyrrolidine hydrochloride 11b (0.98 g) as a white solid, which was directly used in the next step without further purification.

Step 2

(S)-1-(Methylsulfonyl)pyrrolidin-3-yl methanesulfonate

The crude (S)-3-hydroxyl-pyrrolidine hydrochloride 11b (124 mg, 1 mmol) was dissolved in 15 mL of dichloromethane, followed by addition of triethylamine (303 mg, 3 mmol). The reaction solution was cooled down to 0° C., followed by addition of methanesulfonyl chloride (264 mg, 2.30 mmol), then warmed up to room temperature and stirred for another 2.5 hours. The resulting solution was mixed with 10 mL of dichloromethane, 1M citric acid was added dropwise to adjust the pH to 4~5, the organic phase was dried with anhydrous magnesium sulphate and filtered. The filtrate was concentrated under reduced pressure to obtain the crude title compound (S)-1-(methylsulfonyl)pyrrolidin-3-yl methanesulfonate 11c (153 mg) as a yellow solid, which was directly used in the next step without further purification.

Step 3

Methyl 2-((S)-6-((2',6'-dimethyl-4'-(((R)-1-(methylsulfonyl)pyrrolidin-3-yl)oxy)biphenyl-3-yl)methoxy)-2,3-dihydrobenzofuran-3-yl)acetate (s)-1-(Methylsulfonyl)pyrrolidin-3-yl methanesulfonate 11c (41 mg, 0.17 mmol), (S)-methyl 2-(6-((4'-hydroxy-2',6'-dimethylbiphenyl-3-yl)methoxy)-2,3-dihydrobenzofuran-3-yl)acetate 3 h (70 mg, 0.17 mmol) and cesium carbonate (165 mg, 0.50 mmol) were dissolved in 10 mL of N,N-dimethylformamide. The reaction solution was heated to 80° C., and stirred for 12 hours. The resulting solution was concentrated under reduced pressure and the residue was purified by silica gel column chromatography with elution system B to obtain the title compound methyl 2-((S)-6-((2',6'-dimethyl-4'-(((R)-1-(methylsulfonyl)pyrrolidin-3-yl)oxy)biphenyl-3-yl)methoxy)-2,3-dihydrobenzofuran-3-yl)acetate 11d (71 mg, yield 75.1%) as a light yellow slime.

MS m/z (ESI): 583.3 [M+18]

Step 4

2-((S)-6-((2',6'-Dimethyl-4'-(((R)-1-(methylsulfonyl)pyrrolidin-3-yl)oxy)biphenyl-3-yl)methoxy)-2,3-dihydrobenzofuran-3-yl)acetic acid Methyl 2-((S)-6-((2',6'-dimethyl-4'-(((R)-1-(methylsulfonyl)pyrrolidin-3-yl)oxy)biphenyl-3-yl)methoxy)-2,3-dihydrobenzofuran-3-yl)acetate 11d (71 mg, 0.13 mmol) was dissolved in 10 mL of methanol, followed by addition of 2M aqueous sodium hydroxide solution (0.5 mL, 1 mmol). The reaction solution was stirred for 2 hours. To the resulting solution, 1M citric acid was added dropwise to adjust the pH to 4~5. The organic phase was dried with anhydrous magnesium sulphate and filtered. The filtrate was concentrated under reduced pressure to obtain the title compound 2-((S)-6-((2',6'-dimethyl-4'-(((R)-1-(methylsulfonyl)pyrrolidin-3-yl)oxy)biphenyl-3-yl)methoxy)-2,3-dihydrobenzofuran-3-yl)acetic acid 11 (70 mg, yield 100%) as a yellow solid.

MS m/z (ESI): 550.3 [M−1]

$^1$H NMR (400 MHz, CDCl$_3$) δ 7.53-7.37 (m, 2H), 7.20 (s, 1H), 7.11 (t, 2H), 6.62 (s, 2H), 6.58-6.47 (m, 2H), 5.10 (s, 2H), 4.99 (s, 1H), 4.81 (t, 1H), 4.33 (dd, 1H), 3.85 (dt, 1H), 3.75-3.61 (m, 3H), 3.58-3.45 (m, 1H), 2.92 (s, 3H), 2.85 (dd, 1H), 2.66 (dd, 1H), 2.39 (dd, 1H), 2.32-2.15 (m, 1H), 2.02 (d, 6H).

Example 12

2-((S)-6-((2,2',6'-Trimethyl-4'-(((S)-tetrahydrofuran-3-yl)oxy)biphenyl-3-yl)methoxy)-2,3-dihydrobenzofuran-3-yl)acetic acid

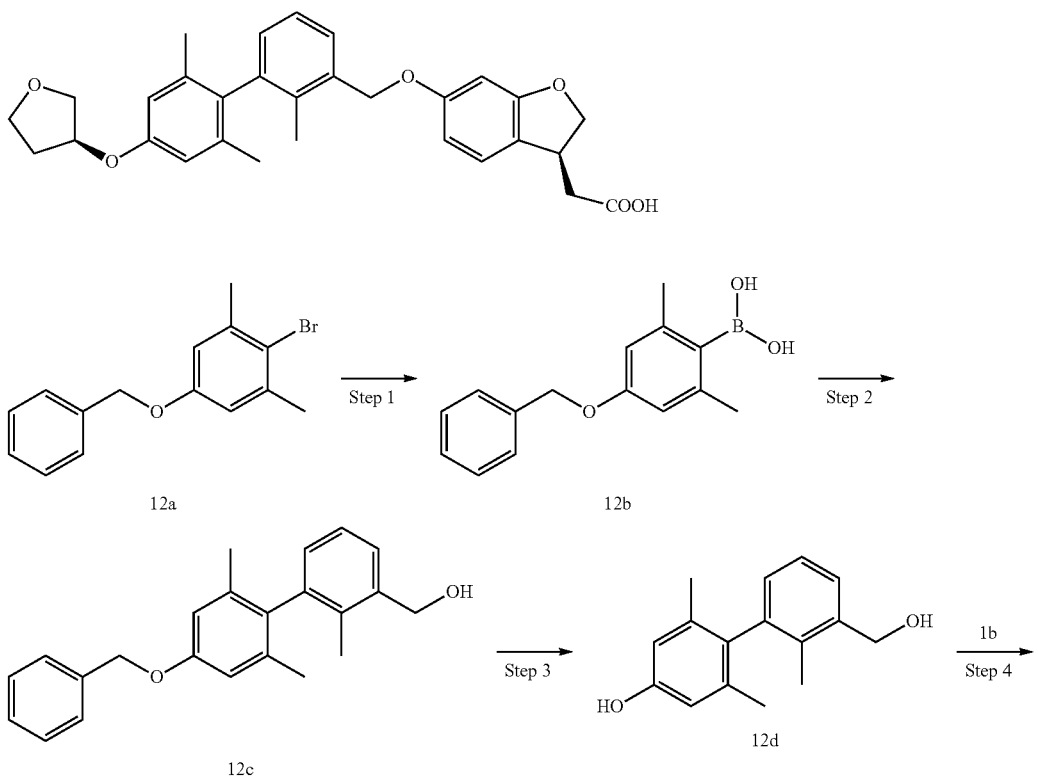

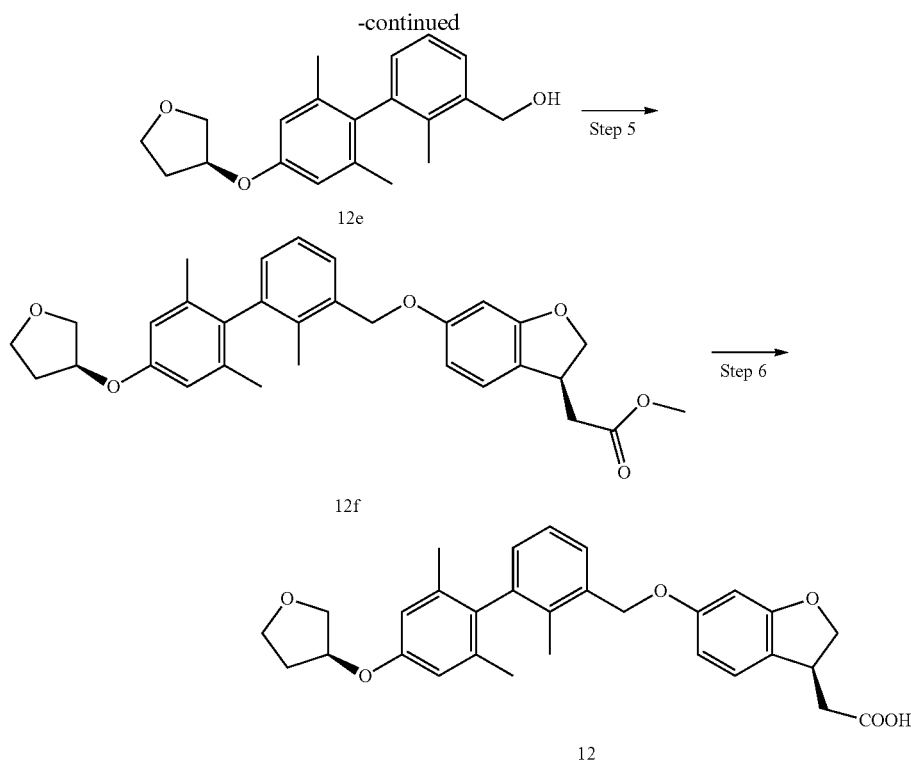

Step 1

(4-(Benzyloxy)-2,6-dimethylphenyl)boronic acid

S-(Benzyloxy)-2-bromo-1,3-dimethylbenzene 12a (2.91 g, 10 mmol, prepared by a method disclosed in PCT patent application WO2005019151) was dissolved in 35 mL of tetrahydrofuran in a dry-ice bath, followed by addition of n-butyllithium (4.8 mL, 12 mmol). The reaction solution was stirred for 1.5 hours, mixed with tripropyl borate (5.64 g, 30 mmol), then heated to 30° C. and stirred for 12 hours. To the resulting solution, 10 mL of 2M hydrochloric acid was added dropwise, then the solution was cooled down to room temperature and stirred for another 2 hours. The resulting solution was concentrated under reduced pressure and filtered. The filter cake was washed with water (10 mL) and n-hexane (10 mL) successively to obtain the title compound (4-(benzyloxy)-2,6-dimethylphenyl)boronic acid 12b (1.54 g, yield 60.2%) as a white solid.

MS m/z (ESI): 257.2 [M+1]

Step 2

(4'-(Benzyloxy)-2,2',6'-trimethylbiphenyl-3-yl)methanol

2-Methyl-3-bromo-phenylmethanol (201 mg, 1 mmol, prepared by a method disclosed in PCT patent application WO2010143733), (4-(benzyloxy)-2,6-dimethylphenyl)boronic acid 12b (300 mg, 1.20 mmol), 1 mL of 2M aqueous sodium carbonate solution, 2-dicyclohexylphosphino-2',6'-dimethoxy-1,1'-biphenyl (33 mg, 0.08 mmol) and tris(dibenzylideneacetone)dipalladium (18 mg, 0.02 mmol) were dissolved in 1 mL of N,N-dimethylformamide. The reaction mixture was reacted at 120° C. under microwave conditions for 1 hour. The resulting mixture was mixed with 10 mL of water and extracted with ethyl acetate (20 mL×2). The combined organic extracts were washed with saturated sodium chloride solution (30 mL), dried with anhydrous magnesium sulphate, and filtered. The filtrate was concentrated under reduced pressure. The residue was purified by silica gel column chromatography with elution system B to obtain the title compound (4'-(benzyloxy)-2,2',6'-trimethylbiphenyl-3-yl)methanol 12c (190 mg, yield 57.2%) as a red slime.

MS m/z (ESI): 333.3 [M+1]

Step 3

3'-(Hydroxymethyl)-2,2',6-trimethylbiphenyl-4-ol (4'-(Benzyloxy)-2,2',6'-trimethylbiphenyl-3-yl)methanol 12c (190 mg, 0.57 mmol) was dissolved in 5 mL of methanol, followed by addition of Pd/C (20 mg, 10%) under hydrogen atomosphere. The reaction solution was stirred for 12 hours. The resulting solution was filtered, and the filtrate was concentrated under reduced pressure to obtain the crude title compound 3'-(hydroxymethyl)-2,2',6-trimethylbiphenyl-4-ol 12d (128 mg) as a yellow solid, which was used directly in the next step without further purification.

MS m/z (ESI): 241.2 [M−1]

Step 4

(S)-(2,2',6'-Trimethyl-4'-((tetrahydrofuran-3-yl)oxy)biphenyl-3-yl)methanol

The crude (R)-tetrahydrofuran-3-yl methanesulfonate 1b (69 mg, 0.41 mmol), the crude 3'-(hydroxymethyl)-2,2',6-trimethylbiphenyl-4-ol 12d (100 mg, 3.13 mmol) and cesium carbonate (403 mg, 1.24 mmol) were dissolved in 315 mL of N,N-dimethylformamide. The reaction mixture was heated to 80° C. and stirred for 12 hours.

The resulting solution was concentrated under reduced pressure and the residue was purified by silica gel column chromatography with elution system B to obtain the title compound (S)-(2,2',6'-trimethyl-4'-((tetrahydrofuran-3-yl)oxy)biphenyl-3-yl)methanol 12e (110 mg, yield 86.0%) as an off-white solid.

MS m/z (ESI): 313.2 [M+1]

Step 5

Methyl 2-((S)-6-((2,2',6'-trimethyl-4'-(((S)-tetrahydrofuran-3-yl)oxy)biphenyl-3-yl)methoxy)-2,3-dihydrobenzofuran-3-yl)acetate (S)-(2,2',6'-Trimethyl-4'-((tetrahydrofuran-3-yl)oxy)biphenyl-3-yl)methanol 12e (75 mg, 0.24 mmol), methyl (S)-2-(6-hydroxyl-2,3-dihydrobenzofuran-3-yl)acetate (50 mg, 0.24 mmol) and triphenylphosphine (94 mg, 0.36 mmol) were dissolved in 20 mL of dichloromethane. The reaction solution was cooled down to 0° C., followed by addition of diisopropyl azodicarboxylate (73 mg, 0.36 mmol), then warmed up to room temperature and stirred for 2 hours. The resulting solution was concentrated under reduced pressure, and the residue was purified by silica gel column chromatography with elution system B to obtain the title compound methyl 2-((S)-6-((2,2',6'-trimethyl-4'-(((S)-tetrahydrofuran-3-yl)oxy)biphenyl-3-yl)methoxy)-2,3-dihydrobenzofuran-3-yl)acetate 12f (100 mg, yield 83.0%) as a white solid.

MS m/z (ESI): 503.4 [M+1]

Step 6

2-((S)-6-((2,2',6'-Trimethyl-4'-(((S)-tetrahydrofuran-3-yl)oxy)biphenyl-3-yl)methoxy)-2,3-dihydrobenzofuran-3-yl)acetic acid Methyl 2-((S)-6-((2,2',6'-trimethyl-4'-(((S)-tetrahydrofuran-3-yl)oxy)biphenyl-3-yl)methoxy)-2,3-dihydrobenzofuran-3-yl)acetate 12f (100 mg, 0.20 mmol) was dissolved in 4 mL of a mixture of the solvents tetrahydrofuran and methanol (V/V=1:1), followed by addition of 2M aqueous lithium hydroxide solution (1 mL, 2 mmol). The reaction solution was stirred for 2 hours. The resulting solution was concentrated under reduced pressure. The residue was mixed with 10 mL of water, 1M hydrochloric acid was added dropwise to adjust the pH to 1~2 and extracted with ethyl acetate (20 mL×2). The combined organic extracts were washed with saturated sodium chloride solution (30 mL), dried with anhydrous magnesium sulphate, and filtered. The filtrate was concentrated under reduced pressure. The residue was purifed using a method of preparative separation to obtain the title compound 2-((S)-6-((2,2',6'-trimethyl-4'-(((S)— tetrahydrofuran-3-yl)oxy)biphenyl-3-yl)methoxy)-2,3-dihydrobenzofuran-3-yl)acetic acid 12 (80 mg, yield 83.0%) as a white solid.

MS m/z (ESI): 487.2 [M−1]

$^1$H NMR (400 MHz, CDCl$_3$) δ 7.41-7.43 (d, 1H), 7.24-7.26 (d, 1H), 7.08-7.10 (d, 1H), 7.02-7.04 (d, 1H), 6.64 (s, 2H), 6.51-6.56 (m, 2H), 5.05 (s, 2H), 4.96-4.4.97 (m, 1H), 4.77-4.81 (m, 1H), 4.30-4.31 (m, 1H), 4.03-4.07 (m, 3H), 3.92-3.97 (m, 1H), 3.83-3.85 (m, 1H), 2.81-2.87 (m, 1H), 2.61-2.68 (m, 1H), 2.20-2.25 (m, 2H), 1.97 (s, 3H), 1.93 (s, 6H), 1.27-1.30 (m, 1H).

Example 13

2-((S)-6-((4'-(((3R,4R)/(3S,4S)-4-Hydroxytetrahydrofuran-3-yl)oxy)-2',6'-dimethylbiphenyl-3-yl)methoxy)-2,3-dihydrobenzofuran-3-yl)acetic acid

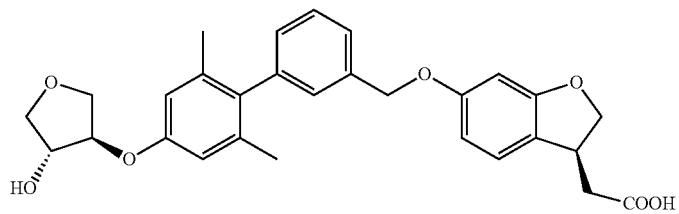

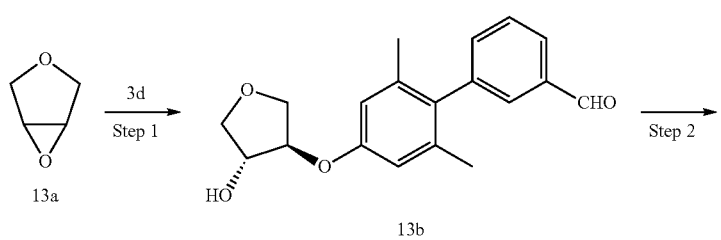

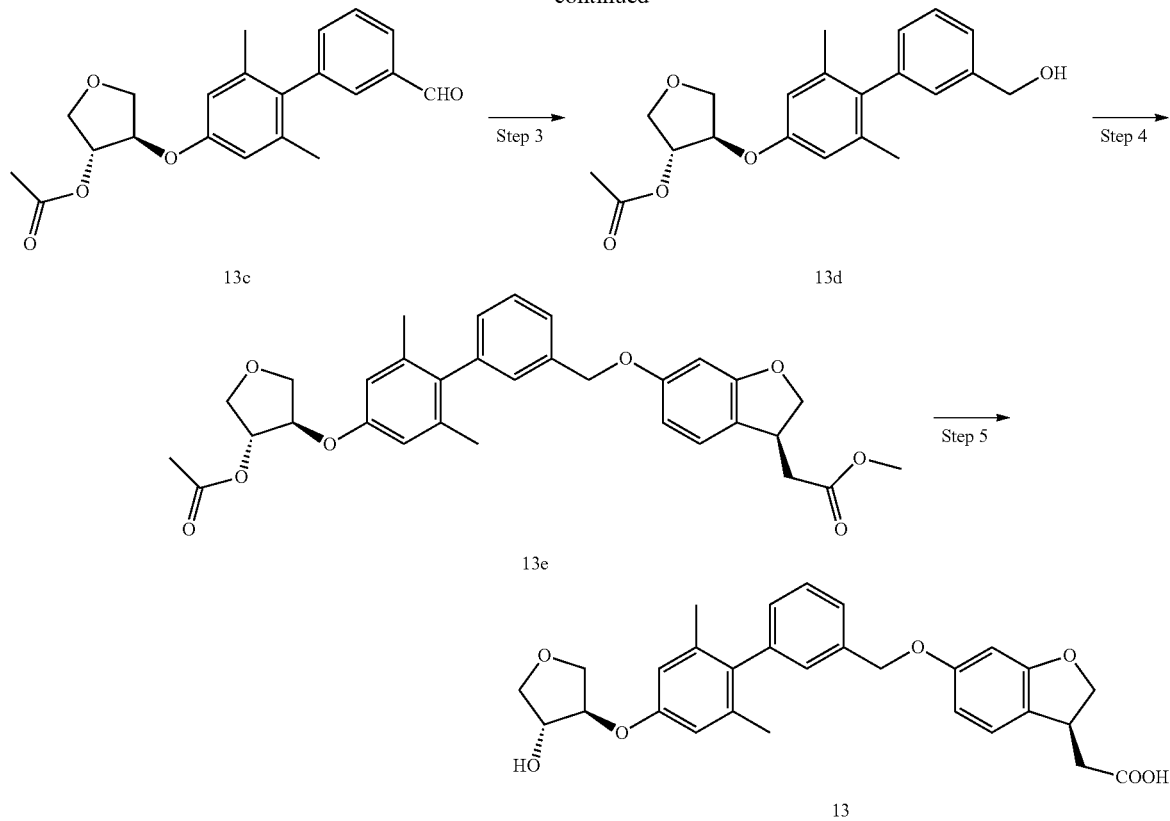

13c  13d

13e

13

Step 1

4'-(((3R,4R)/(3S,4S)-4-Hydroxytetrahydrofuran-3-yl)oxy)-2',6'-dimethylbiphenyl-3-carbaldehyde 4'-Hydroxy-2',6'-dimethylbiphenyl-3-carbaldehyde 3d (226 mg, 1 mmol), 3,4-epoxytetrahydrofuran 13a (600 mg, 6.97 mmol) and potassium carbonate (180 mg, 1.30 mmol) were dissolved in 1 mL of ethanol. The reaction mixture was reacted at 100° C. for 90 minutes under microwave conditions. The resulting mixture was mixed with 10 mL of ethyl acetate, filtered, and washed with ethyl acetate (10 mL×3). The filtrate was concentrated under reduced pressure. The residue was purified by silica gel column chromatography with elution system B to obtain the title compound 4'-(((3R,4R)/(3S,4S)-4-hydroxytetrahydrofuran-3-yl)oxy)-2',6'-dimethylbiphenyl-3-carbaldehyde 13b (312 mg, yield 100%) as a yellow slime.

MS m/z (ESI): 313.1 [M+1]

Step 2

(3R,4R)/(3S,4S)-4-((3'-Formyl-2,6-dimethylbiphenyl-4-yl)oxy)tetrahydrofuran-3-yl acetate 4'-(((3R,4R)/(3S,4S)-4-Hydroxytetrahydrofuran-3-yl)oxy)-2',6'-dimethylbiphenyl-3-carbaldehyde 13b (312 mg, 1 mmol) was dissolved in 5 mL of dichloromethane in an ice bath, followed by addition of triethylamine (0.3 mL, 2 mmol) and acetyl chloride (0.1 mL, 1.50 mmol) successively. The reaction solution was warmed up to room temperature and stirred for 30 minutes. The resulting solution was mixed with 10 mL of water, and extracted with dichloromethane (10 mL×3). The combined organic phase was dried with anhydrous sodium sulfate and filtered. The filtrate was concentrated under the reduced pressure and the residue was purified by silica gel column chromatography with elution system B to obtain the title compound (3R,4R)/(3S,4S)-4-((3'-formyl-2,6-dimethylbiphenyl-4-yl)oxy)tetrahydrofuran-3-ylacetate 13c (280 mg, yield 79.1%) as a colorless slime.

MS m/z (ESI): 372.3 [M+18]

Step 3

(3R,4R)/(3S,4S)-4-((3'-(Hydroxymethyl)-2,6-dimethylbiphenyl-4-yl)oxy)tetrahydrofuran-3-yl acetate (3R,4R)-4-((3'-Formyl-2,6-dimethylbiphenyl-4-yl)oxy)tetrahydrofuran-3-yl acetate 13c (280 mg, 0.79 mmol) was dissolved in 5 mL of methanol. The reaction mixture was cooled down to 0° C., followed by addition of sodium borohydride (45 mg, 1.20 mmol), then warmed up to room temperature and stirred for 30 minutes. The resulting mixture was mixed with 5 mL of acetone, and concentrated under reduced pressure. The residue was mixed with 10 mL of water, separated, and the aqueous phase was extracted with ethyl acetate (20 mL×3). The combined organic phase was washed with saturated sodium chloride solution (10 mL×3), dried with anhydrous sodium sulfate, and filtered. The filtrate was concentrated under reduced pressure and the residue was purified by silica gel column chromatography with elution system B to obtain the title compound (3R,4R)/(3S,4S)-4-((3'-(hydroxymethyl)-2,6-dimethylbiphenyl-4-yl)oxy)tetrahydrofuran-3-yl acetate 13d (200 mg, yield 70.9%) as a colorless slime.

MS m/z (ESI): 357.2 [M+1]

Step 4

Methyl 2-((S)-6-((4'-(((3R,4R)/(3S,4S)-4-acetoxytetrahydrofuran-3-yl)oxy)-2',6'-dimethylbiphenyl-3-yl)methoxy)-2,3-dihydrobenzofuran-3-yl)acetate (3R,4R)/(3S,4S)-4-((3'-(Hydroxymethyl)-2,6-dimethylbiphenyl-4-yl)oxy)tetrahydrofuran-3-yl acetate 13d (200 mg, 0.56 mmol), methyl (S)-2-(6-hydroxyl-2,3-dihydrobenzofuran-3-yl)acetate (117 mg, 0.56 mmol) and triphenylphosphine (221 mg, 0.84 mmol) were dissolved in 5 mL of dichloromethane. The reaction solution was cooled down to 0° C., followed by addition of diisopropyl azodicarboxylate (170 mg, 0.84 mmol). The reaction solution was warmed up to room temperature and stirred for 3 hours. The resulting solution was concentrated under reduced pressure and the residue was purified by silica gel column chromatography with elution system B to obtain the title compound methyl 2-((S)-6-((4'-(((3R,4R)/(3S,4S)-4-acetoxytetrahydrofuran-3-yl)oxy)-2',6'-dimethylbiphenyl-3-yl)methoxy)-2,3-dihydrobenzofuran-3-yl)acetate 13e (200 mg, yield 65.1%) as a colorless slime.

MS m/z (ESI): 564.3 [M+18]

Step 5

2-((S)-6-((4'-(((3R,4R)/(3S,4S)-4-Hydroxytetrahydrofuran-3-yl)oxy)-2',6'-dimethylbiphenyl-3-yl)methoxy)-2,3-dihydrobenzofuran-3-yl)acetic acid Methyl 2-((S)-6-((4'-(((3R,4R)/(3S,4S)-4-acetoxytetrahydrofuran-3-yl)oxy)-2',6'-dimethylbiphenyl-3-yl)methoxy)-2,3-dihydrobenzofuran-3-yl)acetate 13e (200 mg, 0.37 mmol) was dissolved in 4 mL of a mixture of the solvents dichloromethane and methanol (V:V=1:3), followed by addition of 3 M aqueous lithium hydroxide solution (0.5 mL, 1.50 mmol). The reaction solution was stirred for 12 hours. The resulting solution was concentrated under reduced pressure. The residue was mixed with 10 mL of water, 1M hydrochloric acid was added dropwise to adjust the pH to 2-3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure and the residue was purified by silica gel column chromatography with elution system A to obtain the title compound 2-((S)-6-((4'-(((3R,4R)/(3S,4S)-4-hydroxytetrahydrofuran-3-yl)oxy)-2',6'-dimethylbiphenyl-3-yl)methoxy)-2,3-dihydrobenzofuran-3-yl)acetic acid 13 (110 mg, yield 61.4%) as a white solid.

MS m/z (ESI): 508.3 [M+18]

$^1$H NMR (400 MHz, CDCl$_3$) δ 7.40 (m, 2H), 7.16 (s, 1H), 7.06 (m, 2H), 6.66 (s, 2H), 6.48 (m, 2H), 5.06 (s, 2H), 4.76 (m, 2H), 4.47 (d, 1H), 4.29 (m, 2H), 4.07 (dd, 1H), 3.95 (dd, 1H), 3.86 (d, 1H), 3.80 (m, 1H), 2.80 (dd, 1H), 2.61 (dd, 1H), 1.99 (s, 6H).

Example 14

(S)-2-(6-((2',6'-Dimethyl-4'-((1-propionylazetidin-3-yl)oxy)biphenyl-3-yl)methoxy)-2,3-dihydrobenzofuran-3-yl)acetic acid

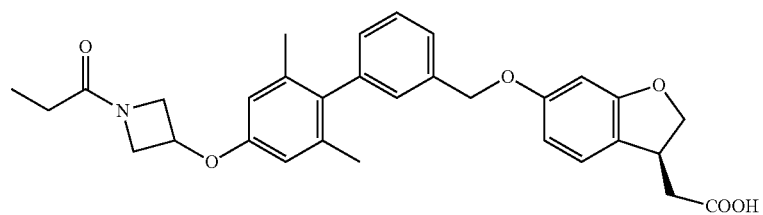

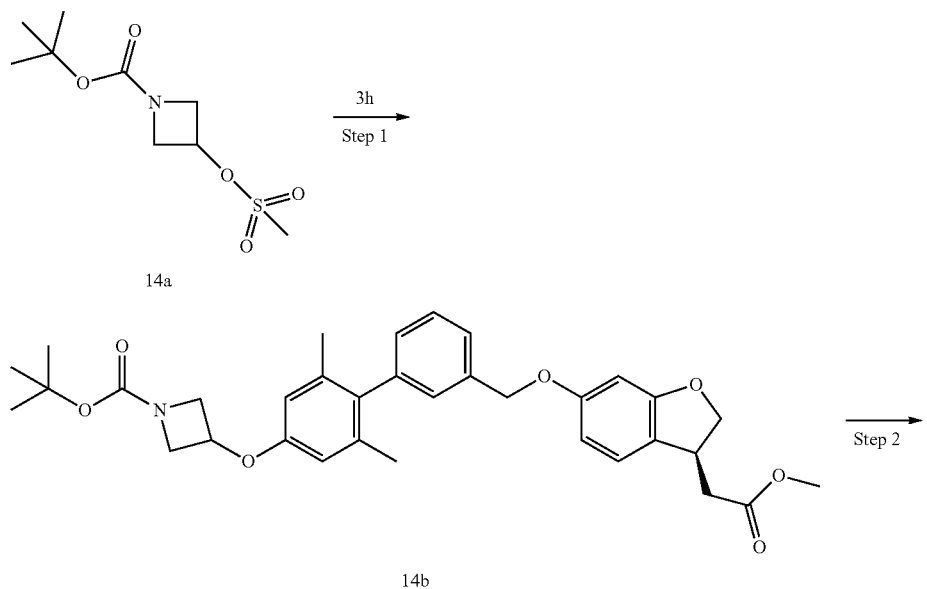

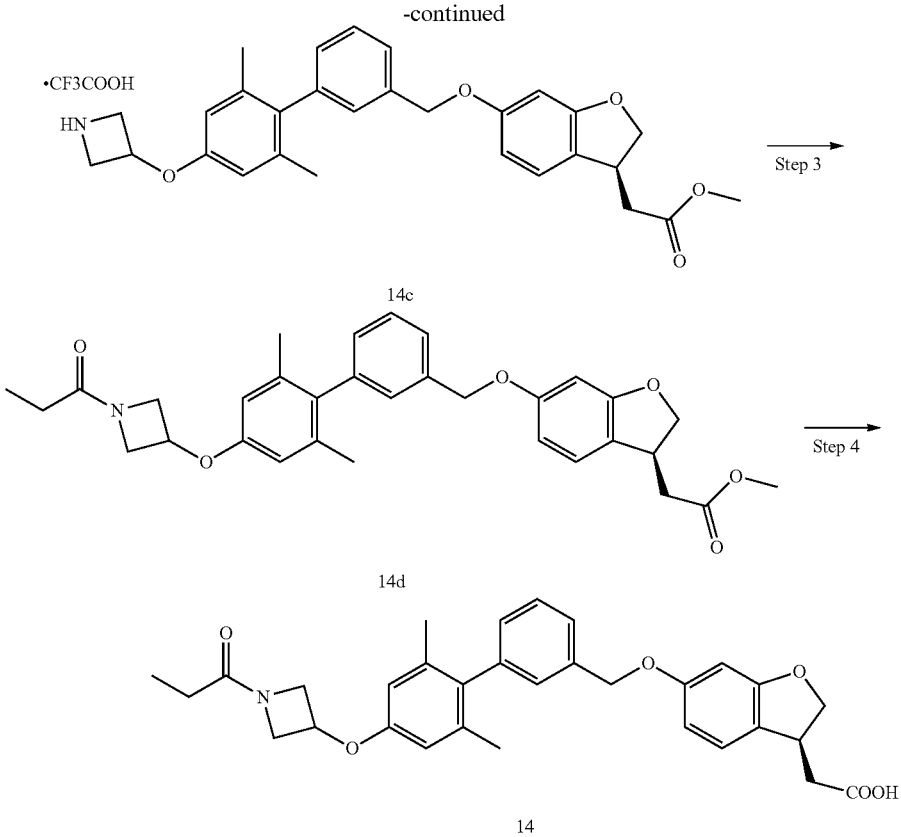

Step 1

(S)-tert-Butyl 3-((3'-(((3-(2-methoxy-2-oxoethyl)-2,3-dihydrobenzofuran-6-yl)oxy)methyl)-2,6-dimethylbiphenyl-4-yl)oxy)azetidine-1-carboxylate tert-Butyl 3-((methylsulfonyl)oxy)azetidine-1-carboxylate 14a (100 mg, 0.40 mmol, prepared by a method disclosed in PCT patent application WO2011097958"), (S)-methyl 2-(6-((4'-hydroxy-2',6'-dimethylbiphenyl-3-yl)methoxy)-2,3-dihydrobenzofuran-3-yl)acetate 3 h (80 mg, 0.19 mmol) and cesium carbonate (130 mg, 0.40 mmol) were dissolved in 10 mL of N,N-dimethylformamide. The reaction solution was heated to 80° C. and stirred for 12 hours. The resulting solution was mixed with 10 mL of water, and extracted with ethyl acetate (30 mL×2). The combined organic extracts were washed with saturated sodium chloride solution (30 mL), dried with anhydrous magnesium sulphate, and filtered. The filtrate was concentrated under reduced pressure and the residue was purified by silica gel column chromatography with elution system B to obtain the title compound (S)-tert-butyl 3-((3'-(((3-(2-methoxy-2-oxoethyl)-2,3-dihydrobenzofuran-6-yl)oxy)methyl)-2,6-dimethylbiphenyl-4-yl)oxy)azetidine-1-carboxylate 14b (60 mg, yield 50.0%) as a colorless oil.

Step 2

(S)-Methyl 2-(6-((4'-(azetidin-3-yloxy)-2',6'-dimethylbiphenyl-3-yl)methoxy)-2,3-dihydrobenzofuran-3-yl)acetate 2,2,2-trifluoroacetate (S)-tert-Butyl 3-((3'-(((3-(2-methoxy-2-oxoethyl)-2,3-dihydrobenzofuran-6-yl)oxy)methyl)-2,6-dimethylbiphenyl-4-yl)oxy)azetidine-1-carboxylate 14b (100 mg, 0.17 mmol) was dissolved in 5 mL of dichloromethane, followed by addition of 1 mL of trifluoroacetic acid. The reaction solution was stirred for 2 hours. The resulting solution was concentrated under reduced pressure to obtain the crude title compound (S)-methyl 2-(6-((4'-(azetidin-3-yloxy)-2',6'-dimethylbiphenyl-3-yl)methoxy)-2,3-dihydrobenzofuran-3-yl)acetate 2,2,2-trifluoroacetate 14c (80 mg) as a brown oil, which was directly used in the next step without further purification.

MS m/z (ESI): 474.2 [M+1]

Step 3

(S)-methyl 2-(6-((2',6'-Dimethyl-4'-((1-propionylazetidin-3-yl)oxy)biphenyl-3-yl)methoxy)-2,3-dihydrobenzofuran-3-yl)acetate The crude (S)-methyl 2-(6-((4'-(azetidin-3-yloxy)-2',6'-dimethylbiphenyl-3-yl)methoxy)-2,3-dihydrobenzofuran-3-yl)acetate 2,2,2-trifluoroacetate 14c (40 mg, 0.09 mmol) was dissolved in 3 mL of dichloromethane, followed by addition of triethylamine (0.1 mL, 0.26 mmol) and propionyl chloride (11 mL, 0.13 mmol) successively. The reaction solution was stirred for 12 hours. The resulting solution was mixed with 10 mL of dichloromethane, washed with saturated sodium chloride solution (5 mL), dried with anhydrous magnesium sulphate, and filtered. The filtrate was concentrated under reduced pressure to obtain the crude title compound (S)-methyl 2-(6-((2',6'-dimethyl-4'-((1-propionylazetidin-3-yl)oxy)biphenyl-3-yl)methoxy)-2,3-dihydrobenzofuran-3-yl)acetate 14d (45 mg) as a yellow oil, which was directly used in the next step without further purification.

MS m/z (ESI): 474.2 [M+1]

Step 4

(S)-2-(6-((2',6'-dimethyl-4'-((1-propionylazetidin-3-yl)oxy)biphenyl-3-yl)methoxy)-2,3-dihydrobenzofuran-3-yl)acetic acid The crude (S)-methyl 2-(6-((2',6'-dimethyl-4'-((1-propionylazetidin-3-yl)oxy)biphenyl-3-yl)methoxy)-2,3-dihydrobenzofuran-3-yl)acetate 14d (45 mg, 0.09 mmol) was dissolved in 3 mL of methanol, followed by addition of 1M aqueous lithium hydroxide solution (0.5 mL, 0.50 mmol). The reaction solution was stirred for 3 hours. To the resulting solution, 1M hydrochloric acid was added dropwise to adjust the pH to 3, 3 mL of water were added, and then the solution was concentrated under reduced pressure and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((2',6'-dimethyl-4'-((1-propionylazetidin-3-yl)oxy)biphenyl-3-yl)methoxy)-2,3-dihydrobenzofuran-3-yl)acetic acid 14 (20 mg, yield 43.0%) as a yellow solid.

MS m/z (ESI): 514.3 [M−1]

$^1$HNMR (400 MHz, CDCl$_3$) δ 7.43-7.34 (m, 2H), 7.16 (s, 1H), 7.08-7.05 (m, 2H), 6.50-6.46 (m, 4H), 5.05 (s, 2H), 5.06-5.03 (m, 1H), 4.82-4.70 (m, 1H), 4.65-4.38 (m, 2H), 4.28-4.16 (m, 3H); 3.87-3.77 (m, 1H); 2.79-2.78 (m, 1H), 2.65-2.62 (m, 1H), 2.19-2.17 (q, 2H), 1.99 (s, 6H), 1.16 (t, 3H).

Example 15

(S)-2-(6-((4'-((1-(Cyclopropanecarbonyl)azetidin-3-yl)oxy)-2',6'-dimethylbiphenyl-3-yl)methoxy)-2,3-dihydrobenzofuran-3-yl)acetic acid

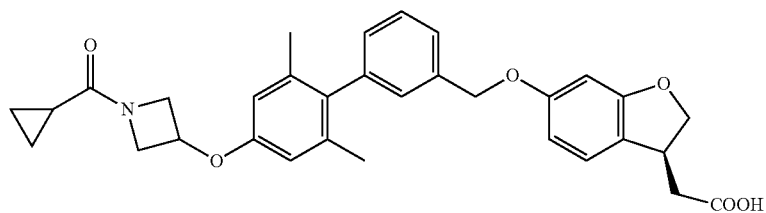

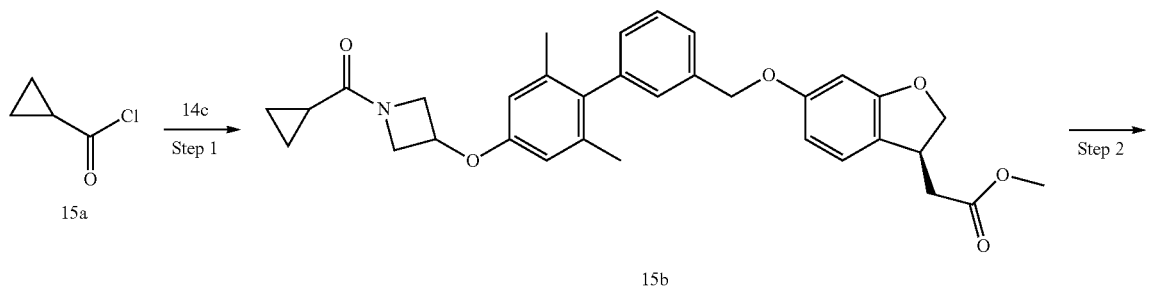

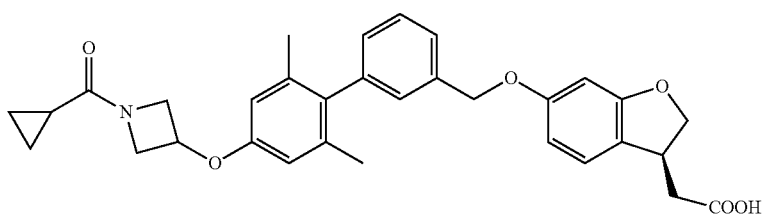

15

Step 1

(S)-Methyl 2-(6-((4'-((1-(cyclopanecarbonyl)
azetidin-3-yl)oxy)-2',6'-dimethylbiphenyl-3-yl)meth-
oxy)-2,3-dihydrobenzofuran-3-yl)acetate The crude (S)-methyl 2-(6-((4'-(azetidin-3-yloxy)-2',6'-dimethylbiphenyl-3-yl)methoxy)-2,3-dihydrobenzofuran-3-yl)acetate 2,2,2-trifluoroacetate 14c (40 mg, 0.09 mmol) was dissolved in 3 mL of dichloromethane, followed by addition of triethylamine (0.1 mL, 0.26 mmol) and cyclopropanecarbonyl chloride 15a (14 mg, 0.13 mmol). The reaction solution was stirred for 12 hours. The resulting solution was mixed with 10 mL of dichloromethane, washed with saturated sodium chloride solution (5 mL), dried with anhydrous magnesium sulphate, filtered, and the filtrate was concentrated under reduced pressure to obtain the crude title compound (S)-methyl 2-(6-((4'-((1-(cyclopropanecarbonyl)azetidin-3-yl)oxy)-2',6'-dimethylbiphenyl-3-yl)methoxy)-2,3-dihydrobenzofuran-3-yl)acetate 15b (46 mg) as a red oil, which was directly used in the next step without further purification.

MS m/z (ESI): 542.2 [M+1]

Step 2

(S)-2-(6-((4'-((1-(Cyclopropanecarbonyl)azetidin-3-yl)oxy)-2',6'-dimethyl-biphenyl-3-yl)methoxy)-2,3-dihydrobenzofuran-3-yl)acetic acid The crude (S)-methyl 2-(6-((4'-((1-(cyclopropanecarbonyl)azetidin-3-yl)oxy)-2',6'-dimethylbiphenyl-3-yl)methoxy)-2,3-dihydrobenzofuran-3-yl)acetate 15b (46 mg, 0.09 mmol) was dissolved in 3 mL of methanol, followed by addition of 1M aqueous lithium hydroxide solution (0.5 mL, 0.50 mmol). The reaction solution was stirred for 3 hours. The resulting solution was concentrated under reduced pressure, 1M hydrochloric acid was added dropwise to adjust the pH to 3, 3 mL of water were added, and then the solution was extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound (S)-2-(6-((4'-((1-(cyclopropanecarbonyl)azetidin-3-yl)oxy)-2',6'-dimethylbiphenyl-3-yl)methoxy)-2,3-dihydrobenzofuran-3-yl)acetic acid 15 (20 mg, yield 44.0%) as a yellow solid.

MS m/z (ESI): 526.3 [M−1]

$^1$H NMR (400 MHz, CDCl$_3$) δ 7.43-7.34 (m, 2H), 7.16 (s, 1H), 7.08-7.05 (m, 2H), 6.50-6.46 (m, 4H), 5.05 (s, 2H), 5.06-5.03 (m, 1H), 4.82-4.70 (m, 1H), 4.65-4.38 (m, 2H), 4.28-4.16 (m, 3H), 3.87-3.77 (m, 1H), 2.79-2.78 (m, 1H), 2.65-2.62 (m, 1H), 1.99 (s, 6H), 1.16 (m, 1H), 0.89 (m, 2H), 0.64 (m, 2H).

Example 16

(S)-2-(6-((4'-(Azetidin-3-yloxy)-2',6'-dimethylbiphenyl-3-yl)methoxy)-2,3-dihydrobenzofuran-3-yl)acetic acid

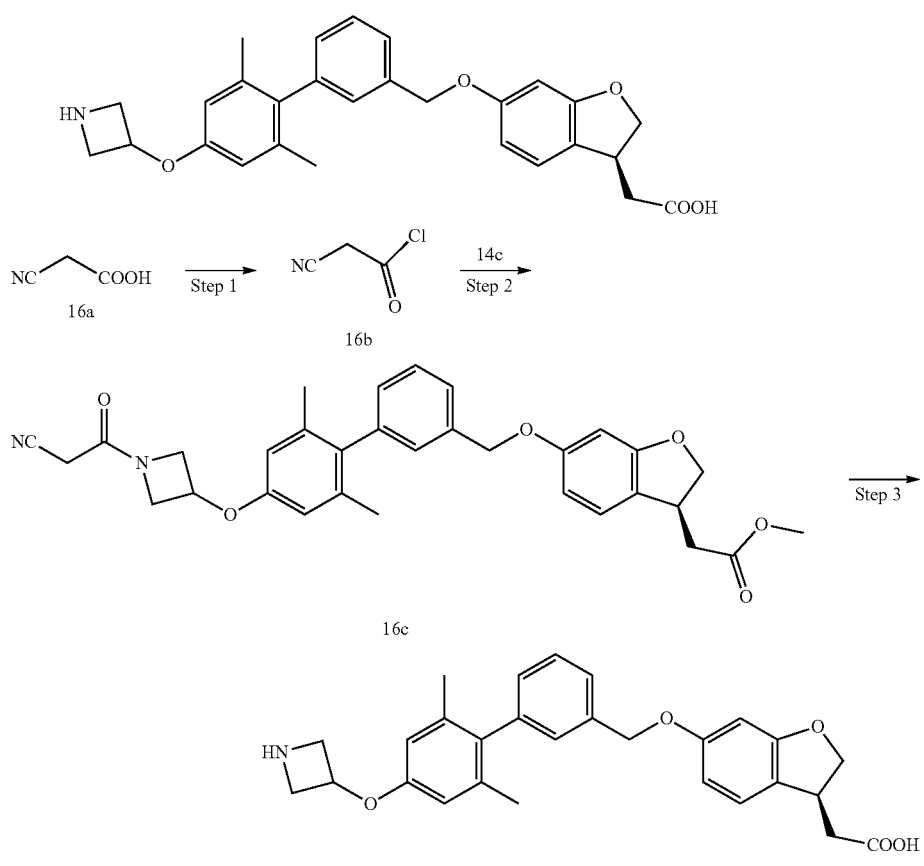

Step 1

2-Cyanoacetyl chloride

2-Cyanoacetic acid 16a (25 mg, 0.30 mmol) was dissolved in 10 mL of dichloromethane, followed by addition of oxalyl chloride (47 mg, 0.45 mmol), and a drop of N,N-dimethylformamide. The reaction solution was stirred for 30 minutes. The resulting solution was concentrated under reduced pressure to obtain the crude 2-cyanoacetyl chloride 16b (30 mg) as a red oil, which was directly used in the next step without further purification.

Step 2

(S)-Methyl 2-(6-((4'-((1-(2-cyanoacetyl)azetidin-3-yl)oxy)-2',6'-dimethylbiphenyl-3-yl)methoxy)-2,3-dihydrobenzofuran-3-yl)acetate (S)-Methyl 2-(6-((4'-(azetidin-3-yloxy)-2',6'-dimethylbiphenyl-3-yl)methoxy)-2,3-dihydrobenzofuran-3-yl)acetate 2,2,2-trifluoroacetate 14c (150 mg, 0.32 mmol) was dissolved in 10 mL of dichloromethane, followed by addition of triethylamine (65 mg, 0.64 mmol) and the crude 2-cyanoacetyl chloride 16b (49 mg, 0.48 mmol). The reaction solution was stirred for 16 hours. The resulting solution was added with 10 mL of water and extracted with ethyl acetate (20 mL×2). The combined organic extracts were washed with saturated sodium chloride solution (5 mL), dried with anhydrous magnesium sulphate, and filtered. The filtrate was concentrated under reduced pressure and the residue was purified by TLC with elution system A to obtain the crude title compound (S)-methyl 2-(6-((4'-((1-(2-cyanoacetyl)azetidin-3-yl)oxy)-2',6'-dimethylbiphenyl-3-yl)methoxy)-2,3-dihydrobenzofuran-3-yl)acetate 16c (80 mg, yield 46.2%) as a yellow solid.
MS m/z (ESI): 558.3 [M+18]

Step 3

(S)-2-(6-((4'-(Azetidin-3-yloxy)-2',6'-dimethylbiphenyl-3-yl)methoxy)-2,3-dihydrobenzofuran-3-yl)acetic acid (S)-Methyl 2-(6-((4'-((1-(2-cyanoacetyl)azetidin-3-yl)oxy)-2',6'-dimethylbiphenyl-3-yl)methoxy)-2,3-dihydrobenzofuran-3-yl)acetate 16c (80 mg, 0.15 mmol) was dissolved in 2 mL of a mixture of the solvents of tetrahydrofuran and methanol (V/V=1:1), followed by addition of 1M aqueous lithium hydroxide solution (1 mL, 1 mmol). The reaction solution was stirred for 2 hours. The resulting solution was concentrated under reduced pressure. The residue was mixed with 10 mL of water, 1M hydrochloric acid was added dropwise to adjust the pH to 3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure. The residue was purified by silica gel column chromatography with elution system B to obtain the title compound (S)-2-(6-((4'-(azetidin-3-yloxy)-2',6'-dimethylbiphenyl-3-yl)methoxy)-2,3-dihydrobenzofuran-3-yl)acetic acid 16 (65 mg, yield 95.6%) as a light yellow solid.

MS m/z (ESI): 458.2 [M-1]

$^1$H NMR (400 MHz, DMSO) δ 7.47-7.43 (m, 1H), 7.41-7.37 (m, 1H), 7.15-7.09 (m, 2H), 7.05 (d, 1H), 6.63 (s, 2H), 6.50-6.43 (m, 2H), 5.10 (s, 2H), 5.07-5.03 (m, 1H), 4.73-4.65 (m, 1H), 4.50-4.41 (m, 2H), 4.22-4.15 (m, 1H), 4.01-3.96 (m, 2H), 3.74-3.62 (m, 1H), 2.75-2.65 (m, 1H), 2.50-2.43 (m, 1H), 1.93 (s, 6H).

Example 17

2-((S)-6-((4'-(((1R,2R)/(1S,2S)-2-Hydroxycyclopentyl)oxy)-2',6'-dimethylbiphenyl-3-yl)methoxy)-2,3-dihydrobenzofuran-3-yl)acetic acid

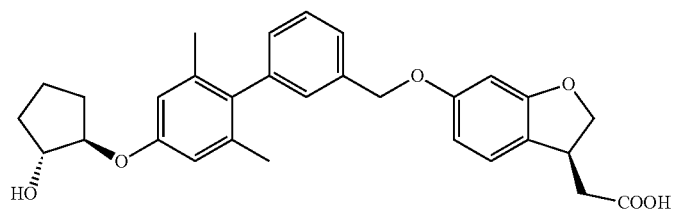

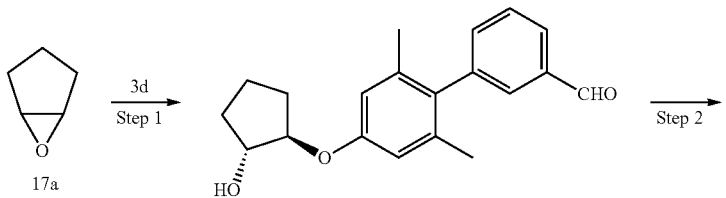

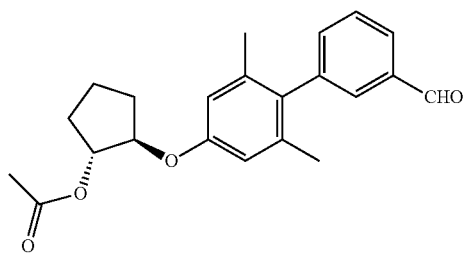

17c

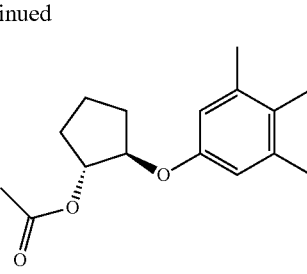

17d

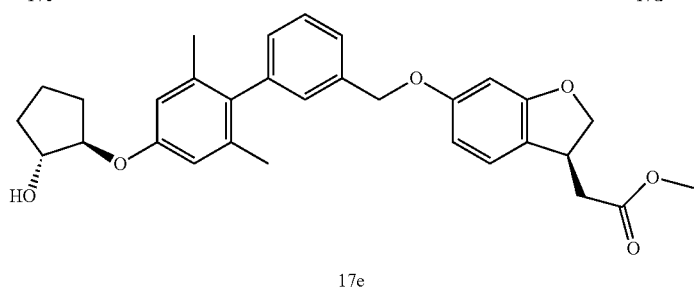

17e

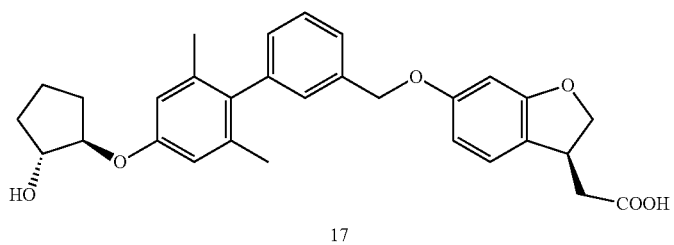

17

Step 1

4'-(((1R,2R)/(1S,2S)-2-Hydroxycyclopentyl)oxy)-2',6'-dimethylbiphenyl-3-carbaldehyde 4'-Hydroxy-2',6'-dimethylbiphenyl-3-carbaldehyde 3d (113 mg, 0.50 mmol), 1,2-epoxycyclopentane 17a (300 mg, 3.57 mmol) and potassium carbonate (90 mg, 0.65 mmol) were dissolved in 0.5 mL of ethanol. The reaction mixture was reacted at 100° C. for 75 minutes under microwave condition. The resulting mixture was mixed with 15 mL of ethyl acetate and filtered. The filtrate was washed with water (10 mL×3), dried with anhydrous sodium sulfate, and filtered. The filtrate was concentrated under reduced pressure to obtain the crude title compound 4'-(((1R,2R)/(1S,2S)-2-hydroxycyclopentyl)oxy)-2',6'-dimethylbiphenyl-3-carbaldehyde 17b (180 mg) as a yellow slime, which was directly used in the next step without further purification.

MS m/z (ESI): 311.3 [M+1]

Step 2

(1R,2R)/(1S,2S)-2-((3'-Formyl-2,6-dimethylbiphenyl-4-yl)oxy)cyclopentyl acetate

The crude 4'-(((1R,2R)/(1S,2S)-2-Hydroxycyclopentyl)oxy)-2',6'-dimethylbiphenyl-3-carbaldehyde 17b (155 mg, 0.50 mmol) was dissolved in 15 mL of dichloromethane. To the reaction solution triethylamine (0.1 mL, 1 mmol) and acetyl chloride (61 mg, 0.60 mmol) were added successively. The reaction solution was stirred for 2 hours. The resulting solution was mixed with 10 mL of dichloromethane, washed with water (10 mL×3), dried with anhydrous sodium sulfate, and filtered. The filtrate was concentrated under reduced pressure and the residue was purified by elution system B to obtain the title compound (1R,2R)/(1S,2S)-2-((3'-formyl-2,6-dimethylbiphenyl-4-yl)oxy)cyclopentyl acetate 17c (71 mg, yield 40.3%) as a white solid.

Step 3

(1R,2R)/(1S,2S)-2-((3'-(hydroxymethyl)-2,6-dimethylbiphenyl-4-yl)oxy)cyclopentyl acetate (1R,2R)/(1S,2S)-2-((3'-Formyl-2,6-dimethylbiphenyl-4-yl)oxy)cyclopentyl acetate 17c (71 mg, 0.20 mmol) was dissolved in 10 mL of methanol, followed by addition of sodium borohydride (15 mg, 0.40 mmol). The reaction solution was stirred for 2 hours. The resulting solution was mixed with 6 mL of acetone and concentrated under reduced pressure. The residue was purified by silica gel column chromatography with elution system B to obtain the title compound (1R,2R)/(1S,2S)-2-((3'-(hydroxymethyl)-2,6-dimethylbiphenyl-4-yl)oxy)cyclopentyl acetate 17d (61 mg, yield 85.2%) as a colorless slime.

MS m/z (ESI): 355.3 [M+1]

Step 4

Methyl 2-((S)-6-((4'-(((1R,2R)/(1S,2S)-2-hydroxycyclopentyl)oxy)-2',6'-dimethylbiphenyl-3-yl)methoxy)-2,3-dihydrobenzofuran-3-yl)acetate (1R,2R)/(1S,2S)-2-((3'-(Hydroxymethyl)-2,6-dimethylbiphenyl-4-yl)oxy) cyclopentyl acetate 17d (61 mg, 0.17 mmol), methyl (S)-2-(6-hydroxyl-2,3-dihydrobenzofuran-3- yl)acetate (36 mg, 0.17 mmol) and triphenylphosphine (68 mg, 0.26 mmol) were dissolved in 10 mL of dichloromethane. The reaction solution was cooled down to 0° C., followed by addition of diisopropyl azodicarboxylate (53 mg, 0.26 mmol). The reaction solution was warmed up to room temperature and stirred for 1.5 hours. The resulting solution was concentrated under reduced pressure and the residue was purified by silica gel column chromatography with elution system B to obtain the title compound methyl 2-((S)-6-((4'-(((1R,2R)/(1S,2S)-2-hydroxycyclopentyl)oxy)-2',6'-dimethylbiphenyl-3-yl)methoxy)-2,3-dihydrobenzofuran-3-yl)acetate 17e (64 mg, yield 69.0%) as a colorless slime.

MS m/z (ESI): 520.4 [M+18]

Step 5

2-((S)-6-((4'-(((1R,2R)/(1S,2S)-2-Hydroxycyclopentyl)oxy)-2',6'-dimethylbiphenyl-3-yl)methoxy)-2,3-dihydrobenzofuran-3-yl)acetic acid Methyl 2-((S)-6-((4'-(((1R,2R)/(1S,2S)-2-hydroxycyclopentyl)oxy)-2',6'-dimethylbiphenyl-3-yl)methoxy)-2,3-dihydrobenzofuran-3-yl)acetate 17e (54 mg, 0.10 mmol) was dissolved in 10 mL of methanol, followed by addition of 2M aqueous lithium hydroxide solution (0.5 mL, 1 mmol). The reaction solution was stirred for 2 hours. The resulting solution was concentrated under reduced pressure. The residue was mixed with 3 mL of water, 1M citric acid was added dropwise to adjust the pH to 2-3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the title compound 2-((S)-6-(((4'-((1R,2R)/(1S,2S)-2-hydroxycyclopentyl)oxy)-2',6'-dimethylbiphenyl-3-yl)methoxy)-2,3-dihydrobenzofuran-3-yl)acetic acid 17 (21 mg, yield 43.0%) as a light yellow solid.

MS m/z (ESI): 506.4 [M+18]

$^1$H NMR (400 MHz, CDCl$_3$) δ 7.41-7.48 (m, 2H), 7.22 (s, 1H), 7.04-7.14 (m, 2H), 6.66 (s, 2H), 6.51-6.55 (m, 2H), 5.10 (s, 2H), 4.78-4.83 (s, 1H), 3.96-3.99 (m, 1H), 3.72-3.86 (m, 1H), 2.83-2.88 (m, 1H), 2.63-2.69 (m, 1H), 2.24-2.76 (m, 2H), 2.03 (s, 6H), 1.96-2.06 (m, 2H), 1.61-1.86 (m, 2H), 1.46-1.56 (m, 2H).

Example 18

2-((S)-6-((4-Fluoro-2',6'-dimethyl-4'-(((S)-tetrahydrofuran-3-yl)oxy)biphenyl-3-yl)methoxy)-2,3-dihydrobenzofuran-3-yl)acetic acid

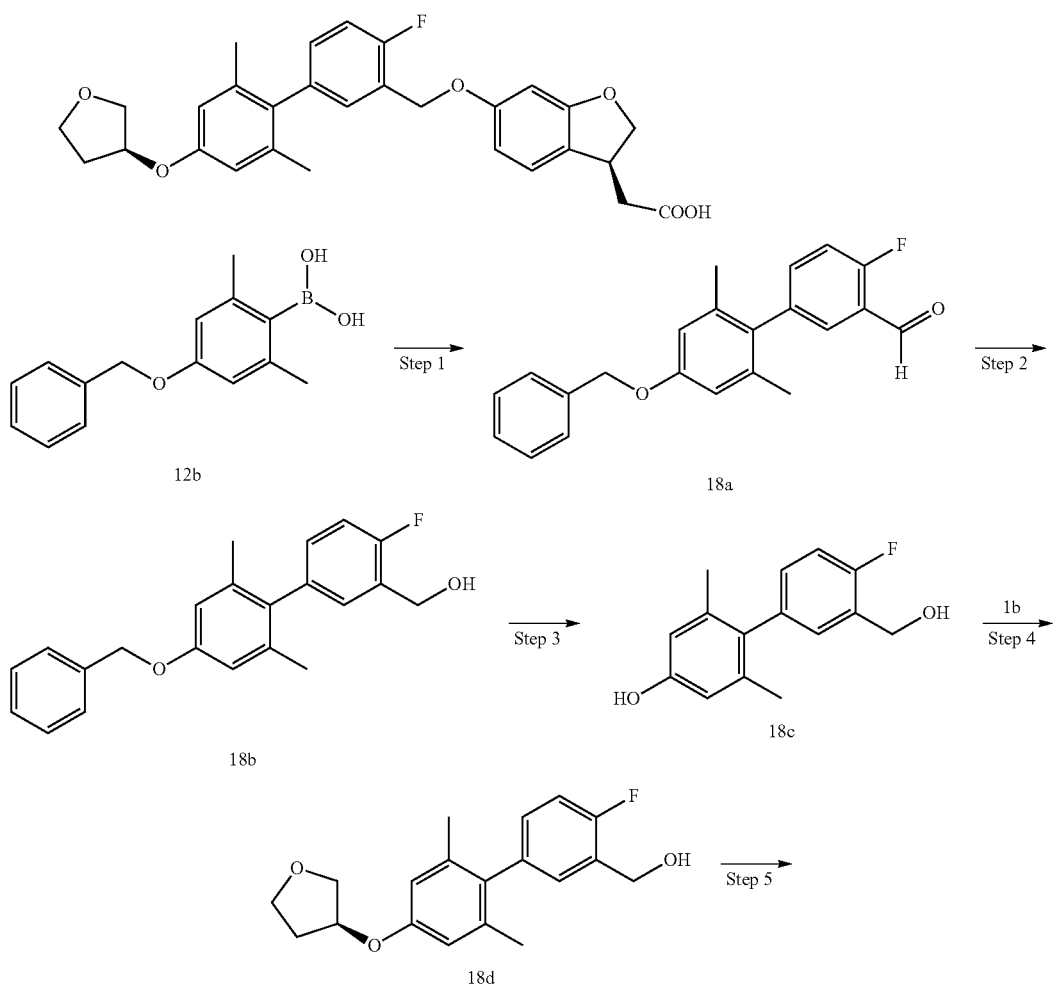

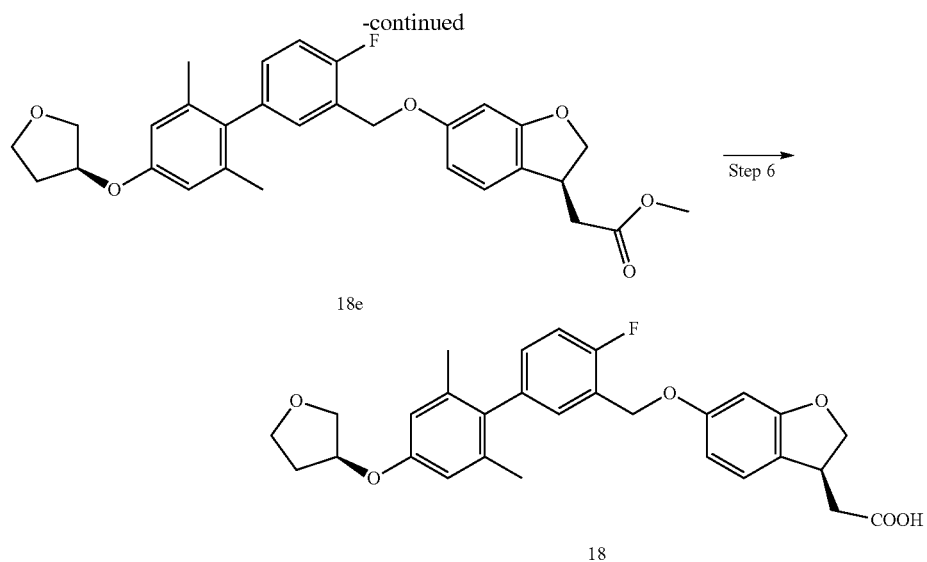

Step 1

4'-(Benzyloxy)-4-fluoro-2',6'-dimethylbiphenyl-3-carbaldehyde (4-(Benzyloxy)-2,6-dimethylphenyl)boronic acid 12b (256 mg, 1 mmol), 2-fluoro-5-bromo-benzaldehyde (203 mg, 1 mmol), 2M aqueous sodium carbonate solution (1 mL, 2 mmol), 2-dicyclohexylphosphino-2',6'-dimethoxybiphenyl (37 mg, 0.08 mmol) and tris(dibenzylideneacetone)dipalladium (18 mg, 0.02 mmol) were dissolved in 3 mL of a mixture of the solvents ethylene glycol dimethyl ether and toluene (V/V=1:2). The reaction mixture was heated at 100° C. for 2 hours, and then at 120° C. for 0.5 hours under microwave conditions. The resulting mixture was mixed with 10 mL of water and extracted with ethyl acetate (10 mL×3). The combined organic extracts were washed with saturated sodium chloride solution (30 mL), dried with anhydrous magnesium sulphate, and filtered. The filtrate was concentrated under reduced pressure. The residue was purified by silica gel column chromatography with elution system B to obtain the title compound 4'-(benzyloxy)-4-fluoro-2',6'-dimethylbiphenyl-3-carbaldehyde 18a (390 mg, yield 58.4%) as a colorless slime.

MS m/z (ESI): 335.2 [M+1]

Step 2

(4'-(Benzyloxy)-4-fluoro-2',6'-dimethylbiphenyl-3-yl)methanol

4'-(Benzyloxy)-4-fluoro-2',6'-dimethylbiphenyl-3-carbaldehyde 18a (390 mg, 1.17 mmol) were dissolved in 5 mL of methanol, followed by addition of sodium borohydride (66 mg, 1.75 mmol). The reaction solution was stirred for 30 minutes. The resulting solution was mixed with 10 mL of acetone and concentrated under reduced pressure. The residue was mixed with 10 mL of water and extracted with ethyl acetate (10 mL×3). The combined organic extracts were washed with saturated sodium chloride solution (30 mL), dried with anhydrous magnesium sulphate, and filtered. The filtrate was concentrated under reduced pressure to obtain the crude title compound (4'-(benzyloxy)-4-fluoro-2',6'-dimethylbiphenyl-3-yl)methanol 18b (370 mg) as a colorless slime, which was directly used in the next step without further purification.

Step 3

4'-Fluoro-3'-(hydroxymethyl)-2,6-dimethylbiphenyl-4-ol

The crude (4'-(benzyloxy)-4-fluoro-2',6'-dimethylbiphenyl-3-yl)methanol 18b (370 mg, 1.10 mmol) was dissolved in 5 mL of methanol, followed by addition of Pd/C (40 mg, 10%) under hydrogen atomosphere. The reaction mixture was stirred for 12 hours. The resulting mixture was filtered. The filtrate was concentrated under reduced pressure and the residue was purified by silica gel column chromatography with elution system B to obtain the title compound 4'-fluoro-3'-(hydroxymethyl)-2,6-dimethylbiphenyl-4-ol 18c (225 mg, yield 83.3%) as a white solid.

MS m/z (ESI): 245.2 [M−1]

Step 4

(S)-(4-Fluoro-2',6'-dimethyl-4'-((tetrahydrofuran-3-yl)oxy)biphenyl-3-yl)methanol The crude (R)-tetrahydrofuran-3-yl methanesulfonate 1b (83 mg, 0.50 mmol), 4'-fluoro-3'-(hydroxymethyl)-2,6-dimethylbiphenyl-4-ol 18c (110 mg, 0.45 mmol) and cesium carbonate (293 mg, 0.90 mmol) were dissolved in 2 mL of N,N-dimethylformamide. The reaction mixture was heated to 90° C. and stirred for 12 hours. The resulting mixture was concentrated under reduced pressure, mixed with 10 mL of water and extracted with ethyl acetate (10 mL×3). The combined organic extracts were washed with saturated sodium chloride solution (30 mL), dried with anhydrous magnesium sulphate, and filtered. The filtrate was concentrated under reduced pressure to obtain the crude title compound (S)-(4-fluoro-2',6'-dimethyl-4'-((tetrahydrofuran-3-yl)oxy)biphenyl-3-yl)methanol 18d (150 mg) as a colorless slime, which was directly used in the next step without further purification.

MS m/z (ESI): 317.1 [M+1]

Step 5

Methyl 2-((S)-6-((4-fluoro-2',6'-dimethyl-4'-(((S)-tetrahydrofuran-3-yl)oxy)biphenyl-3-yl)methoxy)-2,3-dihydrobenzofuran-3-yl)acetate The crude (S)-(4-fluoro-2',6'-dimethyl-4'-((tetrahydrofuran-3-yl)oxy)biphenyl-3-yl)methanol 18d (150 mg, 0.45 mmol), methyl (S)-2-(6-hydroxyl-2,3-dihydrobenzofuran-3-yl)acetate (94 mg, 0.45 mmol) and triphenylphosphine (177 mg, 0.68 mmol) were dissolved in 5 mL of dichloromethane. The reaction solution was cooled down to 0° C., followed by addition of diisopropyl azodicarboxylate (136 mg, 0.68 mmol). The reaction solution was warmed up to room temperature and stirred for 12 hours. The resulting solution was concentrated under reduced pressure and the residue was purified by silica gel column chromatography with elution system B to obtain the title compound methyl 2-((S)-6-((4-fluoro-2',6'-dimethyl-4'-(((S)-tetrahydrofuran-3-yl)oxy)biphenyl-3-yl)methoxy)-2,3-dihydrobenzofuran-3-yl)acetate 18e (150 mg, yield 65.8%) as a colorless slime.

MS m/z (ESI): 507.2 [M+1]

Step 6

2-((S)-6-((4-Fluoro-2',6'-dimethyl-4'-(((S)-tetrahydrofuran-3-yl)oxy)biphenyl-3-yl)methoxy)-2,3-dihydrobenzofuran-3-yl)acetic acid Methyl 2-((S)-6-((4-fluoro-2',6'-dimethyl-4'-(((S)-tetrahydrofuran-3-yl)oxy) biphenyl-3-yl)methoxy)-2,3-dihydrobenzofuran-3-yl)acetate 18e (150 mg, 0.30 mmol) was dissolved in 4.5 mL of a mixture of the solvents tetrahydrofuran, methanol and water (V/V=1:3:0.5), followed by addition of 1M aqueous lithium hydroxide solution (1 mL, 1 mmol). The reaction solution was stirred for 12 hours. The resulting solution was concentrated under reduced pressure. The residue was mixed with 10 mL of water, 2M hydrochloric acid was added dropwise to adjust the pH to 2~3, and extracted with ethyl acetate (20 mL×2). The combined organic extracts were washed with saturated sodium chloride solution (30 mL), dried with anhydrous magnesium sulphate and filtered. The filtrate was concentrated under reduced pressure and the residue was purified by TLC with elution system A to obtain the title compound 2-((S)-6-((4-fluoro-2',6'-dimethyl-4'-(((S)-tetrahydrofuran-3-yl)oxy)biphenyl-3-yl)methoxy)-2,3-dihydrobenzofuran-3-yl)acetic acid 18 (100 mg, yield 66.7%) as a white solid.

MS m/z (ESI): 491.3 [M−1]

$^1$H NMR (400 MHz, CDCl$_3$) δ 7.23 (dd, 1H), 7.14-7.04 (m, 3H), 6.60 (s, 2H), 6.50-6.45 (m, 2H), 5.13 (s, 2H), 4.94 (m, 1H), 4.76 (t, 1H), 4.28 (dd, 1H), 4.02-3.89 (m, 4H), 3.80 (m, 1H), 2.80 (dd, 1H), 2.61 (dd, 1H), 2.20 (m, 2H), 1.96 (s, 6H).

Example 19

2-((S)-6-((3'-Fluoro-2',6'-dimethyl-4'-(((S)-tetrahydrofuran-3-yl)oxy)biphenyl-3-yl)methoxy)-2,3-dihydrobenzofuran-3-yl)acetic acid

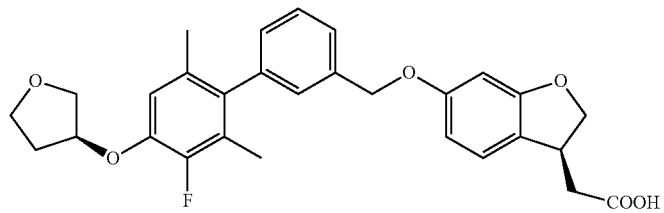

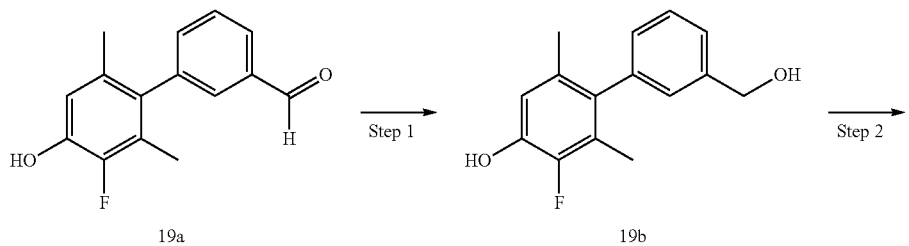

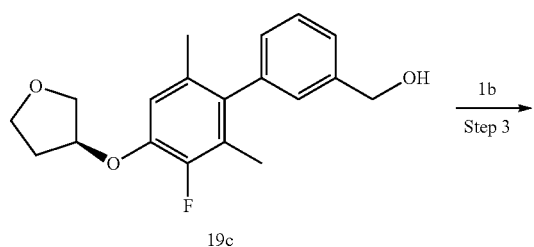

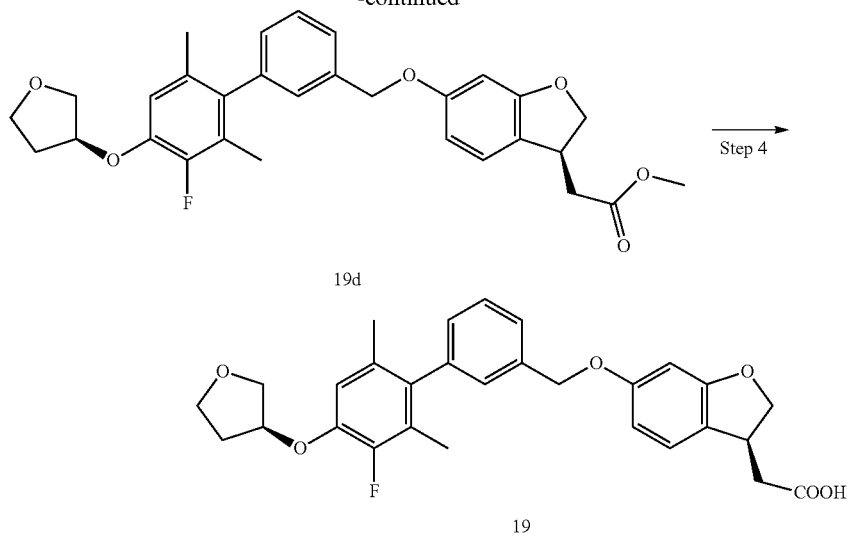

19d

19

Step 1

3-Fluoro-3'-(hydroxymethyl)-2,6-dimethylbiphenyl-4-ol

3'-Fluoro-4'-hydroxy-2',6'-dimethylbiphenyl-3-carbaldehyde 19a (700 mg, 2.87 mmol, prepared by a method disclosed in PCT patent application WO2008001931) was dissolved in 10 mL of methanol, followed by addition of sodium borohydride (130 mg, 3.44 mmol). The reaction solution was stirred for 2 hours. The resulting solution was concentrated under reduced pressure. The residue was mixed with 10 mL of water and extracted with ethyl acetate (50 mL×2). The combined organic extracts were washed with saturated sodium chloride solution (30 mL), dried with anhydrous magnesium sulphate, and filtered. The filtrate was concentrated under reduced pressure to obtain the crude title compound 3-fluoro-3'-(hydroxymethyl)-2,6-dimethylbiphenyl-4-ol 19b (700 mg) as a white solid, which was used directly in the next step without further purification.

MS m/z (ESI): 247.1 [M+1]

Step 2

(S)-(3'-Fluoro-2',6'-dimethyl-4'-((tetrahydrofuran-3-yl)oxy)biphenyl-3-yl)methanol The crude (R)-tetrahydrofuran-3-yl methanesulfonate 1b (202 mg, 1.22 mmol), the crude 3-fluoro-3'-(hydroxymethyl)-2,6-dimethylbiphenyl-4-ol 19b (200 mg, 0.81 mmol) and cesium carbonate (527 mg, 1.62 mmol) were dissolved in 5 mL of N,N-dimethylformamide. The reaction mixture was heated to 80° C. and stirred for 12 hours. The resulting mixture was mixed with 20 mL of water and extracted with ethyl acetate (30 mL×2). The combined organic phase was washed with water (30 mL) and saturated sodium chloride solution (30 mL) successively, dried with anhydrous magnesium sulphate, and filtered. The filtrate was concentrated under reduced pressure. The residue was purified by silica gel column chromatography with elution system B to obtain the title compound (S)-(3'-fluoro-2',6'-dimethyl-4'-((tetrahydrofuran-3-yl)oxy)biphenyl-3-yl)methanol 19c (130 mg, yield 50.8%) as a colorless slime.

MS m/z (ESI): 334.2 [M+18]

Step 3

Methyl 2-((S)-6-((3'-fluoro-2',6'-dimethyl-4'-(((S)-tetrahydrofuran-3-yl)oxy)biphenyl-3-yl)methoxy)-2,3-dihydrobenzofuran-3-yl)acetate (S)-(3'-Fluoro-2',6'-dimethyl-4'-((tetrahydrofuran-3-yl)oxy)biphenyl-3-yl)methanol 19c (130 mg, 0.41 mmol), methyl (S)-2-(6-hydroxyl-2,3-dihydrobenzofuran-3-yl)acetate (85 mg, 0.41 mmol) and triphenylphosphine (161 mg, 0.62 mmol) were dissolved in 10 mL of dichloromethane, followed by addition of diisopropyl azodicarboxylate (125 mg, 0.62 mmol). The reaction solution was stirred for 2 hours. The resulting solution was concentrated under reduced pressure and the residue was purified by silica gel column chromatography with elution system B to obtain the title compound methyl 2-((S)-6-((3'-fluoro-2',6'-dimethyl-4'-(((S)-tetrahydrofuran-3-yl)oxy)biphenyl-3-yl)methoxy)-2,3-dihydrobenzofuran-3-yl)acetate 19d (150 mg, yield 72.5%) as a colorless oil.

MS m/z (ESI): 507.2 [M+1]

Step 4

2-((S)-6-((3'-Fluoro-2',6'-dimethyl-4'-(((S)-tetrahydrofuran-3-yl)oxy)biphenyl-3-yl)methoxy)-2,3-dihydrobenzofuran-3-yl)acetic acid Methyl 2-((S)-6-((3'-fluoro-2',6'-dimethyl-4'-(((S)-tetrahydrofuran-3-yl)oxy) biphenyl-3-yl)methoxy)-2,3-dihydrobenzofuran-3-yl)acetate 19d (150 mg, 0.30 mmol) was dissolved in 4 mL of a mixture of the solvents of methanol and tetrahydrofuran (V/V=1:1), followed by addition of 1M aqueous lithium hydroxide solution (1.5 mL, 1.50 mmol). The reaction solution was stirred for 2 hours. The resulting solution was concentrated under reduced pressure, mixed with 10 mL of water, 1M hydrochloric acid was added dropwise to adjust the pH to 2~3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure, and the residue was purified by TLC with elution system A to obtain the title compound 2-((S)-6-(((3'-fluoro-2',6'-dimethyl-4'-(((S)-tetrahydrofuran-3-yl)oxy)biphenyl-3-yl)methoxy)-2,3-dihydrobenzofuran-3-yl)acetic acid 19 (85 mg, yield 57.8%) as a white solid.

MS m/z (ESI): 491.2 [M−1]

$^1$H NMR (400 MHz, CDCl$_3$) δ 7.52-7.41 (m, 2H), 7.19 (s, 1H), 7.10 (d, 2H), 6.70 (d, 1H), 6.58-6.52 (m, 1H), 6.51 (s, 1H), 5.10 (s, 2H), 5.07-4.96 (m, 2H), 4.83-4.78 (m, 1H), 4.38-4.29 (m, 1H), 4.14-4.05 (m, 3H), 4.02-3.95 (m, 1H), 2.90-2.79 (m, 1H), 2.70-2.60 (m, 1H), 2.31-2.20 (m, 2H), 2.00 (s, 3H), 1.96 (d, 3H).

Compounds of Examples 20-24 were prepared using the appropriate reactants according to the processes of Examples 3 and 5.

Example No., structure and characterization data are listed below:

| No. | Structure | Properties | MS | HNMR |
|---|---|---|---|---|
| 20 | 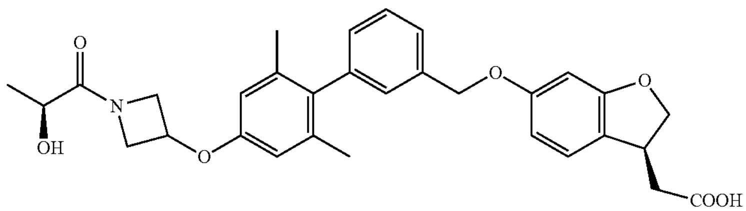 [SMILES: Cc1cc(OC2CN(C(=O)[C@H](C)O)C2)cc(C)c1-c1cccc(COc2ccc3c(c2)OC[C@H]3CC(=O)O)c1] | a white solid | 532.4 [M + 1] | $^1$H NMR (400 MHz, CDCl$_3$) δ 7.47-7.34 (m, 2H), 7.15 (s, 1H), 7.06 (s, 2H), 6.47-6.42 (m, 4H), 5.05 (s, 2H), 5.06-5.03 (m, 1H), 4.82-4.70 (m, 1H), 4.65-4.38 (m, 2H), 4.28-4.16 (m, 4H), 3.87-3.77 (m, 1H), 2.87-2.72 (m, 1H), 2.66-2.51 (m, 1H), 1.98 (s, 6H), 1.36 (d, 3H). |
| 21 | 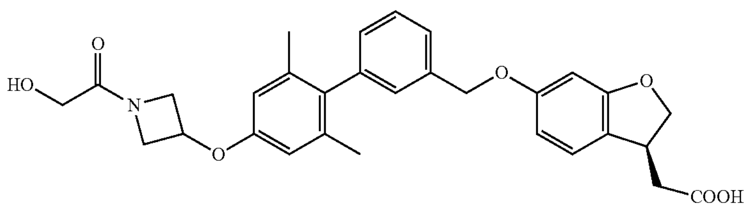 [SMILES: Cc1cc(OC2CN(C(=O)CO)C2)cc(C)c1-c1cccc(COc2ccc3c(c2)OC[C@H]3CC(=O)O)c1] | a white solid | 518.3 [M + 1] | $^1$H NMR (400 MHz, CDCl$_3$) δ 7.47-7.34 (m, 2H), 7.16 (s, 1H), 7.12-6.99 (m, 2H), 6.52-645. (s, 4H), 5.06 (s, 2H), 5.05-5.03 (m, 1H), 4.79-4.73 (m, 1H), 4.57-4.43 (m, 2H), 4.35-4.23 (m,1H), 4.22-4.13 (m, 2H), 4.07 (s, 2H), 3.87-3.77 (m, 1H), 2.85-2.75 (m, 1H), 2.67-2.58 (m, 1H), 1.98 (s, 6 H). |
| 22 | 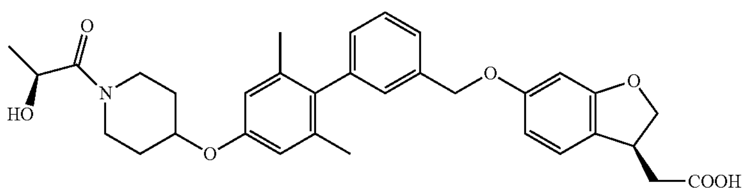 [SMILES: Cc1cc(OC2CCN(C(=O)[C@H](C)O)CC2)cc(C)c1-c1cccc(COc2ccc3c(c2)OC[C@H]3CC(=O)O)c1] | a white solid | 558.2 [M − 1] | $^1$H NMR (400 MHz, CDCl$_3$) δ 7.47-7.37 (m, 2H), 7.17 (s, 1H), 7.09-7.04 (m, 2H), 6.67 (s, 2H), 6.51-6.46 (m, 2H), 5.06 (s, 2H), 5.04-4.94 (m, 1H), 4.79-4.74 (m, 1H), 4.65-4.57 (m, 1H), 4.57-4.49 (m, 1H), 4.32-4.25 (m, 1H), 3.86-3.76 (m, 2H), 3.73-3.64 (m, 1H), 3.44-3.36 (m, 1H), 2.85-2.74 (m, 1H), 2.65-2.56 (m, 1H), 1.99 (s, 6H), 1.93 (s, 4H), 1.36 (d, 3H). |
| 23 | 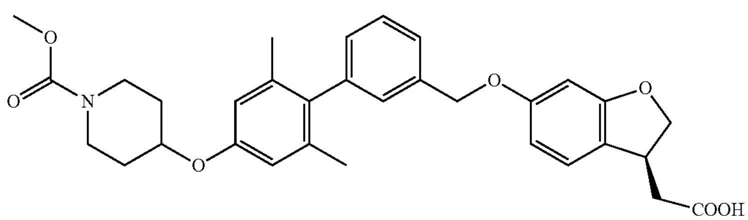 [SMILES: COC(=O)N1CCC(Oc2cc(C)c(-c3cccc(COc4ccc5c(c4)OC[C@H]5CC(=O)O)c3)c(C)c2)CC1] | a white solid | 544.3 [M − 1] | $^1$H NMR (400 MHz, CDCl$_3$) δ 7.47-7.33 (m, 2H), 7.18(s, 1H), 7.11-7.03 (m, 2H), 6.70 (s, 2H), 6.54-6.44 (m, 2H), 5.10 (s, 2H), 4.83-4.70 (m, 1H), 4.55-4.47 (m, 1H), 4.33-4.24 (m, 1H), 3.85-3.74 (m, 3H), 3.72 (s, 3H), 3.53-3.41 (m, 2H), 2.86-2.76 (m, 1H), 2.67-2.56 (m, 1H), 1.98 (s, 6H), 1.97-1.89 (m, 2H), 1.86-1.74 (m, 2H). |
| 24 | 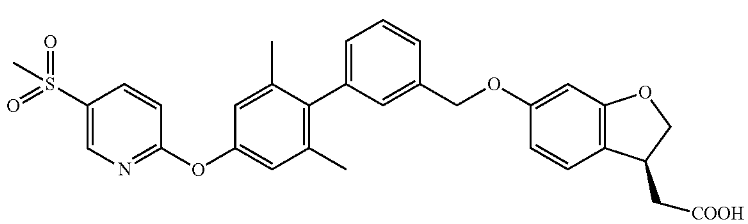 [SMILES: Cc1cc(Oc2ccc(S(C)(=O)=O)cn2)cc(C)c1-c1cccc(COc2ccc3c(c2)OC[C@H]3CC(=O)O)c1] | a yellow solid | 560.2 [M − 1] | 1H NMR (400 MHz, CDCl3) δ 8.78 (d, 1H), 8.19 (dd, 1H), 7.48-7.40 (m, 2H), 7.23 (s, 1H), 7.14 (d, 1H), 7.08 (dd, 2H), 6.90 (s, 2H), 6.52-6.47 (m, 2H), 5.09 (s, 2H), 4.77 (t, 1H), 4.30 (dd, 1H), 3.82 (m, 1H), 3.11 (s, 3H), 2.82 (dd, 1H), 2.62 (dd, 1H), 2.04 (s, 6H). |

Compounds of Examples 25-34 were prepared using the appropriate reactants according to the processes of Examples 1 and 18.

Example No., structure and characterization data are listed below:

| No. | Structure | Properties | MS | HNMR |
|-----|-----------|------------|-----|------|
| 25 | 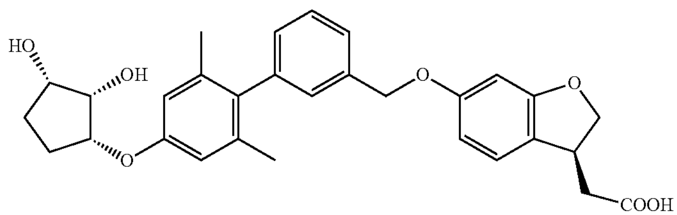 [SMILES: Cc1cc(O[C@@H]2CC[C@H](O)[C@@H]2O)cc(C)c1-c1cccc(COc2ccc3c(c2)OC[C@H]3CC(=O)O)c1] | a white solid | 503.3 [M − 1] | $^1$H NMR (400 MHz, CDCl$_3$) δ 7.44-7.36 (m, 2H), 7.17 (s, 1H), 7.10-7.04 (m, 2H), 6.68(s, 2H), 6.50-6.45 (m, 2H), 5.14 (s, 1H), 5.06 (s, 2H), 4.78-4.73 (m, 1H), 4.70-4.63 (m, 1H), 4.34-4.24 (m, 1H), 4.19-4.13 (m, 1H), 3.84-3.76 (m, 1H), 2.84-2.74 (m, 1H), 2.65-2.57 (m, 1H), 2.17-2.08 (m, 1H), 1.99 (s, 6H), 1.87-1.79 (m, 2H), 1.76-1.67 (m, 1H). |
| 26 | 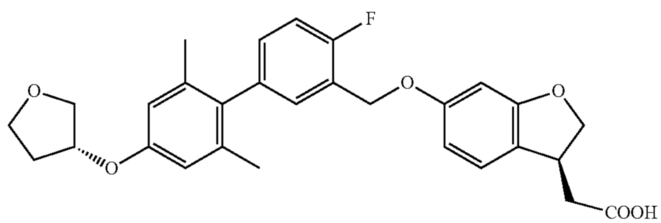 [SMILES: Cc1cc(O[C@@H]2CCOC2)cc(C)c1-c1ccc(F)c(COc2ccc3c(c2)OC[C@H]3CC(=O)O)c1] | a white solid | 510.3 [M + 18] | 1H NMR (400 MHz, CDCl3) δ 7.23 (dd, 1H), 7.14-7.04 (m, 3H), 6.60 (s, 2H), 6.50-6.45 (m, 2H), 5.13 (s, 2H), 4.94 (m, 1H), 4.76 (t, 1H), 4.28 (dd, 1H), 4.02-3.89 (m, 4H), 3.80 (m, 1H), 2.80 (dd, 1H), 2.61 (dd, 1H), 2.20 (m, 2H), 1.96 (s, 6H). |
| 27 | 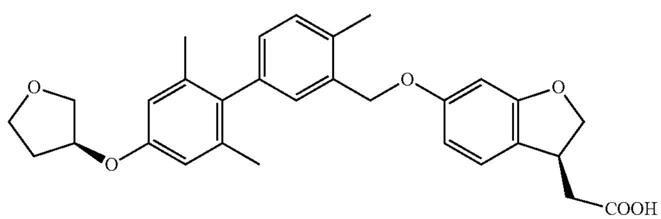 [SMILES: Cc1ccc(-c2c(C)cc(O[C@H]3CCOC3)cc2C)cc1COc1ccc2c(c1)OC[C@H]2CC(=O)O] | a white solid | 506.3 [M + 18] | 1H NMR (400 MHz, CDCl3) δ7.25 (d,1H), 7.15 (d, 1H), 7.06 (d, 1H), 7.01 (dd,1H), 6.61 (s, 2H), 6.52-6.47 (m, 2H), 5.04 (s, 2H), 4.94 (m, 1H), 4.77 (t, 1H), 4.29 (dd, 1H), 4.06-3.90 (m, 4H), 3.82 (m, 1H), 2.82 (dd, 1H), 2.62 (dd, 1H), 2.41 (s, 3H), 2.21 (m, 2H), 1.99 (s, 6H). |
| 28 | 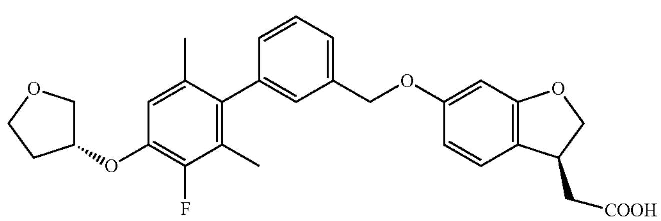 [SMILES: Cc1cc(O[C@@H]2CCOC2)c(F)c(C)c1-c1cccc(COc2ccc3c(c2)OC[C@H]3CC(=O)O)c1] | a white solid | 491.2 [M − 1] | $^1$H NMR (400 MHz, CDCl$_3$) δ 7.47-7.36 (m, 2H), 7.15 (s, 1H), 7.07 (d, 2H), 6.68 (d, 1H), 6.55-6.44 (m, 2H), 5.06 (s, 2H), 5.01-4.92 (m, 1H), 4.84-4.72 (m, 1H), 4.36-4.24 (m, 1H), 4.10-3.98 (m, 3H), 3.98-3.89 (m, 1H), 3.87-3.72 (m, 1H), 2.86-2.76 (m, 1H), 2.66-2.55 (m, 1H), 2.29-2.13 (m, 2H), 1.96 (s, 3H), 1.92 (d, 3H). |
| 29 | 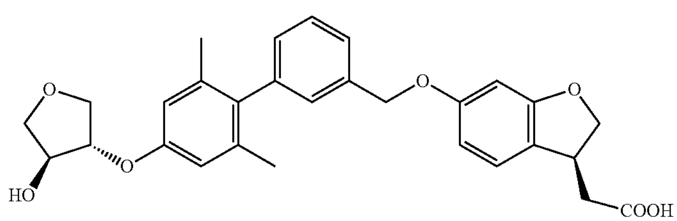 [SMILES: Cc1cc(O[C@H]2COC[C@@H]2O)cc(C)c1-c1cccc(COc2ccc3c(c2)OC[C@H]3CC(=O)O)c1] | a white solid | 508.3 [M + 18] | 1H NMR (400 MHz, CDCl3) δ 7.40 (m, 2H), 7.16 (s, 1H), 7.06 (m, 2H), 6.66 (s, 2H), 6.48 (m, 2H), 5.06 (s, 2H), 4.75 (m, 2H), 4.47 (d, 1H), 4.29 (m, 2H), 4.07 (dd, 1H), 3.95 (dd, 1H), 3.87 (d, 1H), 3.80 (m, 1H), 2.80 (dd, 1H), 2.61 (dd, 1H), 1.99 (s, 6H). |
| 30 | 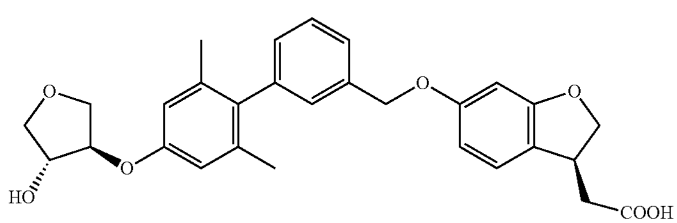 [SMILES: Cc1cc(O[C@@H]2COC[C@H]2O)cc(C)c1-c1cccc(COc2ccc3c(c2)OC[C@H]3CC(=O)O)c1] | a white solid | 508.3 [M + 18] | 1H NMR (400 MHz, CDCl3) δ 7.40 (m, 2H), 7.16 (s, 1H), 7.06 (m, 2H), 6.66 (s, 2H), 6.48 (m, 2H), 5.06 (s, 2H), 4.75 (m, 2H), 4.47 (d, 1H), 4.29 (m, 2H), 4.07 (dd, 1H), 3.95 (dd, 1H), 3.87 (d, 1H), 3.80 (m, 1H), 2.80 (dd, 1H), 2.61 (dd, 1H), 1.99 (s, 6H). |

| No. | Structure | Properties | MS | HNMR |
|---|---|---|---|---|
| 31 | 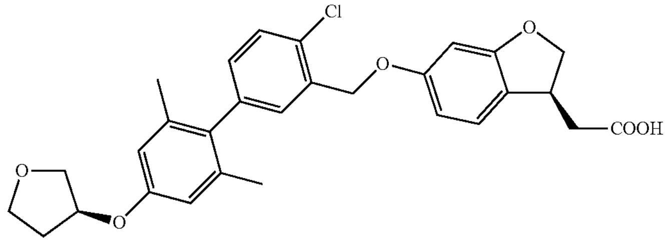 [SMILES: Cc1cc(O[C@H]2CCOC2)cc(C)c1-c1ccc(Cl)c(COc2ccc3c(c2)OC[C@H]3CC(=O)O)c1] | a white solid | 526.2 [M + 18] | $^1$H NMR (400 MHz, CDCl$_3$) δ 7.45-7.39 (m, 1H), 7.30 (s, 1H), 7.10-6.97 (m, 2H), 6.60 (s, 2H), 6.52-6.40 (m, 2H), 5.16 (s, 2H), 4.99-4.90 (m, 1H), 4.80-4.71 (m, 1H), 4.33-4.24 (m, 1H), 4.05-3.96 (m, 3H), 3.95-3.86 (m, 1H), 3.86-3.75 (m, 1H), 2.85-2.73 (m, 1H), 2.67-2.55 (m, 1H), 2.26-2.15 (m, 2H), 1.95 (s, 6H). |
| 32 | 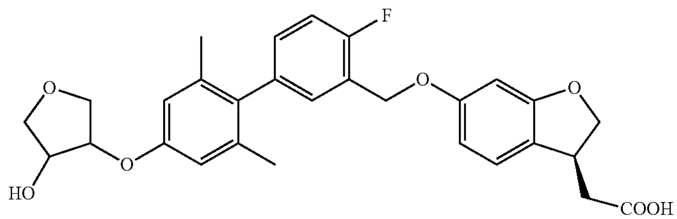 [SMILES: Cc1cc(OC2COCC2O)cc(C)c1-c1ccc(F)c(COc2ccc3c(c2)OC[C@H]3CC(=O)O)c1] | a white solid | 507.4 [M − 1] | $^1$H NMR (400 MHz, CDCl$_3$) δ 7.19-7.10 (m, 1H), 7.08-7.01 (m, 1H), 7.01-6.90 (m, 2H), 6.61 (s, 2H), 6.43-6.31 (m, 2H), 5.05(s, 2H), 4.74-4.57 (m, 2H), 4.40-4.29 (m, 1H), 4.24-4.11 (m, 2H), 4.01-3.92 (m, 1H), 3.92-3.81 (m, 2H), 3.80-3.65 (m, 2H), 2.74-2.59 (m, 1H), 2.54-2.38 (m, 1H), 1.89 (s, 6H) |
| 33 | 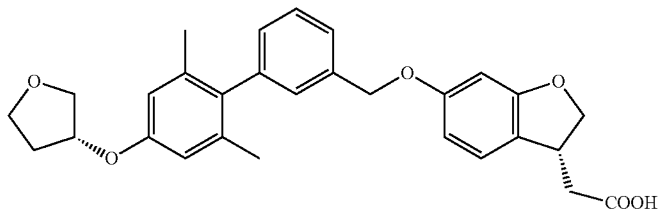 [SMILES: Cc1cc(O[C@@H]2CCOC2)cc(C)c1-c1cccc(COc2ccc3c(c2)OC[C@@H]3CC(=O)O)c1] | a white solid | 473.3 [M − 1] | $^1$H NMR (400 MHz, CDCl$_3$) δ 7.40-7.46 (m, 2H), 7.21 (s, 1H), 7.08-7.14 (m, 2H), 6.66 (s, 2H), 6.51-6.55 (m, 2H), 5.10 (s, 2H), 4.98-5.00 (m, 1H), 4.78-4.83 (m, 1H), 4.31-4.35 (m, 1H), 3.85-4.08 (m, 5H), 2.88-2.83 (m, 1H), 2.63-2.69 (m, 1H), 2.22-2.28 (m, 2H), 2.03 (s, 6H). |
| 34 | 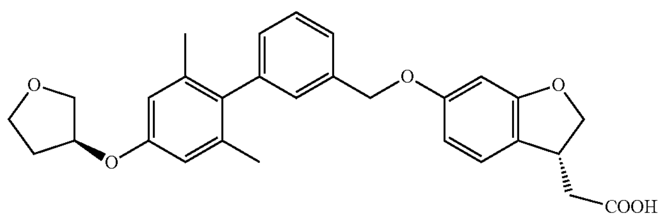 [SMILES: Cc1cc(O[C@H]2CCOC2)cc(C)c1-c1cccc(COc2ccc3c(c2)OC[C@@H]3CC(=O)O)c1] | a white solid | 473.3 [M − 1] | $^1$H NMR (400 MHz, CDCl$_3$) δ 7.39-7.45 (m, 2H), 7.18 (s, 1H), 7.05-7.10 (m, 2H), 6.62 (s, 2H) 6.47-6.52 (m, 2H), 5.07 (s, 2H), 4.95-4.96 (m, 1H), 4.75-4.79 (m, 1H), 4.28-4.31 (m, 1H), 3.82-4.06 (m, 5H), 2.79-2.84 (m, 1H), 2.59-2.66 (m, 1H), 2.19-2.24 (m, 2H), 2.00 (s, 6H). |

Example 35

2-((S)-6-(((2'-(Hydroxymethyl)-6'-methyl-4'-(((R)-tetrahydrofuran-3-yl)oxy)biphenyl-3-yl)methoxy)-2,3-dihydrobenzofuran-3-yl)acetic acid

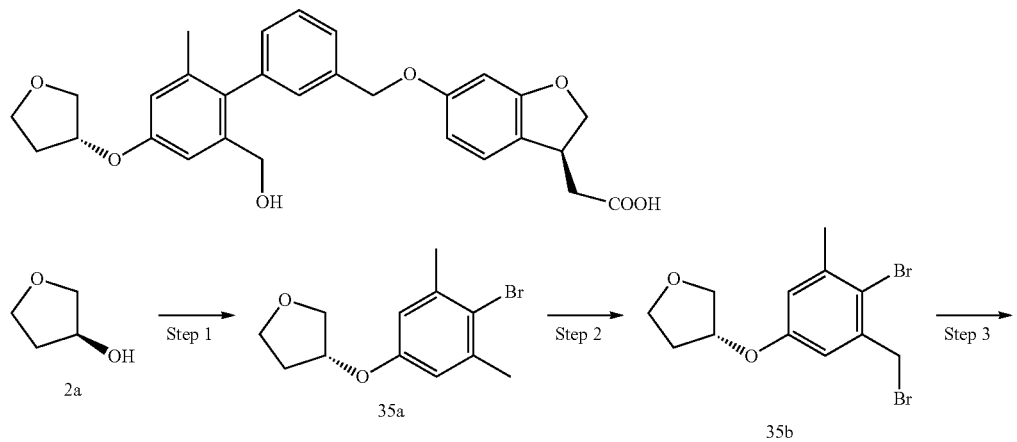

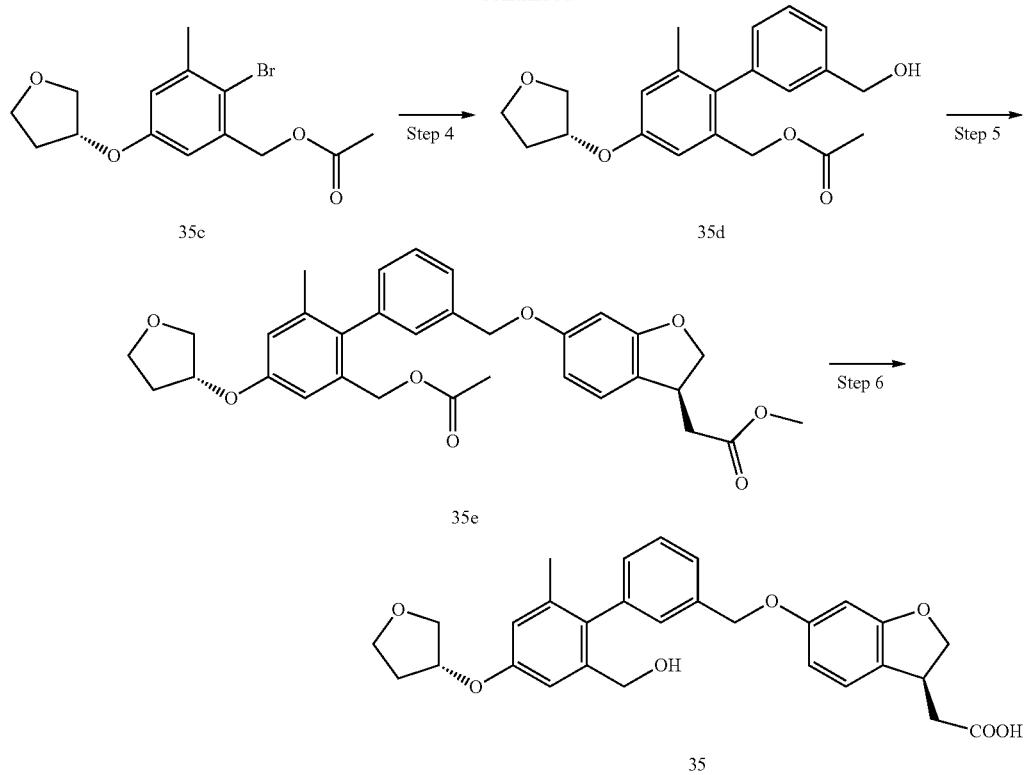

Step 1

(R)-3-(4-Bromo-3,5-dimethylphenoxy)tetrahydrofuran (S)-Tetrahydrofuran-3-ol 2a (1 g, 11.35 mmol) was dissolved in 30 mL of dichloromethane, followed by addition of 4-bromo-3,5-dimethylphenol (2.28 g, 11.35 mmol). The reaction solution was cooled down to 0° C., followed by addition of triphenylphosphine (3.57 g, 13.62 mmol) and diisopropyl azodicarboxylate (2.75 g, 13.62 mmol) successively. The reaction solution was warmed up to room temperature and stirred for 12 hours. The resulting solution was concentrated under reduced pressure and the residue was purified by silica gel column chromatography with elution system B to obtain the title compound (R)-3-(4-bromo-3,5-dimethylphenoxy)tetrahydrofuran 35a (2.27 g, yield 73.9%) as a colorless oil.

Step 2

(R)-3-(4-Bromo-3-(bromomethyl)-5-methylphenoxy)tetrahydrofuran (R)-3-(4-Bromo-3,5-dimethylphenoxy)tetrahydrofuran 35a (2.27 g, 8.37 mmol), N-bromosuccinimide (1.79 g, 10.04 mmol) and azobisisobutyronitrile (64 mg, 0.42 mmol) were dissolved in 50 mL of carbon tetrachloride. The reaction solution was heated to 60° C. and stirred for 12 hours. The resulting solution was concentrated under reduced pressure, mixed with 50 mL of tert-butyl methyl ether, stirred for 10 minutes, filtered and washed with tert-butyl methyl ether (20 mL×2). The combined filtrate was concentrated under reduced pressure and the residue was purified by silica gel column chromatography with elution system B to obtain the title compound (R)-3-(4-bromo-3-(bromomethyl)-5-methylphenoxy)tetrahydrofuran 35b (707 mg, yield 24.2%) as a light yellow solid.

Step 3

(R)-2-Bromo-3-methyl-5-((tetrahydrofuran-3-yl)oxy)benzyl acetate (R)-3-(4-Bromo-3-(bromomethyl)-5-methylphenoxy)tetrahydrofuran 35b (700 mg, 2 mmol) was dissolved in 15 mL of N,N-dimethylformamide, followed by addition of potassium acetate (197 mg, 2 mmol). The reaction solution was heated to 50° C. and stirred for 1 hour. The resulting solution was cooled down to room temperature, mixed with 100 mL of water and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the crude title compound (R)-2-bromo-3-methyl-5-((tetrahydrofuran-3-yl)oxy)benzyl acetate 35c (658 mg) as a yellow oil, which was used directly in the next step without further purification.

MS m/z (ESI): 346.3 [M+18]

Step 4

(R)-(3'-(Hydroxymethyl)-6-methyl-4-((tetrahydrofuran-3-yl)oxy)biphenyl-2-yl)methyl acetate The crude (R)-2-bromo-3-methyl-5-((tetrahydrofuran-3-yl)oxy)benzyl acetate 35c (658 mg, 2 mmol) was dissolved in 50 mL of dioxane, followed by addition of 3-hydroxymethyl phenylboronic acid (608 mg, 4 mmol) and 6 mL of aqueous potassium carbonate solution (636 mg, 4 mmol), and then [1,1'-bis(diphenylphosphino)ferrocene]dichloropalladium (II) (74 mg, 0.10 mmol). The reaction solution was heated to 70° C. and stirred for 4 hours. The resulting solution was cooled, poured into 100 mL 1M aqueous hydrochloric acid solution, and extracted with ethyl acetate (30 mL×3). The combined organic extracts were washed with saturated sodium chloride solution (30 mL), dried with anhydrous magnesium sulphate, and filtered. The filtrate was concentrated under reduced pressure. The residue was purified by silica gel column chromatography with elution system B to obtain the title compound (R)-(3'-(hydroxymethyl)-6-methyl-4-((tetrahydrofuran-3-yl)oxy)biphenyl-2-yl)methyl acetate 35d (476 mg, yield 66.8%) as a yellow oil.

MS m/z (ESI): 374.4 [M+18]

Step 5

Methyl 2-((S)-6-((2'-(acetoxymethyl)-6'-methyl-4'-(((R)-tetrahydrofuran-3-yl)oxy) biphenyl-3-yl)methoxy)-2,3-dihydrobenzofuran-3-yl)acetate (R)-(3'-(Hydroxymethyl)-6-methyl-4-((tetrahydrofuran-3-yl)oxy)biphenyl-2-yl)methyl acetate 35d (127 mg, 0.36 mmol) was dissolved in 10 mL of dichloromethane, followed by addition of methyl (S)-2-(6-hydroxyl-2,3-dihydrobenzofuran-3-yl)acetate (89 mg, 0.43 mmol) and triphenylphosphine (112 mg, 0.43 mmol). The reaction solution was cooled down to 0° C., followed by addition of diisopropyl azodicarboxylate (87 mg, 0.43 mmol). The reaction solution was warmed up to room temperature and stirred for 12 hours. The resulting solution was concentrated under reduced pressure to obtain the crude title compound methyl 2-((S)-6-((2'-(acetoxymethyl)-6'-methyl-4'-(((R)— tetrahydrofuran-3-yl)oxy)biphenyl-3-yl)methoxy)-2,3-dihydrobenzofuran-3-yl) acetate 35e (189 mg) as a yellow oil, which was used directly in the next step without further purification.

Step 6

2-((S)-6-((2'-(Hydroxymethyl)-6'-methyl-4'-(((R)-tetrahydrofuran-3-yl)oxy)biphenyl-3-yl)methoxy)-2,3-dihydrobenzofuran-3-yl)acetic acid The crude methyl 2-((S)-6-((2'-(acetoxymethyl)-6'-methyl-4'-(((R)-tetrahydrofuran-3-yl)oxy)biphenyl-3-yl)methoxy)-2,3-dihydrobenzofuran-3-yl)acetate 35e (189 mg, 0.36 mmol) was dissolved in 10 mL of a mixture of the solvents of methanol and tetrahydrofuran (V/V=1:4), followed by addition of 1M aqueous lithium hydroxide solution (4 mL, 4 mmol). The reaction solution was stirred for 3 hours. The resulting solution was added with 50 mL of water and 5 mL of 2M aqueous sodium hydroxide solution. The aqueous phase was washed with ethyl acetate (30 mL), then 1M hydrochloric acid was added dropwise to adjust the pH to 2-3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure and the residue was purified by TLC with elution system A to obtain the title compound 2-((S)-6-((2'-(hydroxymethyl)-6'-methyl-4'-(((R)-tetrahydrofuran-3-yl)oxy)biphenyl-3-yl)methoxy)-2,3-dihydrobenzofuran-3-yl)acetic acid 35 (15 mg, yield 8.6%) as a white solid.

MS m/z (ESI): 489.2 [M−1]

$^1$H NMR (400 MHz, DMSO-$d_6$) δ 7.35-7.48 (m, 2H), 7.03-7.19 (m, 3H), 6.93 (br, 1H), 6.73 (br, 1H), 6.42-6.52 (m, 2H), 5.08 (s, 2H), 5.03 (br, 1H), 4.68 (t, 1H), 4.14-4.24 (m, 1H), 4.07 (s, 2H), 3.91 (dd, 1H), 3.73-3.88 (m, 3H), 3.61-3.73 (m, 1H), 2.64-2.77 (m, 1H), 2.46 (d, 1H), 2.16-2.30 (m, 1H), 1.95-2.06 (m, 1H), 1.91 (s, 3H).

Example 36

2-((S)-6-((4-Hydroxy-2',6'-dimethyl-4'(((R)-tetrahydrofuran-3-yl)oxy)biphenyl-3-yl)methoxy)-2,3-dihydrobenzofuran-3-yl)acetic acid

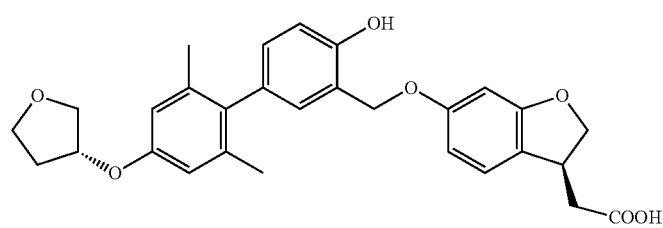

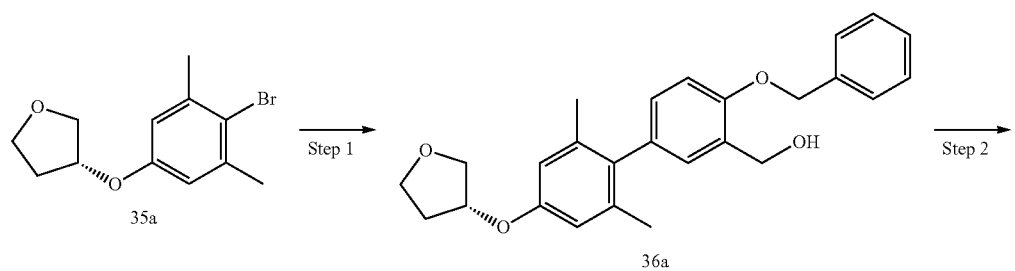

-continued

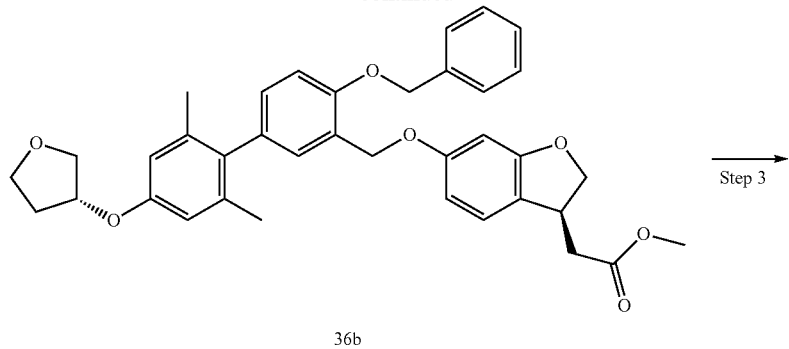

36b

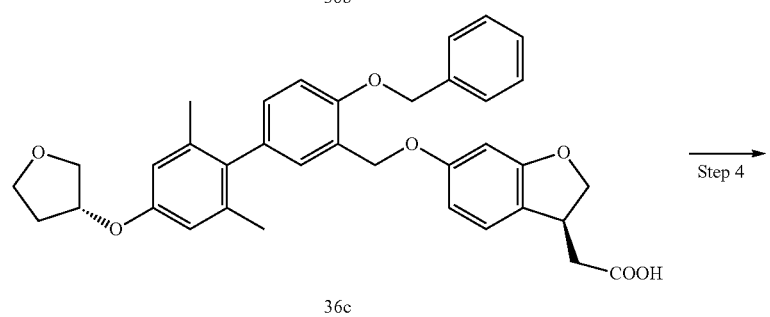

36c

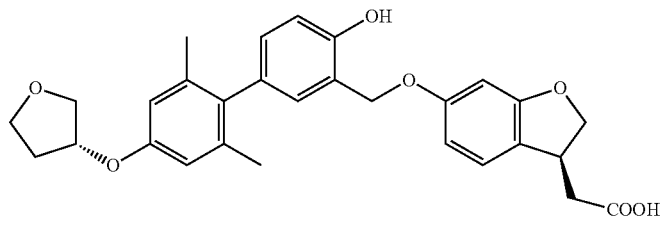

36

Step 1

(R)-(4-(Benzyloxy)-2',6'-dimethyl-4'-((tetrahydrofuran-3-yl)oxy)biphenyl-3-yl)methanol (R)-3-(4-Bromo-3,5-dimethylphenoxy)tetrahydrofuran 35a (731 mg, 2.69 mmol) was dissolved in 20 mL of dioxane, followed by addition of (2-(benzyloxy)-5-(4,4,5,5-tetramethyl-dioxaborolane-2-yl)phenyl)methanol (1.28 g, 3.76 mmol, prepared by a method disclosed in patent application US2011275797) and 4 mL of aqueous sodium bicarbonate solution (855 mg, 8.07 mmol) and [1,1'-bis(diphenylphosphino)ferrocene]dichloropalladium(II) (98 mg, 0.14 mmol). The reaction solution was heated to 70° C. and stirred for 4 hours. The resulting solution was cooled and poured into 100 mL of water, 1M hydrochloric acid was added dropwise to adjust the pH to 2-3, and extracted with ethyl acetate (30 mL×3). The combined organic extracts were washed with saturated sodium chloride solution (30 mL), dried with anhydrous magnesium sulphate, and filtered. The filtrate was concentrated under reduced pressure. The residue was purified by silica gel column chromatography with elution system B to obtain the title compound (R)-(4-(benzyloxy)-2',6'-dimethyl-4'-((tetrahydrofuran-3-yl)oxy)biphenyl-3-yl)methanol 36a (637 mg, yield 63.7%) as a yellow oil.

Step 2

Methyl 2-((S)-6-((4-(benzyloxy)-2',6'-dimethyl-4'-(((R)-tetrahydrofuran-3-yl)oxy)biphenyl-3-yl)methoxy)-2,3-dihydrobenzofuran-3-yl)acetate (R)-(4-(Benzyloxy)-2',6'-dimethyl-4'-((tetrahydrofuran-3-yl)oxy)biphenyl-3-yl)methanol 36a (637 mg, 1.69 mmol) was dissolved in 20 mL of dichloromethane, followed by addition of methyl (S)-2-(6-hydroxyl-2,3-dihydrobenzofuran-3-yl)acetate (423 mg, 2.03 mmol) and triphenylphosphine (532 mg, 2.03 mmol). The reaction solution was cooled down to 0° C., followed by addition of diisopropyl azodicarboxylate (411 mg, 2.03 mmol), then warmed up to room temperature and stirred for 12 hours. The resulting solution was concentrated under reduced pressure to obtain the crude title compound methyl 2-((S)-6-((4-(benzyloxy)-2',6'-dimethyl-4'-(((R)-tetrahydrofuran-3-yl)oxy)biphenyl-3-yl)methoxy)-2,3-dihydrobenzofuran-3-yl)acetate 36b (1 g) as a brown oil, which was used directly in the next step without further purification.

Step 3

2-((S)-6-((4-(Benzyloxy)-2',6'-dimethyl-4'-(((R)-tetrahydrofuran-3-yl)oxy)biphenyl-3-yl)methoxy)-2,3-dihydrobenzofuran-3-yl)acetic acid The crude methyl 2-((S)-6-((4-(benzyloxy)-2',6'-dimethyl-4'-(((R)-tetrahydrofuran-3-yl)oxy)biphenyl-3-yl)

methoxy)-2,3-dihydrobenzofuran-3-yl)acetate 36b (1 g, 1.69 mmol) was dissolved in 50 mL of a mixed solvent of methanol and tetrahydrofuran (V/V=1:4), followed by addition of 1M aqueous lithium hydroxide solution (20 mL, 20 mmol). The reaction solution was stirred for 2 hours. The resulting solution was concentrated under reduced pressure. The residue was mixed with 150 mL of water and 30 mL of ethyl acetate, 1M hydrochloric acid was added dropwise to adjust the pH to 2~3, and extracted with ethyl acetate (20 mL×2). The combined organic extracts were washed with saturated sodium chloride solution (30 mL), dried with anhydrous magnesium sulphate, and filtered. The filtrate was concentrated under reduced pressure to obtain the crude title compound 2-((S)-6-((4-(benzyloxy)-2',6'-dimethyl-4'-(((R)-tetrahydrofuran-3-yl)oxy)biphenyl-3-yl)methoxy)-2,3-dihydrobenzofuran-3-yl)acetic acid 36c (152 mg) as a brown oil, which was directly used in the next step without further purification.

MS m/z (ESI): 579.4 [M−1]

Step 4

2-((S)-6-((4-Hydroxy-2',6'-dimethyl-4'-(((R)-tetrahydrofuran-3-yl)oxy)biphenyl-3-yl)methoxy)-2,3-dihydrobenzofuran-3-yl)acetic acid 2-((S)-6-((4-(Benzyloxy)-2',6'-dimethyl-4'-(((R)-tetrahydrofuran-3-yl)oxy)biphenyl-3-yl)methoxy)-2,3-dihydrobenzofuran-3-yl)acetic acid 36c (152 mg, 0.26 mmol) was dissolved in 5 mL of ethyl acetate, followed by addition of Pd/C (30 mg, 10%). The reaction solution was stirred for 12 hours. The resulting solution was filtered. The filtrate was concentrated under reduced pressure and the residue was purified by TLC with elution system A to obtain the crude title compound 2-((S)-6-((4-hydroxy-2',6'-dimethyl-4'-(((R)-tetrahydrofuran-3-yl)oxy)biphenyl-3-yl)methoxy)-2,3-dihydrobenzofuran-3-yl)acetic acid 36 (18 mg, yield 14.1%) as a white solid.

MS m/z (ESI): 491.4 [M+1]

$^1$H NMR (400 MHz, DMSO-$d_6$) δ 12.34 (br, 1H), 9.68 (s, 1H), 7.08 (d, 1H), 6.96 (s, 1H), 6.82-6.93 (m, 2H), 6.63 (s, 2H), 6.37-6.49 (m, 2H), 5.00 (s, 3H), 4.67 (t, 1H), 4.12-4.22 (m, 1H), 3.89 (dd, 1H), 3.71-3.85 (m, 3H), 3.66 (t, 1H), 2.68 (dd, 1H), 2.45 (d, 1H), 2.19 (dd, 1H), 1.96 (dd, 1H), 1.89 (s, 6H).

TEST EXAMPLES

Biological Assay

Test Example 1

Agonist activity of compounds of the present disclosure on CHO-K1/GPR40 cell.

The following method was used to determine the agonist activity of compounds of the present disclosure on GPR40. The experiment process is described as follows:

CHO-K1/GPR40 cell (CHO-K1 cell line expressing GPR40, which was constructed using retrovirus infection method, CHO-K1/GPR40 cell for short, wherein CHO-$K_1$ cell was purchased from Cell bank of the Chinese Academy of Sciences, catalogue number GNHa 7; GPR40 cDNA was purchased from Guangzhou FulenGen Co., Ltd, catalogue number EX-UO270-MO2) was inoculated in a 96-well plate with an inoculation density of 25000 cells/well. The cell plate was incubated at 37° C. and 5% $CO_2$ for 24 hours. The cell culture fluid was discarded during the experiment, the cells were washed with buffer solution (1×HBSS+20 mM HEPES pH 7.4) once, 100 μL of Fluo-4 calcium ion dye was quickly added into each well, incubated at 37° C. in the dark for 30 minutes, and then at room temperature for another 30 minutes. During the determination, the baseline value of each well was read at first, and then different concentrations of drug were added to the wells (50 μL/well), and the fluorescence values were then read. The fluorescence excitation wavelength was 494 nm and the emission wavelength was 516 nm. The increase of fluorescence intensity was proportional to calcium ion level in the cells. Cell response rate of each cell/(The maximum fluorescence value−The minimum fluorescence value)/The minimum fluorescence value. $EC_{50}$ values of the compounds were calculated

| Example No. | $EC_{50}$(CHO-K1/GPR40)/(nM) |
| --- | --- |
| Example 1 | 31 |
| Example 2 | 35 |
| Example 4 | 81 |
| Example 5 | 107 |
| Example 6 | 161 |
| Example 7 | 161 |
| Example 8 | 88 |
| Example 9 | 161 |
| Example 10 | 134 |
| Example 11 | 73 |
| Example 12 | 113 |
| Example 13 | 16 |
| Example 16 | 15 |
| Example 17 | 157 |
| Example 18 | 28 |
| Example 19 | 55 |
| Example 20 | 140 |
| Example 21 | 131 |
| Example 22 | 77 |
| Example 23 | 141 |
| Example 25 | 31 |
| Example 26 | 52 |
| Example 27 | 53 |
| Example 28 | 82 |
| Example 29 | 41 |
| Example 30 | 34 |
| Example 33 | 113 |
| Example 34 | 113 |

Conclustion: the compounds of the present disclosure had significant agonist activity on GPR40.

Pharmacokinetics Assay

1. Purpose

The compounds of the present invention were administered intragastrically to determine the drug concentration in plasma at different time points. The pharmacokinetic behavior of the compounds of the present invention was studied and evaluated in rats.

2. Protocol 2.1 Samples

Compounds of Example 1, Example 2, Example 13 and Example 30

2.2 Test Animals 16 healthy adult SD rats were divided into 4 groups with 4 in each group, half male and half female. Rats were purchased from SINO-BRITSH SIPPR/BK LAB. ANIMAL LTD., CO, License number: SCXK (Shanghai) 2008-0016

2.3 Preparation of Test Compounds

The appropriate amount of test compounds were weighed and added to 0.5% sodium carboxymethyl cellulose to prepare a 0.5 mg/mL suspension using microwave.

2.4 Administration and Samples Collection

After an overnight fast, the rats were administered intragastrically a dose of 5.0 mg/kg, at an administration volume of 10 mL/kg. Blood samples were taken before administration and after administration at different time points over 24.0 hours, using heparin as an anticoagulant. The separated plasma samples were stored at −20° C. The rats were fed 2 hours after administration.

3. Analytical Methods

Blood samples (0.1 mL) were taken before administration and at 1.0, 2.0, 3.0, 4.0, 6.0, 8.0, 11.0, 24.0 and 48.0 hours after administration, which were stored in heparinized tubes and centrifuged for 5 minutes at 3,500 rpm to separate blood plasma. The plasma samples were stored at −20° C. The rats were fed 2 hours after administration.

The content of the different test compounds in rat plasma samples after the intragastric administration was determined by LC/MS/MS method. The linearity of the method is 1.00~2000 ng/ml. The blood sample was analyzed after protein precipitation was accomplished by the addition of methanol.

4. Results of Pharmacokinetic Parameters

Pharmacokinetic Parameters of the compounds of the present disclosure were shown as follows:

| Example No. | Plasma Conc. Cmax (ng/mL) | Area under Curve AUC (ng/mL * h) | Half-Life $t_{1/2}$ (h) | Mean Residence Time MRT (h) | Clearance CL/F (l/h/kg) | Apparent Distribution Volume Vz/F (l/kg) |
|---|---|---|---|---|---|---|
| Example 1 | 1693 ± 698 | 21609 ± 8619 | 10.1 ± 3.3 | 14.5 ± 4.7 | 0.24 ± 0.08 | 3.39 ± 1.24 |
| Example 2 | 2013 ± 511 | 32905 ± 11939 | 13.4 ± 3.8 | 18.9 ± 6.0 | 0.15 ± 0.05 | 2.79 ± 0.79 |
| Example 13 | 3153 ± 482 | 39357 ± 10659 | 10.0 ± 0.3 | 12.5 ± 1.5 | 0.13 ± 0.03 | 1.85 ± 0.37 |
| Example 30 | 2728 ± 478 | 38214 ± 15033 | 9.35 ± 0.55 | 13.3 ± 2.0 | 0.14 ± 0.05 | 1.88 ± 0.66 |

Pharmacokinetics Assay (5 mg/Kg)

Conclusion: the compounds of the present disclosure had a high level of plasma concentration and exposure, long half-life, and good pharmacokinetic profiles after intragastric administration to rats.

Pharmacodynamics Assay

1. Purpose

ICR mice fed on a high fat diet were used as test animals. The effect of oral administration of a single dose of the compounds of the present disclosure on oral glucose tolerance test (OGTT) of glucose load mice was studied.

2. Test Compounds

Compounds of Example 1, Example 2, Example 13, Example 16, Example 18, Example 19 and Example 26

3. Test Animals

Healthy ICR male mice were purchased from SINO-BRITSH SIPPR/BK LAB. ANIMAL LTD., CO, License number: SCXK (Shanghai) 2008-0016

4. Preparation of Test Compounds

The test compounds were added to aqueous 0.5% CMC-Na solution to prepare the corresponding concentration suspension using microwave.

5. Test Method 5.1 Grouping

After an overnight fast for 16 hours, male mice fed on a high fat diet were weighed, and the basic blood glucose was determined. The mice were randomly divided into a Blank group and the group of each test compound of the present disclosure according to the level of blood glucose.

5.2 Dosage Setting

The dosage of administration was 20 mg/kg or 40 mg/kg, and the Blank group was administrated aqueous 0.5 CMC-Na solution.

5.3 Administration

20% Glucose solution was administered 15 minutes after intragastrical administration (each mouse was administered 0.4 mL)

5.4 Determination of Blood Glucose Value

The compounds were administered according to the aforesaid dosage to determine the blood glucose value (−15 minutes).

At 15 minutes after administration, 20% glucose solution was administrated at a dose of 2 g/kg and the blood glucose values at 0, 15, 30, 45, 60 and 120 minutes in each mouse were determined by Roche Accu-Chek blood glucose monitoring meter.

5.5 Data Statistics

Using Excel statistical software: the average value was calculated with avg; SD value was calculated with STDEV; and P value of difference among groups was calculated with TTEST.

AUC calculation formula:

$$AUC = (t_{15min} + t_{0min}) \times 0.25/2 + (t_{30min} + t_{15min}) \times 0.25/2 + (t_{45min} + t_{30min}) \times 0.25/2 + (t_{60min} + t_{45min}) \times 0.25/2 + (t_{120min} + t_{60min}) \times 1/2$$

Wherein $t_{0min}$, $t_{15min}$, $t_{30min}$, $t_{45min}$, $t_{60min}$, $t_{120min}$ were blood glucose values determined at different time points.

6. Experimental Result $$AUC \text{ decrease rate } \% = \frac{BlankAUC - DrugAUC}{Blank\ AUC}$$

| Example No. | Dosage | AUC decrease rate % |
|---|---|---|
| 1 | 40 mg/kg | 36.08 |
| 2 | 40 mg/kg | 29.49 |
| 13 | 40 mg/kg | 39.71 |
| 16 | 40 mg/kg | 15.72 |
| 18 | 40 mg/kg | 44.13 |
| 19 | 40 mg/kg | 36.78 |
| 26 | 40 mg/kg | 26.06 |
| 29 | 20 mg/kg | 20.41 |
| 30 | 40 mg/kg | 29.59 |

Conclusion: at the oral dosage of 20 mg/kg or 40 mg/kg, the compounds of the present disclosure significantly reduced the increase of blood glucose induced by glucose administration in mice fed on high fat diet.

What is claimed is:

1. A compound of formula (I), or a tautomer, mesomer, racemate, enantiomer, diastereomer, or mixture thereof, or a pharmaceutically acceptable salt thereof:

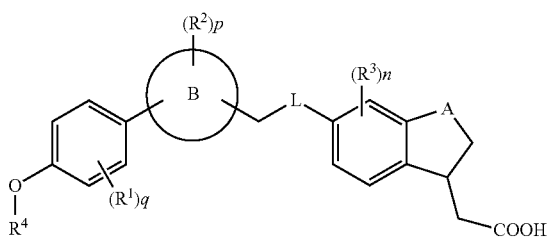

(I)

wherein:
A is selected from the group consisting of —O—, —CH$_2$—, and —CH$_2$CH$_2$—;
L is selected from the group consisting of —O— and —NH—;
ring B is selected from the group consisting of aryl and heteroaryl;
R$^1$, R$^2$, and R$^3$ are each independently selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR$^6$R$^7$, and —S(O)$_m$R$^5$, wherein the alkyl, alkoxy, cycloalkyl, heterocyclyl, aryl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR$^6$R$^7$, and —S(O)$_m$R$^5$;
R$^4$ is selected from the group consisting of the following cycloalkyl, heterocyclyl, and heteroaryl:

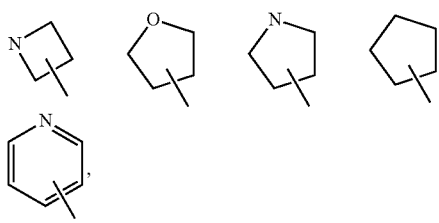

wherein the cycloalkyl, heterocyclyl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR$^5$, —OC(O)R$^5$, —C(O)R$^5$, —NHC(O)R$^5$, —NR$^6$R$^7$, and —S(O)$_m$R$^5$;
R$^5$ is selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, cyano, alkoxy, cycloalkyl, heterocyclyl, aryl, heteroaryl, carboxyl, and alkoxycarbonyl;
R$^6$ and R$^7$ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, alkoxy, cycloalkyl, heterocyclyl, aryl, heteroaryl, carboxyl, and alkoxycarbonyl;

m is 0, 1, or 2;
n is 0, 1, 2, or 3;
p is 0, 1, 2, 3, or 4; and
q is 0, 1, 2, 3, or 4.

2. The compound of formula (I), or a tautomer, mesomer, racemate, enantiomer, diastereomer, or mixture thereof, or a pharmaceutically acceptable salt thereof according to claim 1, wherein ring B is aryl.

3. The compound of formula (I), or a tautomer, mesomer, racemate, enantiomer, diastereomer, or mixture thereof, or a pharmaceutically acceptable salt thereof according to claim 1, selected from a compound of formula (II) or a tautomer, mesomer, racemate, enantiomer, diastereomer, or mixture thereof, or a pharmaceutically acceptable salt thereof:

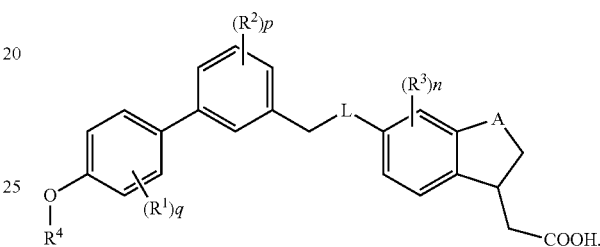

(II)

4. The compound of formula (I), or a tautomer, mesomer, racemate, enantiomer, diastereomer, or mixture thereof, or a pharmaceutically acceptable salt thereof according to claim 1, wherein L is —O—.

5. The compound of formula (I), or a tautomer, mesomer, racemate, enantiomer, diastereomer, or mixture thereof, or a pharmaceutically acceptable salt thereof according to claim 1, wherein R$^1$ is selected from the group consisting of alkyl, halogen, and hydroxyalkyl.

6. The compound of formula (I), or a tautomer, mesomer, racemate, enantiomer, diastereomer, or mixture thereof, or a pharmaceutically acceptable salt thereof according to claim 1, wherein R$^2$ is selected from the group consisting of alkyl and halogen, or p is 0.

7. The compound of formula (I), or a tautomer, mesomer, racemate, enantiomer, diastereomer, or mixture thereof, or a pharmaceutically acceptable salt thereof according to claim 1, wherein n is 0.

8. The compound of formula (I), or a tautomer, mesomer, racemate, enantiomer, diastereomer, or mixture thereof, or a pharmaceutically acceptable salt thereof according to claim 3, selected from a compound of formula (III) or a tautomer, mesomer, racemate, enantiomer, diastereomer, or mixture thereof, or a pharmaceutically acceptable salt thereof:

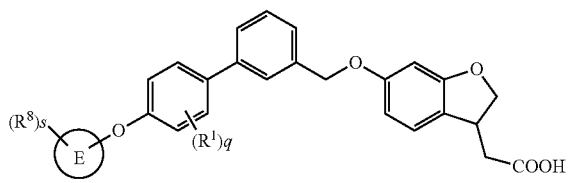

(III)

wherein:
ring E is selected from the group consisting of the following cycloalkyl, heterocyclyl, and heteroaryl:

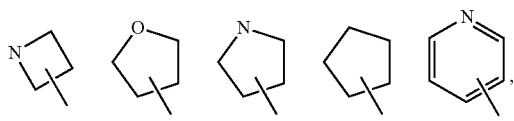

R¹ is selected from the group consisting of halogen, hydroxyl, cyano, nitro, alkyl, alkoxy, cycloalkyl, heterocyclyl, aryl, heteroaryl, —C(O)OR⁵, —OC(O)R⁵, —C(O)R⁵, —NHC(O)R⁵, —NR⁶R⁷, and —S(O)$_m$R⁵, wherein the alkyl, cycloalkyl, alkoxy, heterocyclyl, aryl, or heteroaryl is each optionally substituted with one or more groups selected from the group consisting of halogen, hydroxyl, cyano, nitro, alkyl, alkoxy, cycloalkyl, heterocyclyl, aryl, heteroaryl, —C(O)OR⁵, —OC(O)R⁵, —C(O)R⁵, —NHC(O)R⁵, —NR⁶R⁷, and —S(O)$_m$R⁵;

R⁵ is selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, cyano, alkoxy, cycloalkyl, heterocyclyl, aryl, heteroaryl, carboxyl, and alkoxycarbonyl;

R⁶ and R⁷ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is each optionally substituted with one or more groups selected from the group consisting of alkyl, halogen, hydroxyl, alkoxy, cycloalkyl, heterocyclyl, aryl, heteroaryl, carboxyl, and alkoxycarbonyl;

R⁸ is selected from the group consisting of halogen, hydroxyl, cyano, nitro, alkyl, alkoxy, cycloalkyl, heterocyclyl, heteroaryl, —C(O)OR⁵, —OC(O)R⁵, —C(O)R⁵, —NHC(O)R⁵, —NR⁶R⁷, and —S(O)$_m$R⁵;

m is 0, 1, or 2;

q is 0, 1, 2, 3, or 4; and s is 0, 1, 2, or 3.

9. The compound of formula (I), or a tautomer, mesomer, racemate, enantiomer, diastereomer, or mixture thereof, or a pharmaceutically acceptable salt thereof according to claim 8, selected from a compound of formula (IV) or a tautomer, mesomer, racemate, enantiomer, diastereomer, or mixture thereof, or a pharmaceutically acceptable salt thereof:

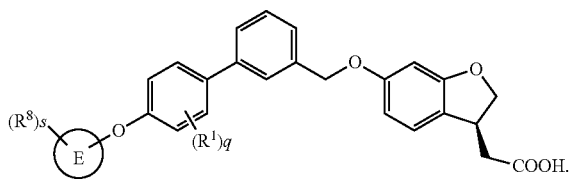

(IV)

10. The compound of formula (I), or a tautomer, mesomer, racemate, enantiomer, diastereomer, or mixture thereof, or a pharmaceutically acceptable salt thereof according to claim 1, wherein the compound is selected from the group consisting of:

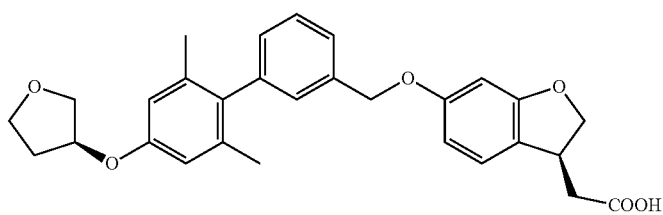

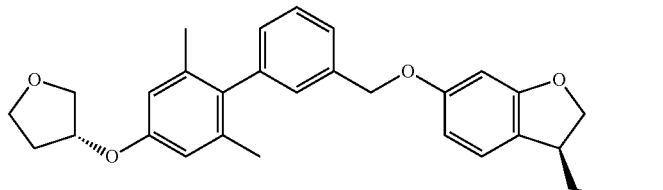

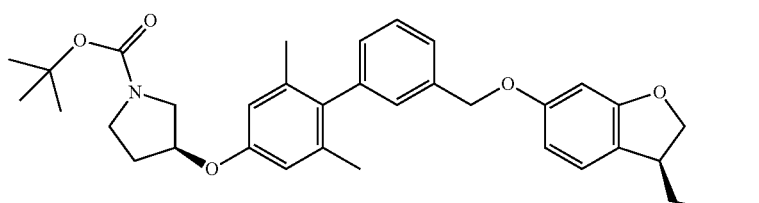

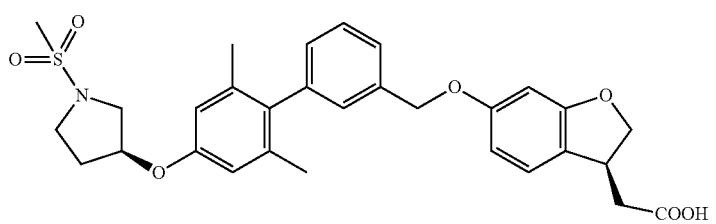

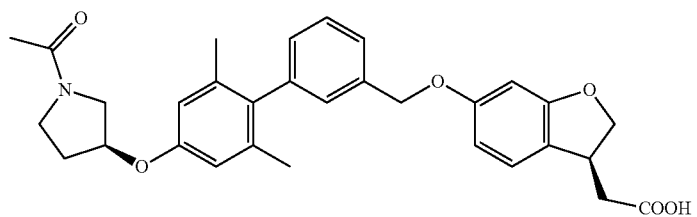
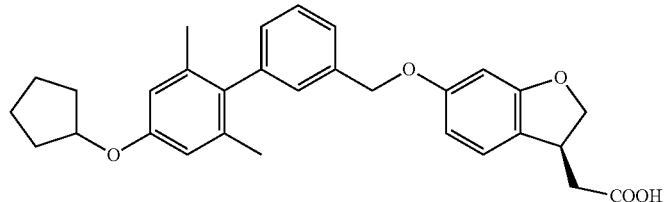
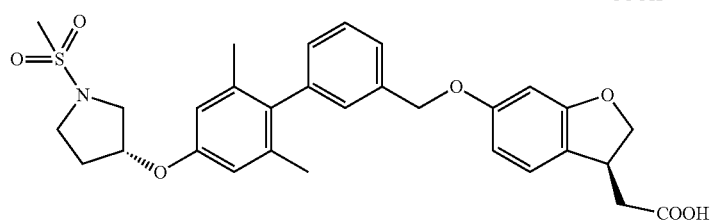
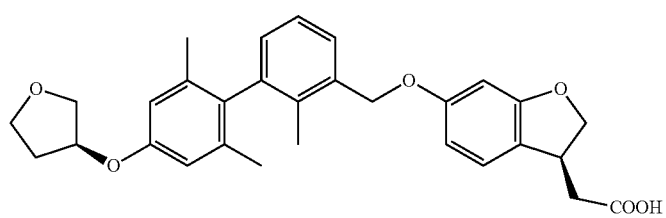
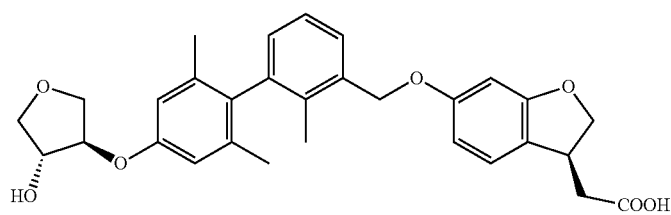
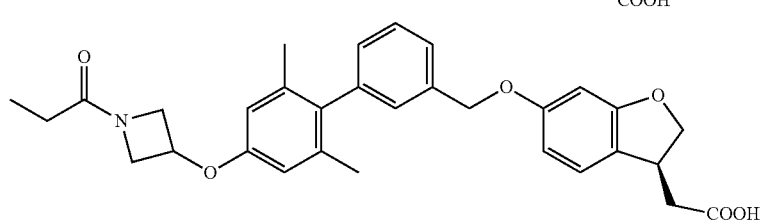
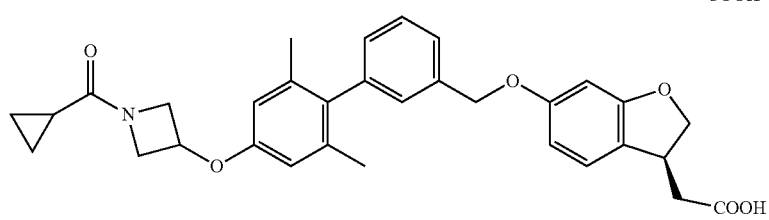
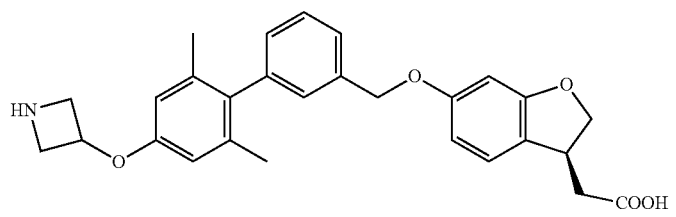

-continued
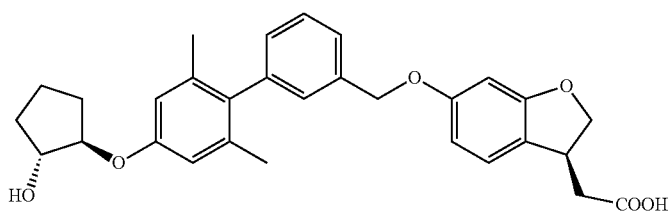
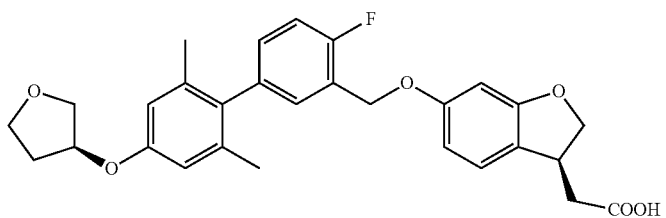
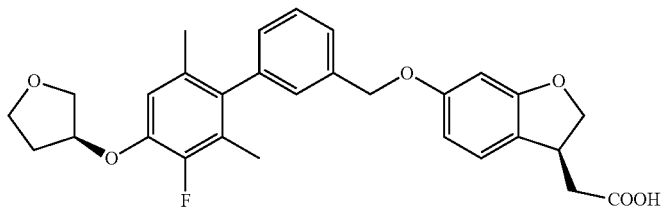
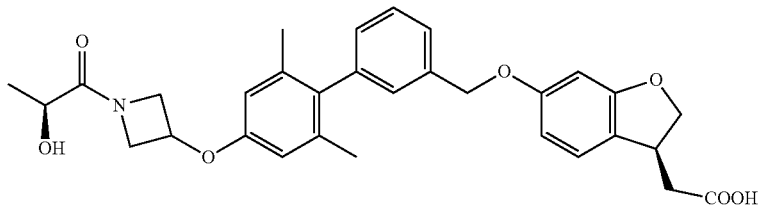
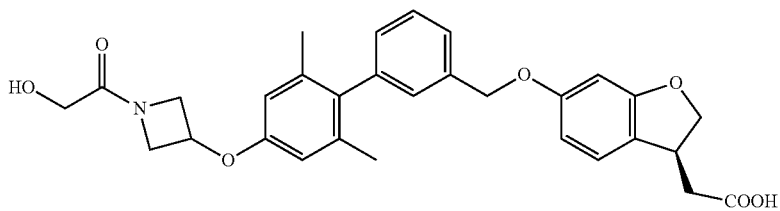
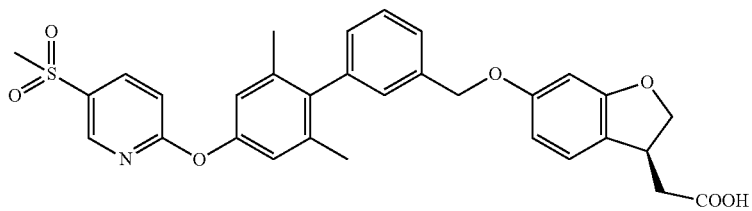
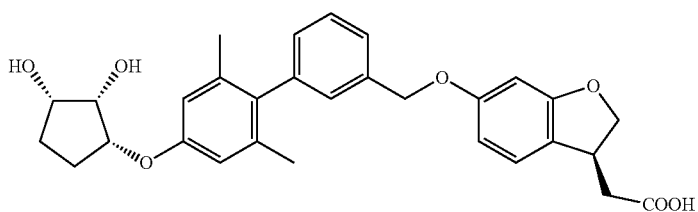
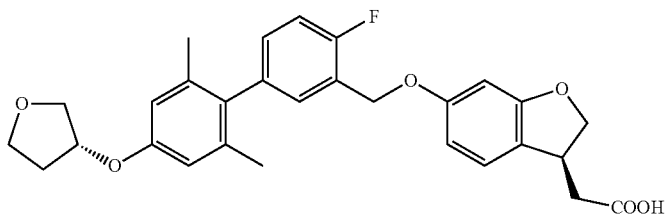

-continued
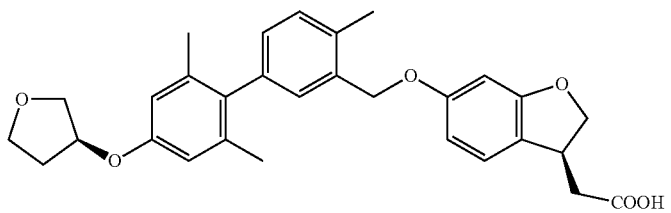
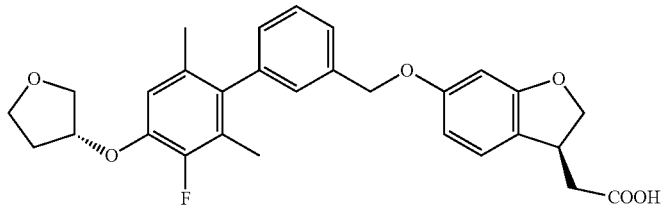
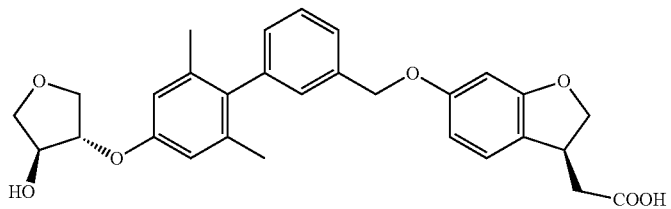
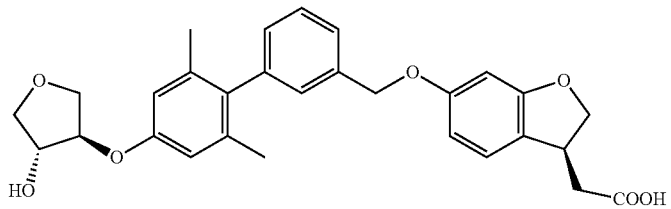
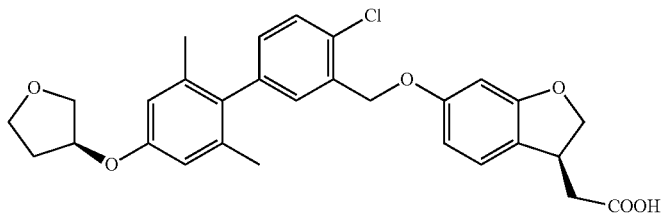
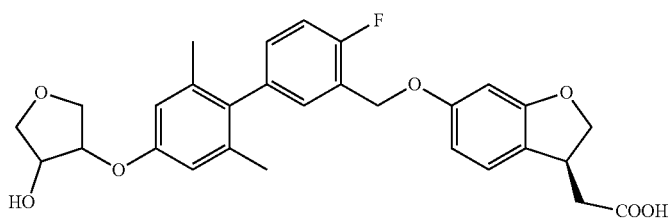
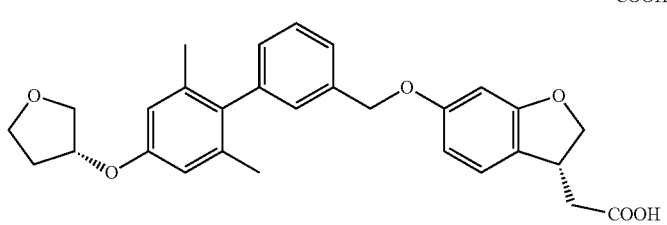
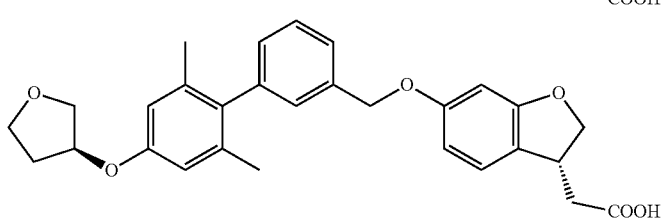

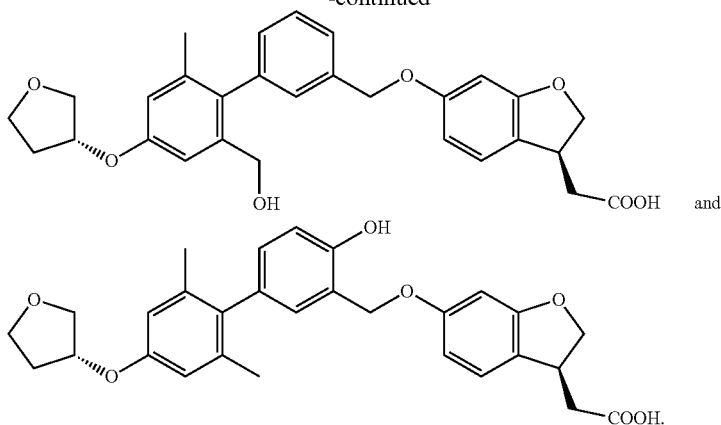

and

11. A preparation process of the compound of formula (I), or a tautomer, mesomer, racemate, enantiomer, diastereomer, or mixture thereof, or a pharmaceutically acceptable salt thereof according to claim 1, comprising a step of:

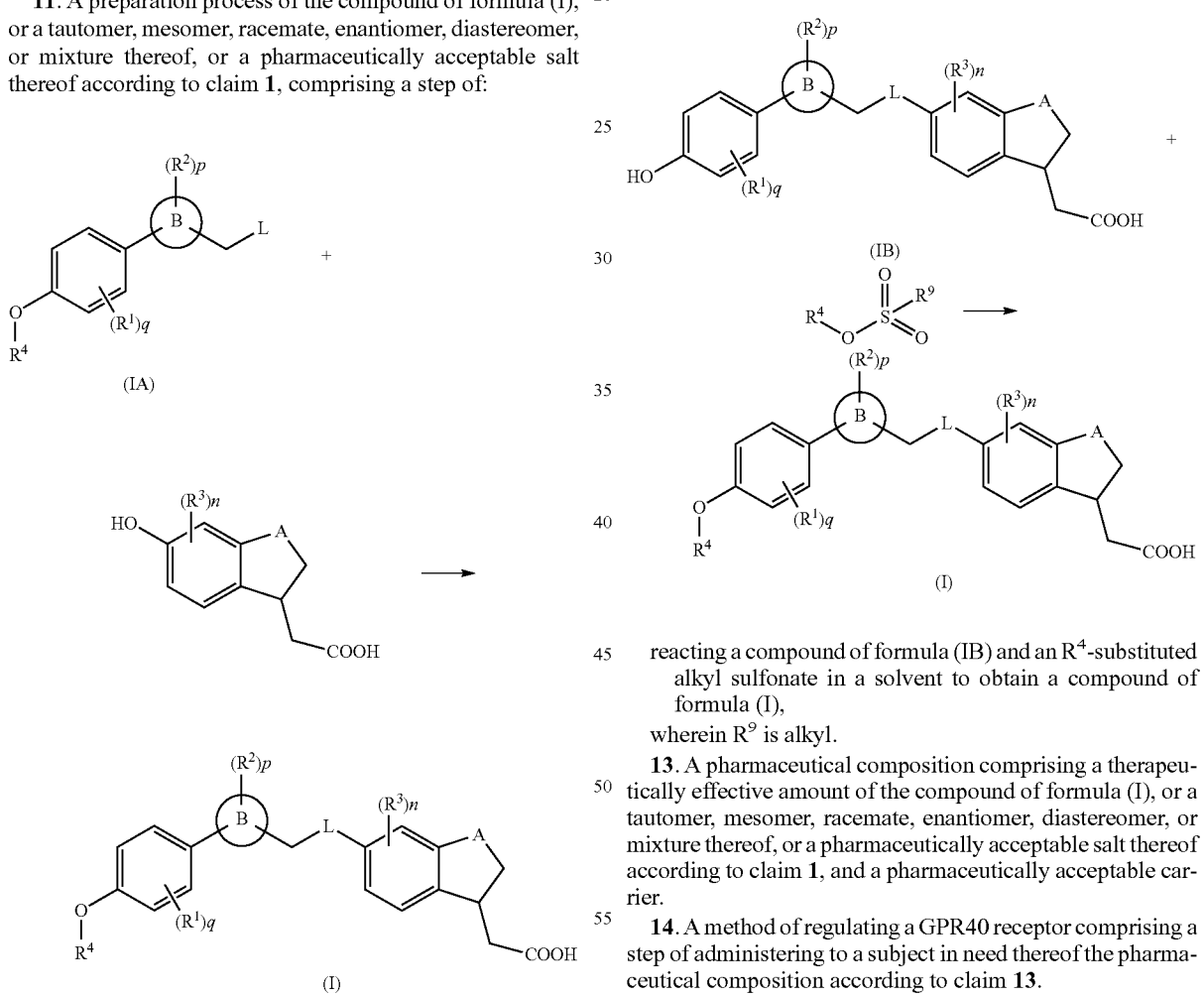

condensing a compound of formula (IA) with a hydroxyl-substituted benzocyclic compound in a solvent to obtain a compound of formula (I).

12. A preparation process of the compound of formula (I), or a tautomer, mesomer, racemate, enantiomer, diastereomer, or mixture thereof, or a pharmaceutically acceptable salt thereof according to claim 1, comprising a step of:

reacting a compound of formula (IB) and an $R^4$-substituted alkyl sulfonate in a solvent to obtain a compound of formula (I), wherein $R^9$ is alkyl.

13. A pharmaceutical composition comprising a therapeutically effective amount of the compound of formula (I), or a tautomer, mesomer, racemate, enantiomer, diastereomer, or mixture thereof, or a pharmaceutically acceptable salt thereof according to claim 1, and a pharmaceutically acceptable carrier.

14. A method of regulating a GPR40 receptor comprising a step of administering to a subject in need thereof the pharmaceutical composition according to claim 13.

15. A method of treating a disorder selected from the group consisting of diabetes comprising a step of administering to a subject in need thereof the pharmaceutical composition according to claim 13.

16. A method of activating a GPR40 receptor, comprising a step of administering to a subject in need thereof the pharmaceutical composition according to claim 13.

17. The method according to claim 15, wherein the disorder is type II diabetes.

18. A compound, or a tautomer, mesomer, racemate, enantiomer, diastereomer, or mixture thereof, or a pharmaceutically acceptable salt thereof selected from the group consisting of:

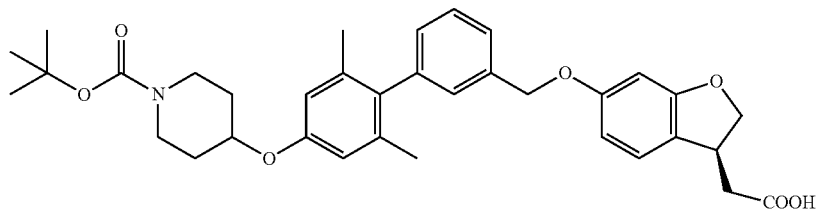

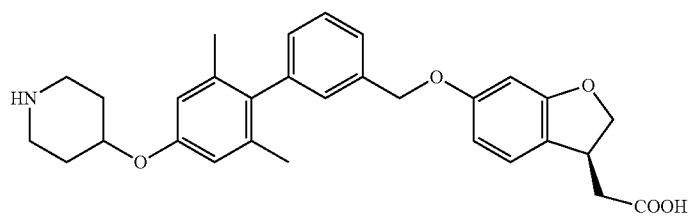

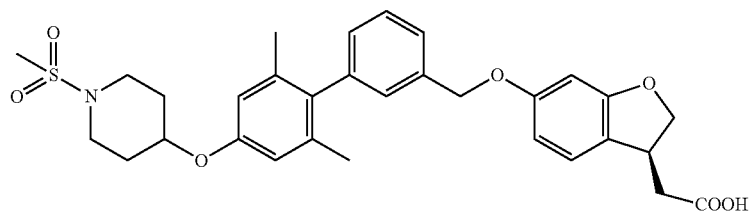

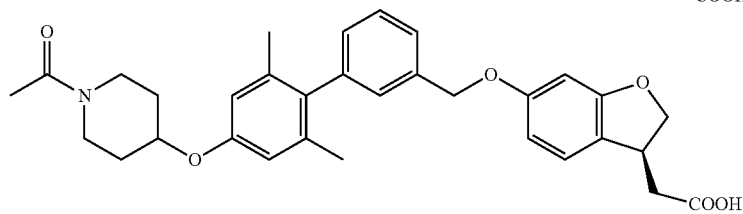

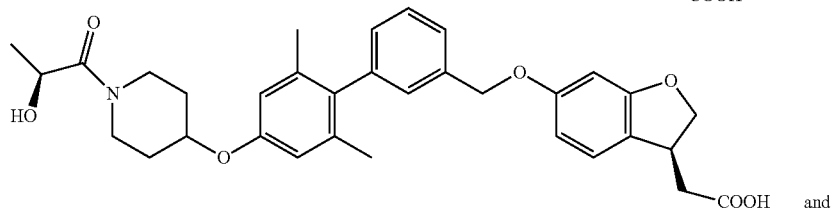 and

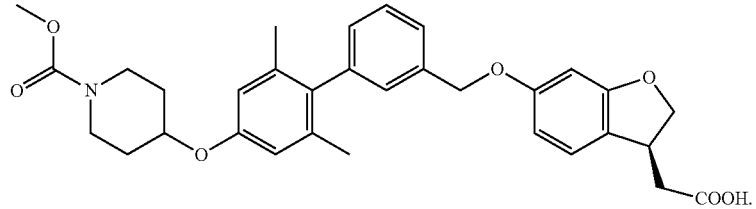

19. A pharmaceutical composition comprising a therapeutically effective amount of the compound, or a tautomer, mesomer, racemate, enantiomer, diastereomer, or mixture thereof, or a pharmaceutically acceptable salt thereof according to claim 18, and a pharmaceutically acceptable carrier.

20. A method of regulating a GPR40 receptor comprising a step of administering to a subject in need thereof the pharmaceutical composition according to claim 19.

21. A method of activating a GPR40 receptor, comprising a step of administering to a subject in need thereof the pharmaceutical composition according to claim 19.

22. A method of treating a disorder selected from the group consisting of diabetes comprising a step of administering to a subject in need thereof the pharmaceutical composition according to claim 19.

23. The method according to claim 22, wherein the disorder is type II diabetes.

* * * * *